United States Patent
Wozniak-Knopp et al.

(10) Patent No.: US 11,623,963 B2
(45) Date of Patent: Apr. 11, 2023

(54) CYSTEINE ENGINEERED ANTIGEN-BINDING MOLECULES

(71) Applicant: MERCK PATENT GMBH, Darmstadt (DE)

(72) Inventors: Gordana Wozniak-Knopp, Vienna (AT); Florian Rüker, Vienna (AT); Gerhard Stadlmayr, Vienna (AT); Jakub Rybka, Poznan (PL); Nicolas Rasche, Darmstadt (DE); Stephan Dickgiesser, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 92 days.

(21) Appl. No.: 16/650,124

(22) PCT Filed: Oct. 3, 2018

(86) PCT No.: PCT/EP2018/076900
§ 371 (c)(1),
(2) Date: Mar. 24, 2020

(87) PCT Pub. No.: WO2019/068756
PCT Pub. Date: Apr. 11, 2019

(65) Prior Publication Data
US 2020/0277399 A1 Sep. 3, 2020

(30) Foreign Application Priority Data
Oct. 3, 2017 (EP) ..................................... 17194497

(51) Int. Cl.
*C07K 16/32* (2006.01)
*A61K 47/68* (2017.01)
*A61K 9/00* (2006.01)

(52) U.S. Cl.
CPC ............ *C07K 16/32* (2013.01); *A61K 9/0029* (2013.01); *A61K 47/6803* (2017.08); *C07K 2317/524* (2013.01); *C07K 2317/526* (2013.01); *C07K 2317/77* (2013.01)

(58) Field of Classification Search
CPC .............. C07K 16/32; C07K 2317/524; C07K 2317/526; C07K 2317/77; C07K 2317/24; C07K 16/2863; C07K 16/00; A61K 9/0029; A61K 47/6803; A61K 47/68; G01N 33/53
See application file for complete search history.

(56) References Cited

U.S. PATENT DOCUMENTS

| | | | |
|---|---|---|---|
| 6,331,415 | B1 | 12/2001 | Cabilly et al. |
| 7,521,541 | B2 | 4/2009 | Eigenbrot et al. |
| 8,562,986 | B2 | 10/2013 | Goodman et al. |
| 2012/0094874 | A1 | 4/2012 | Rüker et al. |
| 2014/0038287 | A1* | 2/2014 | Elson ........................ A61P 1/06 435/375 |

FOREIGN PATENT DOCUMENTS

| | | |
|---|---|---|
| WO | WO 2009/000006 | 12/2008 |
| WO | WO 2009/132876 | 11/2009 |
| WO | WO 2011/003811 | 1/2011 |
| WO | WO 2013/070565 | 5/2013 |
| WO | WO 2014/124316 | 8/2014 |
| WO | WO 2015/157595 | 10/2015 |
| WO | WO 2017/112624 | 6/2017 |

OTHER PUBLICATIONS

IMGT Scientific chart (Year: 2016).*
Lloyd et al. Protein Engineering, Design & Selection 22:159-168 (Year: 2009).*
Edwards et al., J Mol Biol. 334(1): 103-118 (Year: 2003).*
Piche-Nicholas et al MABS 10(1): 81-94 (Year: 2018).*
Baah et al., Molecules 26: 2943 (Year: 2021).*
Austin et al., "Endocytosis and Sorting of ErbB2 and the Site of Action of Cancer Therapeutics Trastuzumab and Geldanamycin," *Mol. Biol. Cell.*, 15(12):5268-5282, 2004.
Brodeur et al., "Mouse-Human Myeloma Partners for the Production of Heterohybridomas," In: Monoclonal Antibody Production Techniques and Applications, Marcel Dekker, Inc., New York, NY, pp. 51-63, 1987.
Chen et al., "Charge-based Analysis of Antibodies with Engineered Cysteines: From Multiple Peaks to a Single Main Peak," *MAbs*, 1(6):563-571, 2009.
Extended European Search Report issued in European Patent Application No. 17194497.8, dated Nov. 30, 217.
Fraczkiewicz et al., "Exact and Efficient Analytical Calculation of the Accessible Surface Areas and Their Gradients for Macromolecules," *J. Comp. Chem.*, 19:319-333, 1998.
Junutula et al., "Rapid Identification of Reactive Cysteine Residues for Site-Specific Labeling of antibody-Fabs," *J. Immunol. Methods*, 332(1-2):41-52, 2008.
Köhler and Milstein, "Continuous Cultures of Fused Cells Secreting Antibody of Predefined Specificity," *Nature*, 256(5517):495-497, 1975.
Kozbor et al., "A Human Hybrid Myeloma for Production of Human Monoclonal Antibodies," *J. Immunol.*, 133(6):3001-3005, 1984.

(Continued)

*Primary Examiner* — Phuong Huynh
(74) *Attorney, Agent, or Firm* — Parker Highlander PLLC

(57) ABSTRACT

A specific antigen-binding member (ABM) comprising a specific antigen-binding moiety and an antibody Fc region comprising a CH2 domain, which is engineered for a cysteine substitution at position 108 and/or 113, wherein numbering is according to the IMGT, and wherein the antibody Fc region does not comprise an antigen-binding CH3 domain; and an ABM conjugate (ABMC) comprising the ABM and at least one heterologous molecule covalently conjugated to one or both of the cysteines at positions 108 and 113 of the CH2 domain.

17 Claims, 11 Drawing Sheets
Specification includes a Sequence Listing.

(56) References Cited

OTHER PUBLICATIONS

Lee and Kwak, "Expression and Functional Reconstitution of a Recombinant Antibody (Fab') Specific for Human Apolipoprotein B-100," *J. Biotechnology*, 101(2):189-198, 2003.
Lefranc et al., "IMGT, the International ImMunoGeneTics Database," *Nucleic Acids Res.*, 27(1):209-212, 1999.
Leung et al., "A HER2-specific Modified Fc Fragment (Fcab) Induces Antitumor Effects Through Degradation of HER2 and Apoptosis," *Mol. Ther.*, 23(11):1722-1733, 2015.
PCT International Preliminary Report on Patentability issued in International Patent Application No. PCT/EP2018/076900, dated Apr. 7, 2020.
PCT International Search Report issued in International Patent Application No. PCT/EP2018/076900, dated Nov. 27, 2018.
Riener et al., "Quick Measurement of Protein Sulfhydryls With Ellman's Reagent and with 4,4'-dithiodipyridine," *Anal. Bioanal. Chem.*, 373(4-5):266-276, 2002.
Schymkowitz et al., "The FoldX web server: an online force field," *Nucleic Acids Res.*, 33 (Web Server Issue):W382-388, 2005.
Vinayagam et al., "DSDBASE: a consortium of native and modelled disulphide bonds in proteins," *Nucleic Acids Res.*, 32(Database Issue): D200-202, 2004.
Von Kreudenstein et al., "Improving biophysical properties of a bispecific antibody scaffold to aid developability. Quality by molecular design," *MAbs*, 5(5):646-654, 2013.
Voynov et al., "Design and Application of Antibody Cysteine Variants," *Bioconjug. Chem.*, 21(2):385-392, 2010.
Wibbenmeyer et al., "Cloning, Expression, and Characterization of the Fab Fragment of the Anti-Lysozyme Antibody HyHEL-5," *Biochem. Biophys. Acta.*, 1430(2):191-202, 1999.

\* cited by examiner

Figure 4

Figure 5:
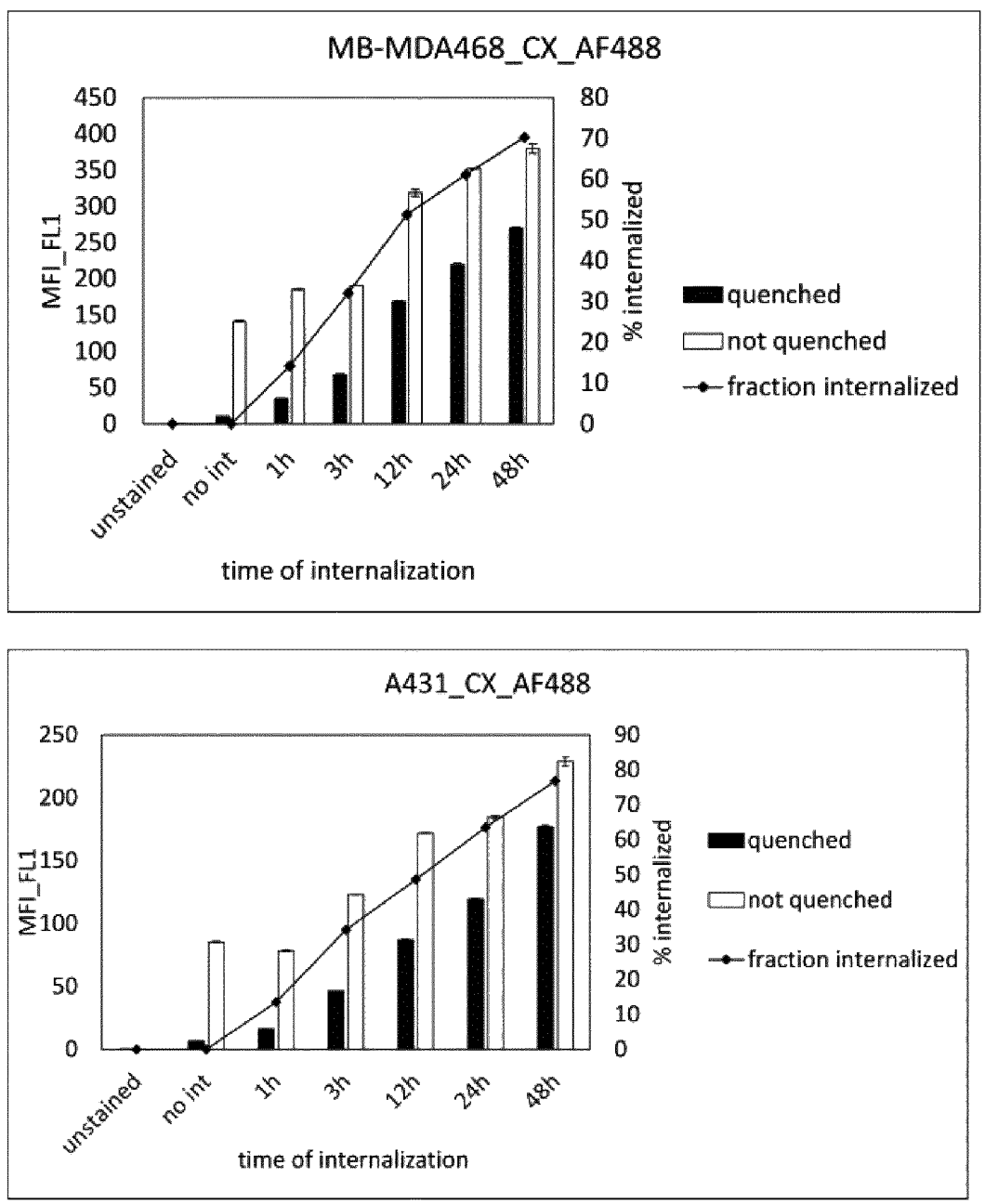

Figure 5 continued
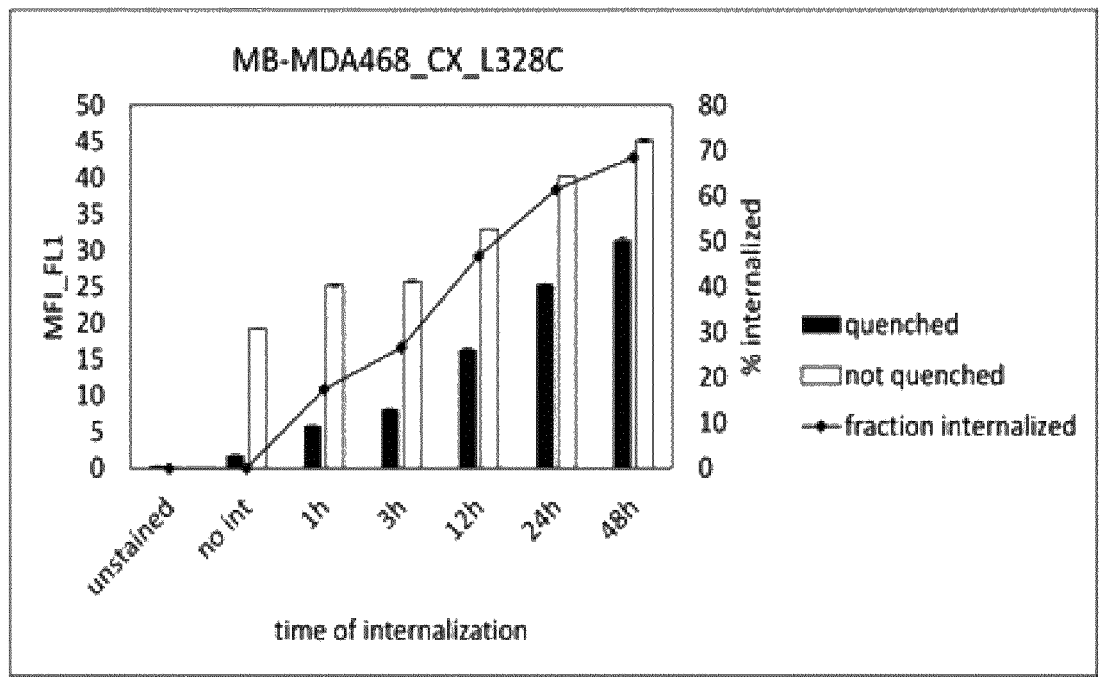
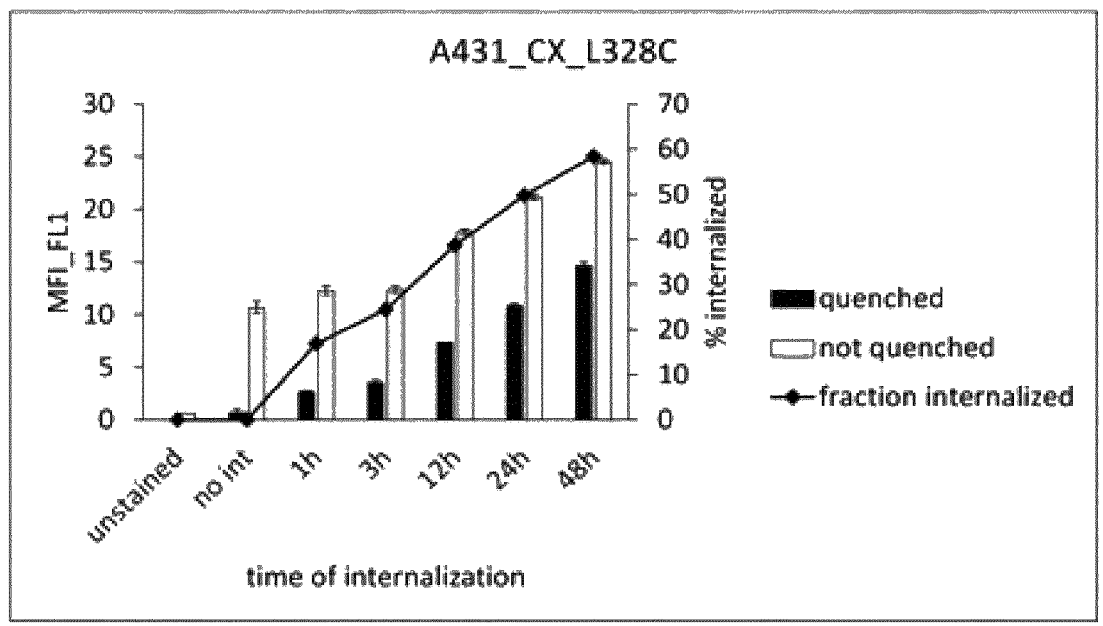

Figure 5 continued
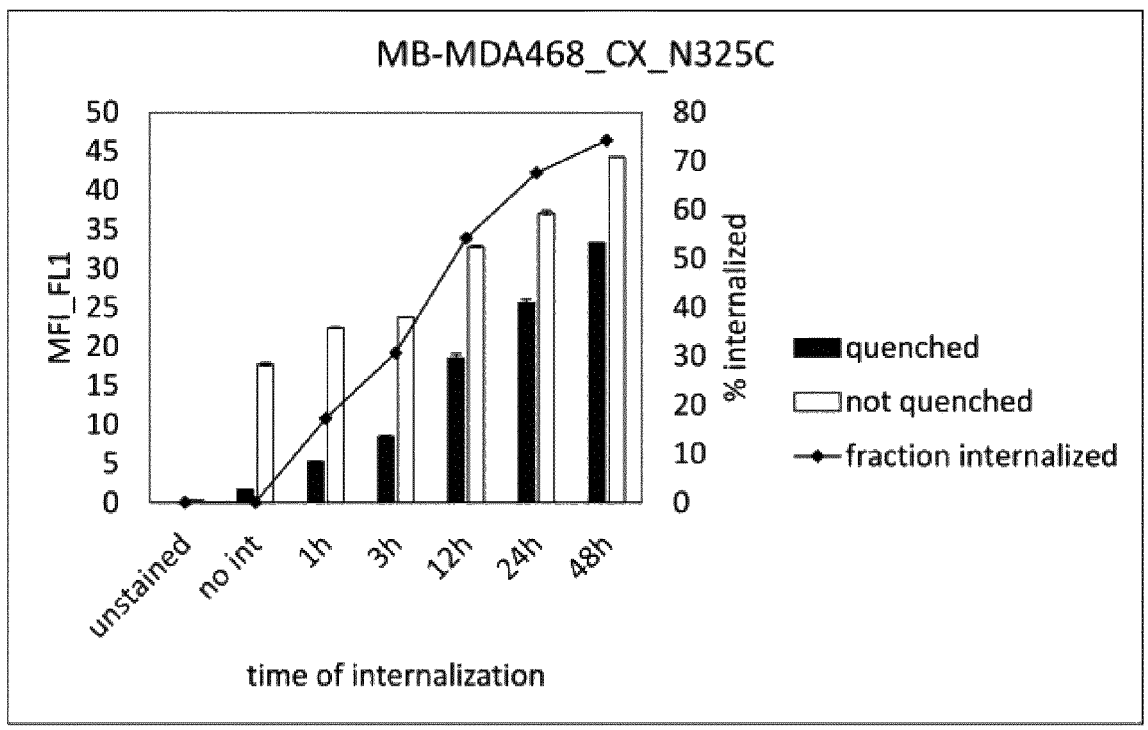
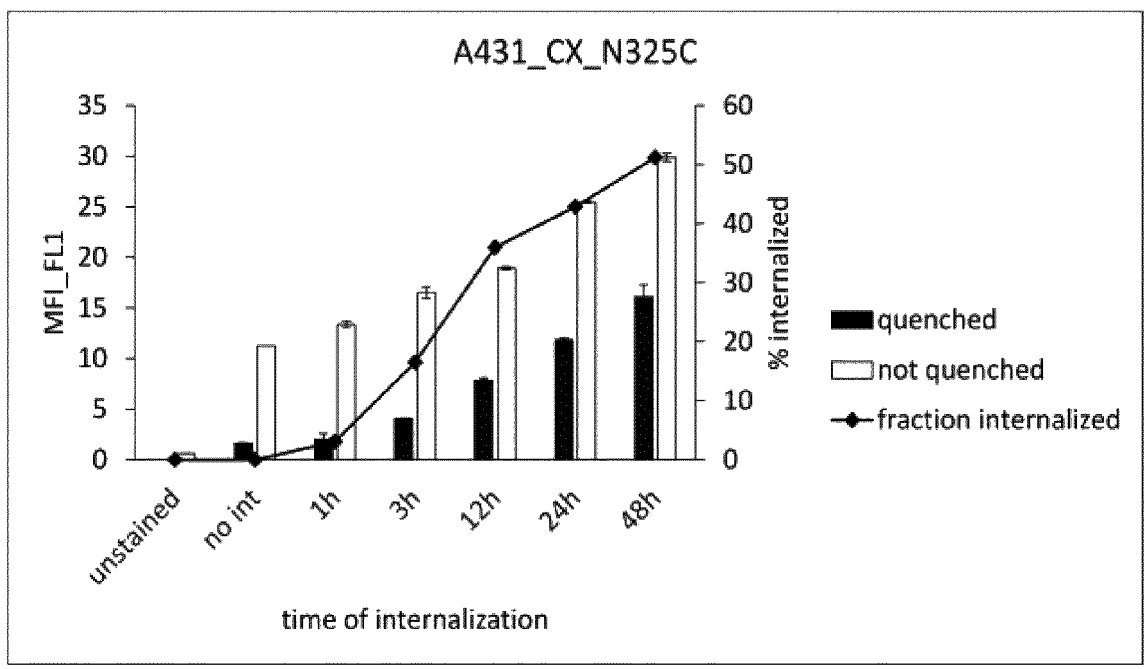

Figure 7

SEQ ID NO:1:
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSCKALPAPIEKTISKAKG

SEQ ID NO:2:
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKACPAPIEKTISKAKG

SEQ ID NO:3:
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSCKACPAPIEKTISKAKG

SEQ ID NO:4:
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSCKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPGK

SEQ ID NO:5:
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKACPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPGK

SEQ ID NO:6:
APELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSCKACPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPGK

SEQ ID NO:7:
EPKSCDKTHTCPPCP

SEQ ID NO:8:
QPREPQVYTLPPSRDELTKNQVSLTCLVKGFYPSDIAVEWESNGQPENNYKTTPPVLDSDGSFFLYSKLTVDKSRW
QQGNVFSCSVMHEALHNHYTQKSLSLSPGK

SEQ ID NO:9:
QPFRPEVHLLPPSREEMTKNQVSLTCLARGFYPKDIAVEWESNGQPENNYKTTPSRQEPSQGTTTFAVTSKLTVDK
SRWQQGNVFSCSVMHEALHNHYTQKTISLSPGK

SEQ ID NO:10
QPREPQVYTLPPPSEELALNELVTLTCLVKGFYPSDIAVEWLQGSQELPREKYLTWAPVLDSDGSFFLYSILRVAA
EDWKKGDTFSCSVMHEALHNHYTQKSLDRSPGK

Figure 8
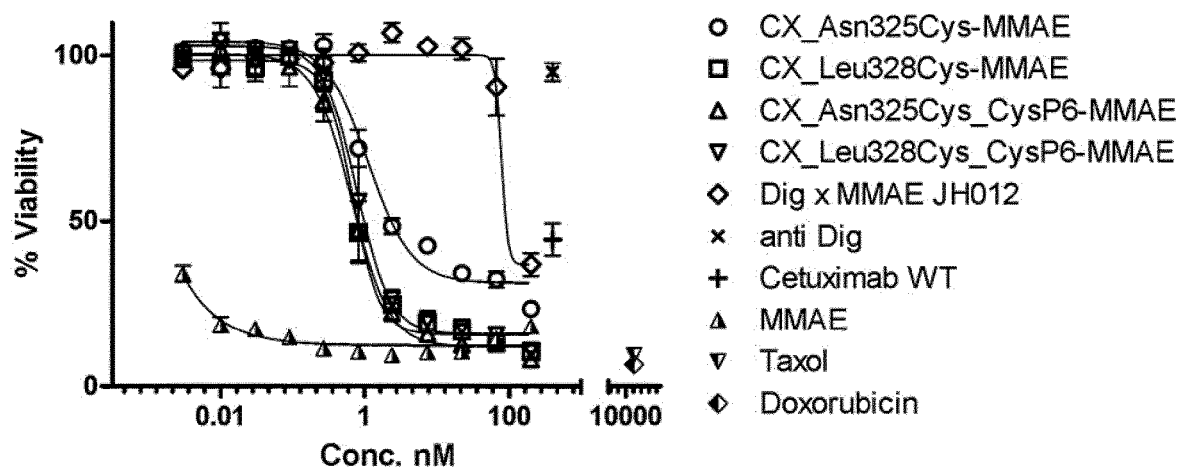
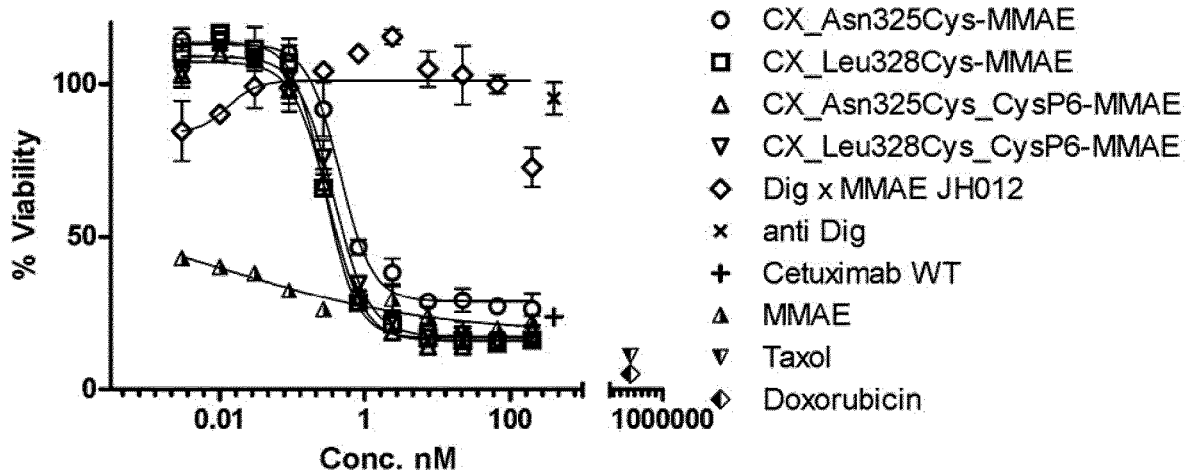

CYSTEINE ENGINEERED ANTIGEN-BINDING MOLECULES

This application is a national phase application under 35 U.S.C. § 371 of International Application No. PCT/EP2018/076900, filed Oct. 3, 2018, which claims the benefit of European Patent Application No. 17194497.8, filed Oct. 3, 2017, the entirety of each of which is incorporated herein by reference.

Pursuant to 37 C.F.R. 1.821(c), a sequence listing is submitted herewith as an ASCII compliant text file named "REDLP0004US ST25.txt", created on Mar. 20, 2020 and having a size of ~83 kilobytes. The content of the aforementioned file is hereby incorporated by reference in its entirety.

FIELD

The invention relates to antigen-binding members (ABM) which comprise a cysteine engineered antibody Fc region, and ABM conjugates, wherein one or more heterologous molecules are conjugated to any of the cysteines.

BACKGROUND

Monoclonal antibodies have been widely used as therapeutic antigen-binding molecules. The basic antibody structure will be explained here using as example an intact IgG1 immunoglobulin.

Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy-terminal CH3, at the base of the Y's stem. A short stretch, the switch, connects the heavy chain variable and constant regions. The hinge connects CH2 and CH3 (the Fc fragment) to the remainder of the antibody (the Fab fragments). One Fc and two identical Fab fragments can be produced by proteolytic cleavage of the hinge in an intact antibody molecule. The light chains are constructed of two domains, variable (VL) and constant (CL), separated by a switch.

Disulfide bonds in the hinge region connect the two heavy chains. The light chains are coupled to the heavy chains by additional disulfide bonds. Asn-linked carbohydrate moieties are attached at different positions in constant domains depending on the class of immunoglobulin. For IgG1 two disulfide bonds in the hinge region, between Cys235 and Cys238 pairs, unite the two heavy chains. The light chains are coupled to the heavy chains by two additional disulfide bonds, between Cys220 (EU Index numbering) or Cys233 (numbering according to Kabat) in the CH1 domains and Cys214 in the CL domains (EU index and Kabat numbering). Carbohydrate moieties are attached to Asn306 of each CH2, generating a pronounced bulge in the stem of the Y.

These features have profound functional consequences. The variable regions of both the heavy and light chains (VH) and (VL) lay at the N-terminal region, i.e. the "tips" of the Y, where they are positioned to react with antigen. This tip of the molecule is the side on which the N-terminus of the amino acid sequence is located. The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y.

Two types of light chain, termed lambda (λ) and kappa (κ), are found in antibodies. A given immunoglobulin either has κ chains or λ chains, never one of each. No functional difference has been found between antibodies having λ or κ light chains.

Each domain in an antibody molecule has a similar structure of two beta sheets packed tightly against each other in a compressed antiparallel beta barrel. This conserved structure is termed the immunoglobulin fold. The immunoglobulin fold of constant domains contains a 3-stranded sheet packed against a 4-stranded sheet. The fold is stabilized by hydrogen bonding between the beta strands of each sheet, by hydrophobic bonding between residues of opposite sheets in the interior, and by a disulfide bond between the sheets. The 3-stranded sheet comprises strands C, F, and G, and the 4-stranded sheet has strands A, B, E, and D. The letters A through G denote the sequential positions of the beta strands along the amino acid sequence of the immunoglobulin fold.

The fold of variable domains has 9 beta strands arranged in two sheets of 4 and 5 strands. The 5-stranded sheet is structurally homologous to the 3-stranded sheet of constant domains, but contains the extra strands C' and C". The remainder of the strands (A, B, C, D, E, F, G) have the same topology and similar structure as their counterparts in constant domain immunoglobulin folds. A disulfide bond links strands B and F in opposite sheets, as in constant domains.

The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B-C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B-C, C'-C", and F-G of the light chain variable domain and strands B-C, C'-C", and F-G of the heavy chain variable domain.

The loops which are not CDR-loops in a native immunoglobulin, or not part of the antigen-binding pocket as determined by the CDR loops and optionally adjacent loops within the CDR loop region, do not have antigen binding or epitope binding specificity, but contribute to the correct folding of the entire immunoglobulin molecule and/or its effector or other functions and are therefore called structural loops. Thus, a "structural loop" or "non-CDR-loop" according to the present invention is to be understood in the following manner: immunoglobulins are made of domains with a so called immunoglobulin fold. In essence, antiparallel beta sheets are connected by loops to form a compressed antiparallel beta barrel. In the variable region, some of the loops of the domains contribute essentially to the specificity of the antibody, i.e., the binding to an antigen. These loops are called CDR-loops. All other loops of antibody domains are rather contributing to the structure of the molecule and/or the effector function. These loops are defined herein as structural loops or non-CDR-loops.

Antigen-binding Fc fragments (also referred to as Fcab™ [f-star; Fc fragment with an antigen binding site (Wozniak- Knopp et al., 2010)] comprising e.g., a modified IgG1 Fc domain which specifically binds to an antigen with high affinity, are e.g., described in WO 2009/132876 A1 and WO 2009/000006 A1.

Various antibody constructs are currently in development for providing antibody drug conjugates (ADC).

ADCs combine the specificity of an antibody with the cytotoxicity of a drug, thus improving the therapeutic effect of both. ADCs usually consist of the antibody, a linker and a cytotoxin. The role of an antibody is targeted delivery of the drug to a cell. In specific cases, efficient internalization of the antigen-antibody complex is crucial for the mechanism of ADC action. After internalization cleavage of the linker occurs and the toxin is released in its active form. Prior to its release, the toxin is inactive due to the conjugation and therefore stable and harmless while in the circulation.

Cytotoxins currently used in ADCs can be divided into two categories: those interacting with microtubules by inhibiting microtubule assembly (e.g. maytansinoids and auristatins) and those binding to the minor groove of DNA and causing cell death by inducing DNA strand breaks (e.g. calicheamicin). Mylotarg® (Wyeth, gemtuzumab-ozogamicin) uses a calicheamicin derivative and was the first ADC approved by the U.S. Food and Drug Administration for the treatment of acute myeloid leukemia. It was withdrawn from the market in 2010 due to safety concerns and unsatisfactory patient benefits. Currently there are several ADCs in various clinical trials.

Typically, a linker is used which is stable in the circulation, since early release of the cytotoxin could otherwise lead to nonspecific cell killing. Selected linkers are readily cleavable in the lysosomes and release the drug inside the cell. Currently, there are four different classes of linkers: acid-labile hydrazone linkers that are stable at neutral pH (e.g. blood) and undergo hydrolysis in acidic environment; disulfide-based linkers which are cleaved in the cytosol because of the high intracellular concentration of glutathione; peptide-based linkers, which conjugate the drug to the antibody by a peptide bond and are released due to lysosomal proteases; thioether-containing noncleavable linkers, which are much more stable and are postulated to release the drug through intracellular proteolytic degradation.

Free thiol (SH)-groups can be introduced by partially reducing interchain disulfides or by introducing new surface cysteines via site directed mutagenesis to create specific conjugation sites (Junutula, Bhakta, et al., 2008; Voynov et al., 2010). Thereby a construct with reactive thiol groups is provided as a "preADC". Engineering of a surface cysteine has been described in WO2013/070565A1, WO22014/124316A1, WO2015/157595A1 and WO2017/112624A1, at various positions.

There is a need for improved cysteine engineering of antibodies without altering the basic properties of an Fc fragment.

SUMMARY OF THE INVENTION

It is the objective of the present invention to provide improved cysteine engineered ABM, which provide for reactive thiol groups that are readily accessible for drug conjugation.

The object is solved by the subject of the present invention.

According to the invention, there is provided a specific antigen-binding member (ABM) comprising a specific antigen-binding moiety and an antibody Fc region comprising a CH2 domain, which is engineered (understood as mutated or otherwise modified compared to a wild-type CH2 domain) for a cysteine substitution at position 108 and/or 113, wherein numbering is according to the IMGT. Specifically, the ABM comprises a specific antigen-binding moiety and an antibody Fc region comprising a CH2 domain, wherein the CH2 domain comprises a cysteine substitution at position 108 and/or 113, wherein numbering is according to the IMGT.

Specifically, one or two cysteines are engineered into the F-G loop of the CH2 domain at the predetermined positions by point mutations substituting the naturally-occurring amino acid by a cysteine. Thereby, one or more free thiol groups are engineered into the ABM.

Free thiol groups are herein understood as sulfhydryl (—SH) functional groups of cysteine residues which remain unpaired (not cross-linked) with other cysteine residues of the ABM, and, which may be uncapped or capped with chemical entities (other than the ABM) e.g., by cysteine or glutathione, which may be present in a cell culture medium upon expressing the ABM in the cell culture. Specifically, the free (unpaired) cysteine residues are introduced into the ABM for site-specific labelling and/or drug conjugation.

The indicated positions surprisingly turned out to be well-suitable despite of being "hidden" or "buried" when determining the exposure of amino acid residues to interactions with solvents. In the prior art, solvent exposure of a position was indicative of favorable accessibility for drug conjugation.

Specifically, the antigen-binding moiety comprises an antigen-binding portion of an antibody, or the binding site of any one of an enzyme, an adhesion protein, a ligand or a ligand binding portion of a receptor, which binding site is capable of binding a cognate structure of a binding partner. Specifically, the antigen-binding moiety is composed of the binding site of a naturally occurring receptor.

Specifically, the antigen-binding moiety comprises one or more antibody variable domains, in particular a VH and a VL domain, which associate to form a VH/VL binding site involving or composed of three VH-CDR regions and three VL-CDR regions.

Specific ABM described herein include an antigen binding CH3 domain which comprises an antigen-binding site, e.g., wherein one or more amino acid sequences in at least one structural loop region are modified thereby obtaining a modified structural loop region which specifically binds to an epitope of an antigen, e.g., a surface antigen to which an unmodified CH3 domain does not significantly bind. Antigen binding CH3 domains comprising an antigen-binding site in the structural loops have been shown to have favorable properties in an antigen-binding Fc or in an antigen-binding Fc-part of an antibody or of any other ABM comprising such Fc.

Specific ABM described herein consist of or include an antigen binding Fc described herein which comprises an antigen-binding site, e.g., wherein one or more amino acid sequences in at least one structural loop region are modified thereby obtaining a modified structural loop region which specifically binds to an epitope of an antigen, e.g., a surface antigen, such as Her2, to which an unmodified Fc does not significantly bind. Antigen binding Fcs comprising an antigen-binding site in the structural loops have been shown to have favorable properties as Fcabs or as antigen-binding Fc-part of an antibody or of any other ABM comprising such Fc.

Specific ABM described herein include antibodies comprising an antigen binding CH3 domain or Fc, e.g., a full-length antibody, such as those having an IgG structure, which comprises one or more (e.g., only 2) antigen-binding CH3 domains, or which comprises an antigen-binding Fc substituting the wild-type CH3 domain(s) and Fc, respectively. An exemplary binding member is a full-length bispecific antibody, called mAb²™ (f-star).

According to a preferred embodiment, the antigen-binding moiety is selected from the group consisting of a Fab, F(ab')₂, scFv, Fd, Fv, an antigen-binding CH3, Fcab, and one or more antibody domains comprising at least one antibody binding site in the CDR or non-CDR (or structural) loops.

Specifically,
a) the antigen-binding moiety is fused to the N-terminus of said antibody CH2 domain; and/or
b) the antigen-binding moiety is comprised in a CH3 domain and/or in the Fc region.

Specifically, the antigen-binding moiety is comprised in the structural loops of the Fc region, in particular of the C-terminal structural loops of one or two CH3 domains comprised in the Fc region.

According to a specific embodiment, the antigen-binding moiety is comprised in an antigen-binding Fc or in a full-length multivalent or bispecific antibody comprising an antigen-binding Fc.

Specifically, the antigen-binding moiety is fused to the N-terminus of the CH2 domain via a linker and/or hinge region. Specifically, the hinge region is any peptidic hinge region composed of an amino acid sequence, which is a hinge region of a naturally-occurring immunoglobulin. Specifically, the hinge region is of a human immunoglobulin e.g., comprising or consisting of the amino acid sequence identified as SEQ ID NO:7.

In the ABM described herein, the linkage of antibody domains is specifically by recombinant fusion or chemical linkage. Specific linkage may be through linking the C-terminus of one domain to the N-terminus of another domain, e.g. wherein one or more amino acid residues in the terminal regions are deleted to shorten the domain size, or extended to increase flexibility of the domains.

Specifically, a shortened domain sequence may be used, which comprises a deletion of the C-terminal and/or N-terminal region, such as to delete at least 1, 2, 3, 4, or 5, up to 6, 7, 8, 9, or 10 amino acids.

Specifically, a linking sequence may be used, which is a linker or a hinge region or at least part of the hinge region of an immunoglobulin, such as a peptidic linker composed of an amino acid sequence e.g., including at least 1, 2, 3, 4, or 5 amino acids, up to 10, 15, or 20 amino acids. A linking sequence is herein also referred to as "junction". A domain may be extended by a linker e.g. through an amino acid sequence that originates from the N—, or C-terminal region of an antibody domain that would natively be positioned adjacent to the domain, such as to include the native junction between the domains. Alternatively, the linker may contain an amino acid sequence originating from the hinge region. However, the linker may as well be an artificial sequence, e.g. consisting of serial Gly and/or Ser amino acids, preferably with a length of 5 to 20 amino acids, preferably 8 to 15 amino acids.

Specifically, the C-terminus of the CH2 domain is fused to the N-terminus of a CH3 domain, preferably wherein the Fc region is comprised in an antibody Fc consisting of a dimer of antibody heavy chains.

Specifically, the Fc region is comprised in an Fc part of an antibody (herein referred to as "antibody Fc" or "Fc"), which is composed of two CH2 domains and two CH3 domains, wherein a first chain of a CH2 domain fused to a CH3 domain is forming a dimer with a second chain of a CH2 domain fused to a CH3 domain.

The Fc region is specifically characterized by a dimer of Fc chains each characterized by comprising the chain of CH2-CH3 antibody domains, which dimer can be a homodimer or a heterodimer, e.g. wherein a first Fc chain differs from a second Fc chain in at least one point mutation in the CH2 and/or CH3 domains.

Specifically, the one or both of the CH2 domains of an Fc are cysteine engineered to comprise one or both of the cysteine substitutions at position 108 and/or 113, wherein numbering is according to the IMGT. Specifically, the Fc comprises one or both of the cysteine substitutions in each CH2 domain, such that the Fc comprises only 1, 2, 3, or 4 free thiol groups.

Specifically, the antigen-binding moiety is fused to the Fc or Fc region, in particular to the N-terminus of a CH2 domain, or to a hinge region linking the antigen-binding moiety to the CH2 domain.

According to a specific embodiment, the antigen-binding moiety is incorporated within the Fc region, e.g. within the C-terminal loop region of a CH3 domain, which are understood as "structural loop region".

According to a specific example, the antigen-binding moiety is an antigen-binding site of an Fcab. Specifically, the Fcab comprises one or two antigen-binding moieties. Specifically, the Fcab comprises two antigen-binding moieties, wherein a first antigen-binding moiety is incorporated into the C-terminal structural loop region of a first CH3 domain, and a second antigen-binding moiety is incorporated into the C-terminal structural loop region of a second CH3 domain.

In addition, the Fcab can be part of a construct comprising one or more antigen-binding moieties, e.g. two antigen-binding moieties, wherein a first one is fused to the N-terminus of a first CH2-CH3 chain, e.g. via a linker or hinge region, and a second one is fused to the N-terminus of a second CH2-CH3 chain e.g., via a linker or hinge region.

Specifically, the ABM is an antigen-binding Fc (in particular an Fcab), or a full-length multivalent or bispecific antibody comprising an antigen-binding Fc (in particular a mAb²).

According to a specific example, the ABM is a full-length immunoglobulin having the structure of any one of an IgG, IgA, IgM, or IgE, wherein the Fc is exchanged for an Fcab. Thereby, the ABM comprises three, four, or at least three or four antigen-binding moieties, and optionally two, three or more different antigen-binding specificities.

In a particular embodiment, the ABM is a full-length multivalent or bispecific antibody comprises
i) two antigen-binding moieties, each with one antigen-binding site (e.g., each being a Fab arm of an antibody), wherein each of the antigen-binding sites is composed of CDR loops, and
ii) one antigen-binding moiety comprising one or two antigen binding sites (e.g. an antigen-binding Fc comprising an antigen-binding site in one or two CH3 domains), wherein each of the antigen-binding sites is composed of non-CDR loops.

Specifically, the ABM is an antibody selected from the group consisting of a monoclonal antibody, a bispecific antibody, a multispecific antibody, an antigen-binding part of an antibody, an Fcab molecule, and an antibody comprising an Fcab molecule. Specifically, the ABM is a human, humanized or chimeric antibody. Specifically, the ABM is a human antibody, in particular a human IgG antibody, which is modified for introducing the point mutation in the CH2 domain as described herein, and optionally further modified to introduce one or more additional antigen binding sites.

Specifically, the ABM is bispecific or multispecific, specifically recognizing two or more different antigens, wherein a specific antigen is recognized by one, two or more antigen-binding moieties. Specifically, the ABM is bivalent or multivalent, wherein an antigen is specifically recognized by two or more antigen-binding moieties, respectively.

Specifically, the ABM; is cross-reactive, wherein two or more antigens are specifically recognized by one cross-specific binding site of antigen-binding moiety.

Specifically, the ABM is a monoclonal antibody. Specifically, a preparation of a monoclonal antibody is provided which is obtained by cultivating a cell line of host cell that is engineered by recombinant techniques to express monoclonal antibodies.

According to a specific embodiment, the CH2 domain comprises one or two cysteine substitutions, which are N108C and/or L113C, wherein numbering is according to the IMGT.

Specifically, the CH2 domain is of a mammalian species e.g., human, mouse, rabbit, goat, camelid, llama, cow or horse, or of an avian species, e.g., hen.

In particular, the CH2 domain is a wild-type CH2 domain consisting of an amino acid sequence that is naturally-occurring besides the one or two cysteines that are engineered into the predetermined positions, thereby obtaining an artificial product.

Specifically, the CH2 domain is of an immunoglobulin of any one of the IgG, IgA, IgM, or IgE isotype, particularly any of an IgG1, IgG2, IgG3, IgG4, IgA1, IgA2, IgD, IgE, or IgM antibody, preferably of a human antibody.

Specifically, the CH2 domain is of a human IgG, in particular IgG1, and comprises one or two cysteine substitutions, which are N108C and/or L113C, wherein numbering is according to the IMGT.

Specifically, the CH2 domain is of a human IgG, in particular IgG1, and comprises one or two cysteine substitutions, which are N325C and/or L328C, wherein numbering is according to the EU index of Kabat.

Specifically, the CH2 domain comprises or consists of the amino acid sequence identified as any of SEQ ID NO:1, 2 or 3, or an amino acid sequence with at least 90% sequence identity to any of SEQ ID NO:1, 2 or 3.

Functional variants of a CH2 domain are particularly characterized by a certain degree of sequence identity, such as e.g. at least 90% or at least 95% to the naturally-occurring sequence are particularly characterized by the beta-barrel structure of the antibody domain which resembles the structure of respective domains in the human IgG, IgA, IgM or IgE structure, in particular a human IgG1 structure.

Specifically, a functionally active variant of a CH2 domain can be used comprising one or more point mutations in the naturally-occurring sequence, preferably up to 10 point mutations, in particular any of 1, 2, 3, 4, 5, 6, 7, 8, 9, or 10 point mutations.

Specifically, the Fc or Fc region is of a mammalian species e.g., human, mouse, rabbit, goat, camelid, llama, cow or horse, or of an avian species, e.g., hen.

In particular, the Fc region comprises a wild-type CH2-CH3 domain sequence consisting of an amino acid sequence that is naturally-occurring besides the one or two cysteines that are engineered into the CH2 at the predetermined positions, thereby obtaining an artificial product.

Specifically, the Fc or Fc region is of an immunoglobulin of any one of the IgG, IgA, IgM, or IgE isotype, particularly any of an IgG1, IgG2, IgG3, IgG4, IgA1, IgA2, IgD, IgE, or IgM antibody, preferably of a human antibody.

Specifically, the Fc region composed of one CH2 and one CH3 domain is of a human IgG, in particular IgG1, and comprises one or two cysteine substitutions in the CH2 domain, which are N108C and/or L113C, wherein numbering is according to the IMGT.

Specifically, the Fc region composed of one CH2 and one CH3 domain is of a human IgG, in particular IgG1, and comprises one or two cysteine substitutions in the CH2 domain, which are N325C and/or L328C, wherein numbering is according to the EU index of Kabat.

Specifically, the Fc region comprises or consists of the amino acid sequence identified as any of SEQ ID NO:4, 5 or 6, or an amino acid sequence with at least 90% sequence identity to any of SEQ ID NO:4, 5 or 6.

Functional variants of an Fc region are particularly characterized by a certain degree of sequence identity, such as e.g. at least 90% or at least 95% to the naturally-occurring sequence are particularly characterized by the beta-barrel structure of the CH2 and CH3 antibody domains which resembles the structure of respective domains in the human IgG, IgA, IgM or IgE structure, in particular a human IgG1 structure.

Specifically, a functionally active variant of an Fc region can be used comprising one or more point mutations in the naturally-occurring sequence in one or both of the CH2 and CH3 domains comprised in the Fc region, preferably up to 10 point mutations, in particular any of 1, 2, 3, 4, 5, 6, 7, 8, 9, or 10 point mutations in one or both of the antibody domains, CH2 and CH3.

According to certain embodiments, the ABM specifically recognizes a target antigen expressed on the surface of a target cell, in particular through one or more antigen-binding moieties. Such surface antigens are specifically on the surface of target cells, which are any of mammalian, in particular of human cells, which are targeted to react with the ABM or any heterologous moiety linked to said ABM, upon binding to the antigen.

Specifically, a target antigen is selected from cell surface antigens, including receptors, in particular from the group consisting of erbB receptor tyrosine kinases (such as EGFR, HER2 including Her2neu, HER3 and HER4). In addition further antigens may be targeted, e.g., molecules of the TNF-receptor superfamily, such as Apo-1 receptor, TNFR1, TNFR2, nerve growth factor receptor NGFR, CD40, CD40-Ligand, OX40, TACI, BCMA, BAFF-receptor, T-cell surface molecules, T-cell receptors, T-cell antigen, Apo-3, DR4, DR5, DR6, decoy receptors, such as DcR1, DcR2, CAR1, HVEM, GITR, ZTNFR-5, NTR-1, TNFL1, IGFR-1, c-Met, but not limited to these molecules, B-cell surface antigens, such as CD10, CD19, CD20, CD21, CD22, DC-SIGN, antigens or markers of solid tumors or hematologic cancer cells, cells of lymphoma or leukaemia, other blood cells including blood platelets, but not limited to these molecules.

According to specific examples, the surface antigens are selected from the group consisting of receptor tyrosine kinases (ErbB family).

Specifically, the ABM is internalizing upon binding to a target cell. According to specific examples, the internalizing ABM specifically recognize antigens selected from the group consisting of receptor tyrosine kinases (ErbB family). Internalization of the ABM upon binding to the target cell is determined by standard techniques, including e.g., flow cytometry, radiolabelled antibody studies, image analysis, or cytotoxic assays using antibody drug conjugates.

Specifically, the ABM comprises a functional antigen-binding site composed of a VH/VL domain pair, capable of binding a target with a high affinity and a KD of less than any of $10^{-6}$M, $10^{-7}$M, $10^{-8}$M, $10^{-9}$M, or $10^{-10}$M. Specifically, the ABM is a bispecific or heterodimeric antibody targeting two different antigens, wherein each of the antigens is recognized by the antibody with a KD of less than any of $10^{-6}$M, $10^{-7}$M, $10^{-8}$M, $10^{-9}$M, or $10^{-10}$M.

Specifically, the ABM is a monospecific or bispecific antibody targeting at least EGFR. According to a specific example, the antibody is cetuximab (ImClone Systems, Bristol-Myers Squibb, Merck KGaA).

Specifically, the ABM is a bispecific or multispecific antibody, wherein a first target is any of CD3, CD16 or Her2neu, and a second target is EGFR.

According to a specific embodiment, the ABM comprises two different Fab arms, thereby providing for two different Fv structures, each with specific binding characteristics. Specifically, the ABM is a heterodimeric or bispecific antibody targeting two different antigens or two different epitopes of an antigen.

Specifically, the ABM is a heterodimeric or bispecific antibody comprising a first and a second Fab arm recognizing different antigens or epitopes, such as a bispecific full-length immunoglobulin.

For example, the antigen-binding moiety used in the ABM described herein is a Fab arm, which is a dimer of a heavy chain (HC) consisting of a VH-CH1 domain sequence and a light chain (LC) consisting of a VL-CL (kappa or lambda) domain sequence, with or without any disulfide bridges, a hinge domain and/or linker sequences connecting antibody domains. A Fab arm is typically understood as a Fab fragment (or Fab part) when cleaved from an antibody. The Fab arm is specifically characterized by only one antigen-binding site formed by pairing the VH and VL domains, and is capable of binding the target only monospecifically and monovalently.

According to a specific aspect, the ABM described herein is a heterodimeric antibody comprising two different HCs, each comprising a CH2 and a CH3 domain, and optionally a CH4 domain, which HCs dimerize into an Fc region.

Specifically, the ABM comprises a heterodimeric Fc or Fc region, wherein a first Fc chain differs from a second Fc chain in at least one point mutation in the CH2 and/or CH3 domains.

Specifically, the heterodimeric Fc region comprises two CH3 domains which are engineered to introduce and/or are characterized by one or more of the following:

a) strand-exchange engineered domain (SEED) CH3 heterodimers that are composed of alternating segments of human IgA and IgG CH3 sequences;

b) one or more knob or hole mutations, preferably any of T366Y/Y407'T, F405A/T394'W, T366Y: F405A/T394'W: Y407'T, T366W/Y407'A and S354C:T366W/Y349'C: T366'S: L368'A:Y407'V;

c) a cysteine residue in the first CH3 domain that is covalently linked to a cysteine residue in the second CH3 domain, thereby introducing an interdomain disulfide bridge, preferably linking the C-terminus of both CH3 domains;

d) one or more mutations where repulsive charge suppresses heterodimer formation, preferably any of: K409D/D399'K, K409D/D399'R, K409E/D399'K, K409E/D399'R, K409D:K392D/D399'K:E356'K or K409D:K392D:K370D/D399'K:E356'K:E357'K; and/or e) one or more mutations selected for heterodimer formation and/or thermostability, preferably any of:
T350V:L351Y:F405A:Y407V/T350V:T366L:K392L: T394W,
T350V:L351 Y:F405A:Y407V/T350V:T366L:K392M: T394W,
L351Y:F405A:Y407V/T366L:K392M:T394W,
F405A:Y407V/T366L:K392M:T394W, or
F405A:Y407V/T366 L:T394W,
wherein numbering is according to the EU index of Kabat.

Such CH3 mutations are engineered to produce two different Fc chains and HCs (differing at least by a different sequence of the CH3 domains), respectively, which preferably pair with each other, thereby obtaining a heterodimer of the Fc chains or HCs, substantially reducing the tendency of producing a HC homodimer, i.e. a dimer of two HCs of the same sequence.

In the specification of the CH3 point mutations described herein, the "slash" differentiates the point mutations on one chain or one domain from the point mutations from the other chain or other domain of the respective pair; the "indent" in the amino acid position numbering signifies the second chain or dimer of the heterodimer. The "colon" identifies the combination of point mutations on one of the chains or domains, respectively.

Any of the mutations selected for heterodimer formation as mentioned above or further mutations in accordance with the disclosure of Von Kreudenstein et al. (Landes Bioscience, vol. 5, no. 5, 2013, pp 646-654) can be used.

Preferably, either (i) a knob; or (ii) a hole mutation, or (iii) a knob and hole mutation, is engineered on one chain or domain, and the counterpart (i) hole, or (ii) knob mutation, or (iii) hole and knob mutation, is engineered on the other chain of the heterodimer.

Specifically, a pair of CH3 domains comprising one or two engineered CH3 domains may comprise more than one (additional) interdomain disulphide bridges, e.g. 2, or 3, connecting the pair of two CH3 domains.

Specifically, different mutations (according to a) above) are engineered in both CH3 domains of a respective pair of CH3 domains to produce a cognate (matching) pair, wherein one domain comprises a steric modification of a contact surface in the beta-sheet region that is preferentially attached to the respective contact surface of the other domain through the complementary steric modification. Such steric modifications mainly result from the different amino acid residues and side chains, e.g. to produce a "knob" or "hole" structure, which are complementary to form a "knob into hole" dimer.

According to a specific aspect, each of the CH3 domains in the Fc region is of the IgG type with the amino acid sequence identified as SEQ ID NO:8 (human wild type IgG1 CH3), or a functional variant of SEQ ID NO:8, which is engineered to obtain a strand-exchange by incorporating at least one beta strand IgA segment of at least 2 amino acids length, and the Fc region preferably comprises a cognate pair of CH3 domains through pairing an IgA segment of the first CH3 domain with an IgA segment of the second CH3 domain. According to a specific example of strand exchanged CH3, a first CH3 domain comprising an AG chain is characterized by the amino acid sequence identified as SEQ ID NO:9; and a matching second CH3 domain comprising a GA chain is characterized by the amino acid sequence identified as SEQ ID NO:10.

Such strand-exchanged CH3 domains specifically may comprise alternating segments of IgA and IgG amino acid sequences, e.g. incorporating at least 1, 2, 3, 4, or 5 different IgA segments, each located at different positions and separated from each other by a non-IgA segment, e.g. IgG segments.

According to a specific aspect, the ABM is an effector-function competent antibody comprising an Fc gamma receptor binding site and/or a C1q binding site, optionally in the Fc region.

Specifically, the antibody is characterized by any of an ADCC and/or CDC activity.

Yet, according to a specifically preferred aspect, the ABM is an effector-negative (EN) antibody comprising an Fc region deficient in binding to an Fc gamma receptor and/or C1q.

Specifically, the antibody is effector deficient (herein also referred to as effector negative), with substantially reduced or no binding to an Fc gamma receptor or CD16a via the Fc region.

Specifically, the effector-negative antibody is characterized by a human IgG2 CH2 sequence, or an engineered variant thereof, comprising a modified human IgG2 CH2 domain (F296A, N297Q) described in U.S. Pat. No. 8,562,986, fused to the N-terminus of the C-terminal CH3 domain (numbering according to EU index of Kabat).

Specifically, the EN antibody has a substantially reduced or no ADCC and/or CDC.

Specifically, the ABM comprises a pH-dependent FcRn binding site located in CH2 and/or CH3 domains, if any. Specifically, the ABM comprises an Fc part of an antibody which comprises an FcRn binding site at the interjunction of the CH2 with the CH3 domain. Specifically, the FcRn binding site has an affinity to bind the FcRn with a KD of less than $10^{-4}$ M, or less than $10^{-5}$ M, $10^{-6}$ M, $10^{-7}$ M, or $10^{-8}$ M in a pH-dependent manner.

Specifically, the binding affinity to bind FcRn in a pH dependent way is at least 1-log, preferably at least 2-log or 3-log increased at pH5-6 as compared to the same binding affinity at physiological pH (pH7.4).

According to a further aspect, the ABM is engineered to alter the pH dependent FcRn binding. For example, at least one human IgG1 CH3 domain is engineered to comprise at least one mutation at the FcRn binding site to reduce pH-dependent FcRn binding, specifically at least one of the H433A or H435A mutations, or both H433A and H435A mutations, wherein the numbering is according to the EU index of Kabat. Reduction of pH-dependent FcRn binding may be such that the binding affinity to bind FcRn in a pH dependent way is less than 1-log, preferably about the same or less at pH5-6 as compared to the same binding affinity at physiological pH (pH7.4).

Specific embodiments refer to any of the ABM exemplified herein, or comprising any of the heavy and light chains or any of the pairs of heavy and light chains described in the Examples section. Specifically, an ABM as described herein may comprise or consist of the heavy and light chains described in the Examples section.

The invention further provides for an ABM conjugate (ABMC) comprising the ABM described herein, and at least one heterologous molecule covalently conjugated to one or both of the cysteines at position 108 and 113 of the CH2 domain, wherein numbering is according to the IMGT. Specifically, the ABMC is a cysteine-linked ADC.

Specifically, the ABM:heterologous molecule (drug) stoichiometry ratio ranges between 1:2-1:4.

Specifically, a conjugation chemistry method commonly used for bioconjugation of drugs to macromolecules by reacting with free cysteines is used. The cysteine residues are specifically alkylated by reacting them with a-haloketones or Michael acceptors, such as maleimide derivates. Specifically, any or each of the free thiol groups of the ABM are reacting to covalently link the heterologous molecule by a reaction called Michael addition. Specifically, a thiol can be reacted with a maleimide group resulting in a thiol-maleimide adduct (Michael adduct).

Suitable methods of conjugating antibodies with one or more drug moieties through reaction with non-cross-linked, highly reactive cysteine amino acids are well-known in the art e.g., is described in U.S. Pat. No. 7,521,541B2.

Specifically, the free cysteine of an ABM is unpaired with another cysteine of the same ABM molecule, thus, is not cross-linked within the ABM, or no part of an ABM intramolecular disulphide bridge.

Specifically, the free cysteine of an ABM is bound to other thiol-bearing molecules (other than the same ABM molecule) e.g., unbound cysteines or glutathione, which may be present after recombinant expression of the ABM in a cell culture. Such thiol binding is understood as "thiol-caps", which would prevent reaction with thiol-reactive agents and are preferably removed by reducing the antibody with reducing agents, such as TCEP (Tris-(2-carboxyethyl)-phosphine).

The term "reducing agent" as used herein refers to a chemical species that provides electrons to another chemical species. Exemplary reducing agents include dithiothreitol (DTT), 2-mercaptoethanol (2-ME), and tris(2-carboxyethyl) phosphine (TCEP) and their related salts (e.g., TCEP-hydrochloride).

Treatment with reducing agents usually reduces the antibody's interchain disulfide bonds. Therefore, a re-oxidation step using oxidizing agents (e.g., dehydroascorbic acid) is preferably following a reduction step. A purification step may be included between the reduction and oxidation steps. The re-oxidized antibody typically comprises the free cysteine(s) which are highly reactive cysteine amino acids.

The term "oxidizing agent" as used herein refers to a compound that causes the conversion of a pair of free thiols to a disulfide bond. Examples of oxidizing agents include e.g., 5,5'-dithiobis(2-nitrobenzoic acid) (DTNB), dehydroascorbic acid (DHAA), and copper sulfate ($CuSO_4$). "A re-oxidation step" is an affirmative step that is taken to cause the conversion of a pair of free thiols to a disulfide bond. Affirmative steps include introduction of an exogenous oxidizing agent and/or an intentional hold period to allow for autoxidation.

As an alternative to thiol-reactive maleimide, a disulfide bridge can be obtained by oxidation of the thiol group of the cysteine with a linker bearing a sulfhydryl group.

1,4-Addition reactions of $\alpha$, $\beta$-unsaturated carbonyl compounds and $\alpha$, $\beta$-unsaturated nitriles with resonance-stabilized carbon nucleophiles, such as enolate ions and enamines, are known as Michael addition. The $\alpha$, $\beta$-unsaturated compound undergoing Michael addition is called the Michael acceptor, the nucleophile Michael donor, and the product Michael adduct.

Therefore, the present invention provides for site-specific conjugation of a heterologous molecule through site-directed mutations of the ABM, by site-specific chemical conjugation, or by genetically engineered sites in the ABM.

According to specific embodiments, the heterologous molecule is a substance suitably used in the diagnosis, cure, mitigation, treatment, or prevention of disease, preferably selected from the group consisting of a pharmaceutical drug substance, toxin, radionuclide, immunomodulator, cytokine, lymphokine, chemokine, growth factor, tumor necrosis factor, hormone, hormone antagonist, enzyme, such as L-Asparaginase, oligonucleotide, DNA, RNA, siRNA, RNAi, microRNA, peptide nucleic acid, photoactive therapeutic agent, anti-angiogenic agent, pro-apoptotic agent, peptide, lipid, carbohydrate, fluorescent tag, visualization peptide, biotin, serum half-life modulator, capture tag, chelating agent, and solid support.

Specifically, the heterologous molecules are any of a dye, radioisotope, or cytotoxin. Particular examples include the conjugation of fluorescent proteins, dyes, or the tethering with functional molecules, e.g. PEGs, porphyrins, peptides, peptide nucleic acids, and drugs.

Specific examples refer to those heterologous molecules which are any artificial or biological chemical compound or molecule which interferes with the physiological function of a cell, e.g. a cancer or tumor cell. Drugs which may be linked to the ABM may include cytostatic agents, or cytotoxic agents. For example, cytostatic agents that may be used for covalent coupling to the ABM include alkylating agents, antimetabolites, antibiotics, mitotic inhibitors, hormones, or hormone antagonists. Alkylating agents may e.g. include Busulfan (Myleran), Carboplatin (Paraplatin), Chlorambucil, Cisplatin, Cyclophosphamide (Cytoxan), Dacarbazine (DTIC-Dome), Estramustine Phosphate, Ifosfamide, Mechlorethamine (Nitrogen Mustard), Melphalan (Phenylalanine Mustard), Procarbazine, Thiotepa, Uracil Mustard, antimetabolites may e.g. include Cladribine, Cytarabine (Cytosine Arabinoside), Floxuridine (FUDR, 5-Fluorodeoxyuridine), Fludarabine, 5-Fluorouracil (5FU), Gemcitabine, Hydroxyurea, 6-Mercaptopurine (6MP), Methotrexate (Amethopterin), 6-Thioguanine, Pentostatin, Pibobroman, Tegafur, Trimetrexate, Glucuronate, antibiotics may e.g. include Aclarubicin, Bleomycin, Dactinomycin (Actinomycin D), Daunorubicin, Doxorubicin (Adriamycin), Epirubicin, Idarubicin, Mitomycin C, Mitoxantrone, Plicamycin (Mithramycin), or mitotic inhibitors may e.g. include Etoposide (VP-16, VePesid), Teniposide (VM-26, Vumon), Vinblastine, Vincristine, Vindesine, hormones, or hormone antagonists which may e.g. be used include Buserelin, Conjugate Equine Estrogen (Premarin), Cortisone, Chlorotriansene (Tace), Dexamethasone (Decadron), Diethylstilbestrol (DES), Ethinyl Estradiol (Estinyl), Fluoxymesterone (Halotestin), Flutamide, Goserelin Acetate (Zoladex), Hydroxyprogesterone Caproate (Delalutin), Leuprolide, Medroxyprogesterone Acetate (Provera), Megestrol Acetate (Megace), Prednisone, Tamoxifen (Nolvadex), Testolactone (Teslac), Testosterone. Cytostatic or antineoplastic compounds such as those disclosed above are known in prior art and may e.g. be found in D. S. Fischer & T. M. Knobf (1989), The cancer chemotherapy handbook (3rd ed.). Chicago:Year Book Medical and Association of Community Cancer Centers (Spring, 1992), Compendia-based drug bulletin, Rockville, Md.

Specifically, the heterologous molecule is conjugated to one or both of the cysteines at position 108 and 113 of the CH2 domain via a conjugation linker, wherein numbering is according to the IMGT. Such conjugation linker is also understood as a spacer, which is coupled to the heterologous molecule. Typically, the linker is covalently attached to the heterologous molecule before reacting with the ABM.

Specifically, the conjugation linker comprises a maleimide group.

Specifically, the conjugation linker is a cleavable or non-cleavable linker. Specifically, the linker is a synthetic or artificial amino acid sequence that connects or links the ABM to the heterologous molecule or drug substance.

Specifically, a cleavable linker is used which is cleaved as a response to physiological stimuli such as low pH, high glutathione concentrations, and/or proteolytic cleavage. Specific cleavable linkers are cleaved by proteases, acids, or by reduction of a disulfide body (e.g. glutathion-mediated or glutathion sensitive). For example, cleavable linkers may comprise valine-citrulline linkers, hydrazone linkers, or disulfide linkers.

Specifically, a non-cleavable linker is used in combination with an internalizing ABM. In such case the ABMC relies on degradation within the lysosome after internalization. Specific non-cleavable linkers comprise maleimidocaproyl linker to MMAF (mc-MMAF), N-maleimidomethylcyclohexane-1-carboxylate (MCC), or mercapto-acetamidocaproyl linkers.

The invention further provides for an expression system comprising one or more nucleic acid molecules encoding the ABM described herein, in particular isolated nucleic acid molecules. Depending on the number of different chains, each composed of an amino acid sequence, one or more encoding nucleic acid molecules may be used in an expression system, which includes one or more expression cassettes comprised in one or more expression vectors.

Specifically, said expression cassette is incorporated in a plasmid comprising or incorporating the nucleic acid described herein, which expression cassette optionally comprises further sequences to express the ABM encoded by the nucleic acid sequence, such as regulatory sequences.

The invention further provides for a host cell comprising the expression system described herein. Specifically, the host cell is a production host cell comprising at least one expression cassette or a plasmid incorporating one or more nucleic acid molecules encoding an ABM described herein.

Specifically, the host cell transiently or stably expresses the ABM. According to specific examples, the host cell is a eukaryotic host cell, preferably any of yeast or mammalian cells.

The invention further provides for a method of producing an ABM described herein, wherein a host cell described herein is cultivated or maintained under conditions to produce said ABM.

Specifically, the ABM may be isolated and/or purified from the cell culture supernatant. According to a specific example, the ABM is a bispecific full-length antibody which is heterodimeric comprising two different HCs and two different LCs, and the ABM comprises a correct pairing of the cognate HC/LC pairs and cognate CL and CH1 domains, respectively, and the ABM is produced by the host cell, wherein less than 10% of the antibodies produced are incorrectly paired, preferably less than 5%, as measured by mass spectrometry (LC-ESI-MS) comparing maximum peak intensity.

Specifically, the ABM or ABMC described herein is provided for medical, diagnostic or analytical use.

Specifically, the ABM or ABMC described herein is provided for use in the treatment of cancer, autoimmune disease or allergy, targeting at least one antigen which is relevant to the disease. Therefore, the invention further refers to a method for treating a subject suffering from cancer, autoimmune disease or allergy, by administering an effective amount of the ABM or ABMC described herein, wherein the ABM or ABMC is targeting at least one antigen which is relevant to the disease.

Specifically, the cancer is selected from the group consisting of breast cancer, prostate cancer, ovarian cancer, cervical cancer, skin cancer, pancreatic cancer, colorectal cancer, metastatic colorectal cancer (mCRC), non-resectable liver metastases, Squamous Cell Carcinoma of the Head and Neck, Non-Small Cell Lung Cancer (NSCLC), and Head and Neck Squamous Cell Carcinoma (HNSCC).

The invention further provides for a pharmaceutical preparation comprising the ABM or ABMC described herein, preferably in a parenteral or mucosal formulation, optionally containing a pharmaceutically acceptable carrier or excipient.

Specifically, the ABM or ABMC described herein is provided in a pharmaceutical preparation comprising a pharmaceutically acceptable carrier or excipient in a parenteral formulation.

The invention further provides for a method of producing an ABMC described herein, comprising the steps:
a) providing an ABM described herein; and
b) reacting at least one thiol group of one or both of the cysteines at positions 108 and 113 of the CH2 domain with a heterologous molecule by a site-specific conjugation method, in particular a chemical conjugation method.

Specifically, said at least one thiol group is reacting with said heterologous molecule by a Michael reaction, using a conjugation linker comprising a maleimide group.

Specifically, said production method does not comprise measures and/or a reaction step of cleaving intramolecular sulfide or disulfide bonds that would otherwise produce free thiol groups, e.g. under reducing conditions. Thus, the preparation of the ABM and/or ABMC under non-reducing conditions is preferred.

Yet, according to a specific aspect, the ABM is pretreated with a reducing agent for reduction, and re-oxidation with an oxidizing agent to prepare the free reactive cysteine(s) of the ABM, ready for conjugation, which can improve the conjugation efficiency.

Unless indicated otherwise, the positions are herein numbered according to the IMGT system (Lefranc et al., 1999, Nucleic Acids Res. 27: 209-212). Yet, in the Examples section, the numbering according to the EU index of Kabat is used. An explanation of the Kabat numbering scheme can be found in Kabat, E A, et al., Sequences of proteins of immunological interest (NIH publication no. 91-3242, 5$^{th}$ edition (1991)). Table 23 indicates correspondence for names and numbers of the mutant proteins, referring to the numbering according to the positions referred to herein according to the EU index of Kabat and the IMGT numbering.

FIGURES

Figure 1:
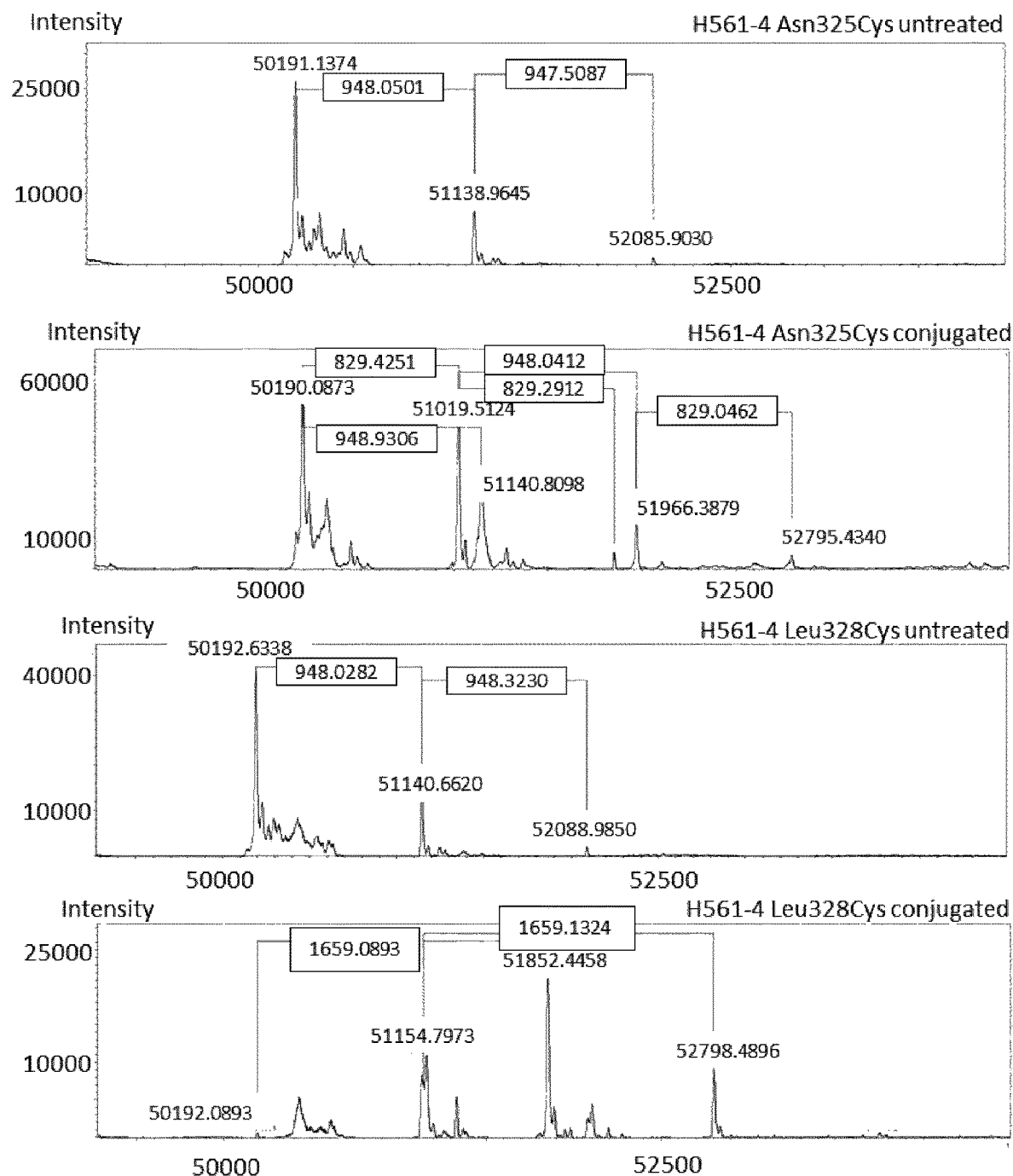

FIG. 1: Mass spectrometry of H561-4 Asn325Cys: The treatment with cysteine-modifying agent caused the shift of the largest peak of approximately 829.5 Da, corresponding to one modified cysteine residue. Mass spectrometry analysis of H561-4 Leu328Cys: The treatment with cysteine-modifying agent caused the shift of the largest peak of approximately 1659 Da, corresponding to two modified cysteine residues.

Figure 2:
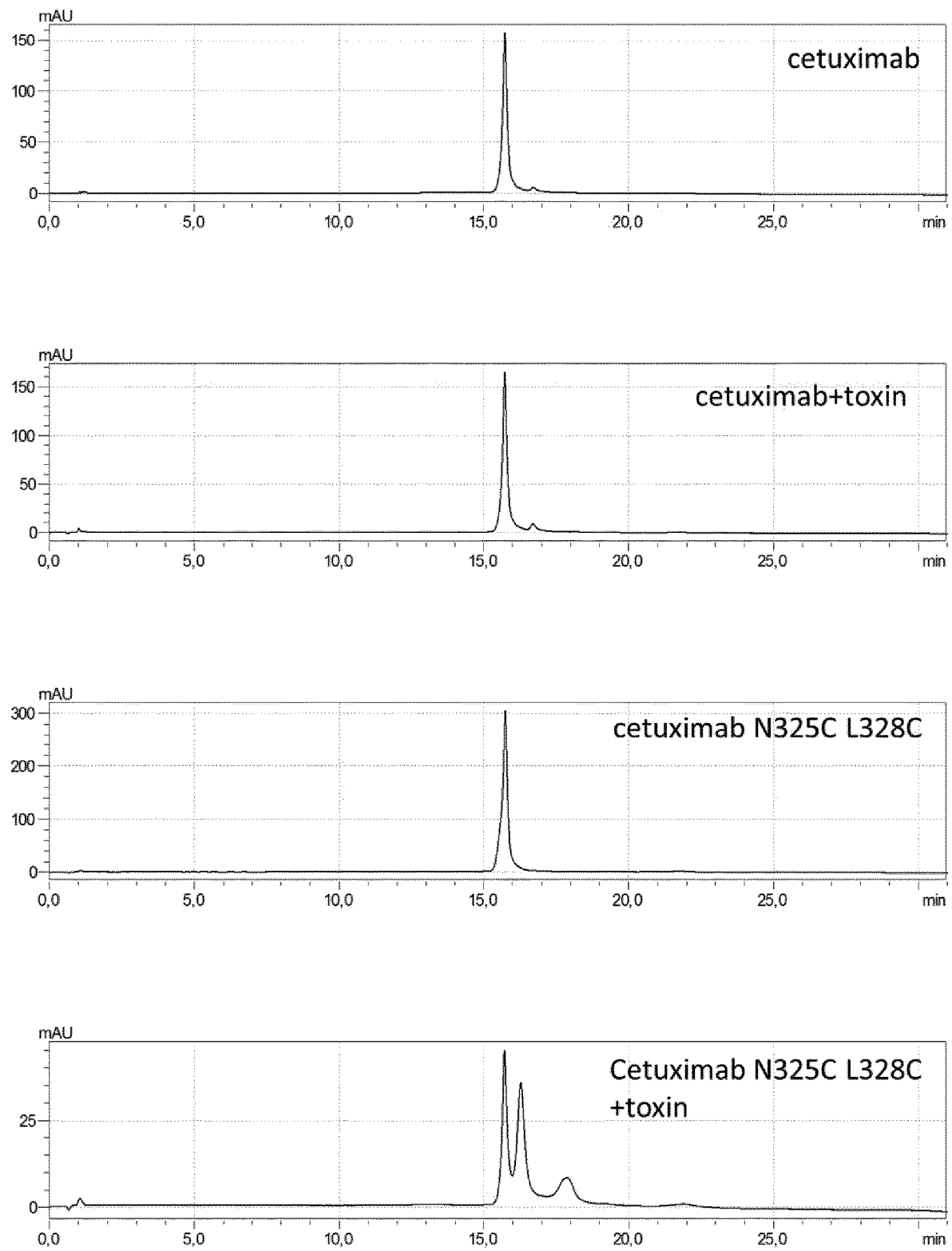

FIG. 2: HIC analysis of double cysteine substituted mutant CX_N325CL328C-mal-val-cit-MMAE.

Figure 3:
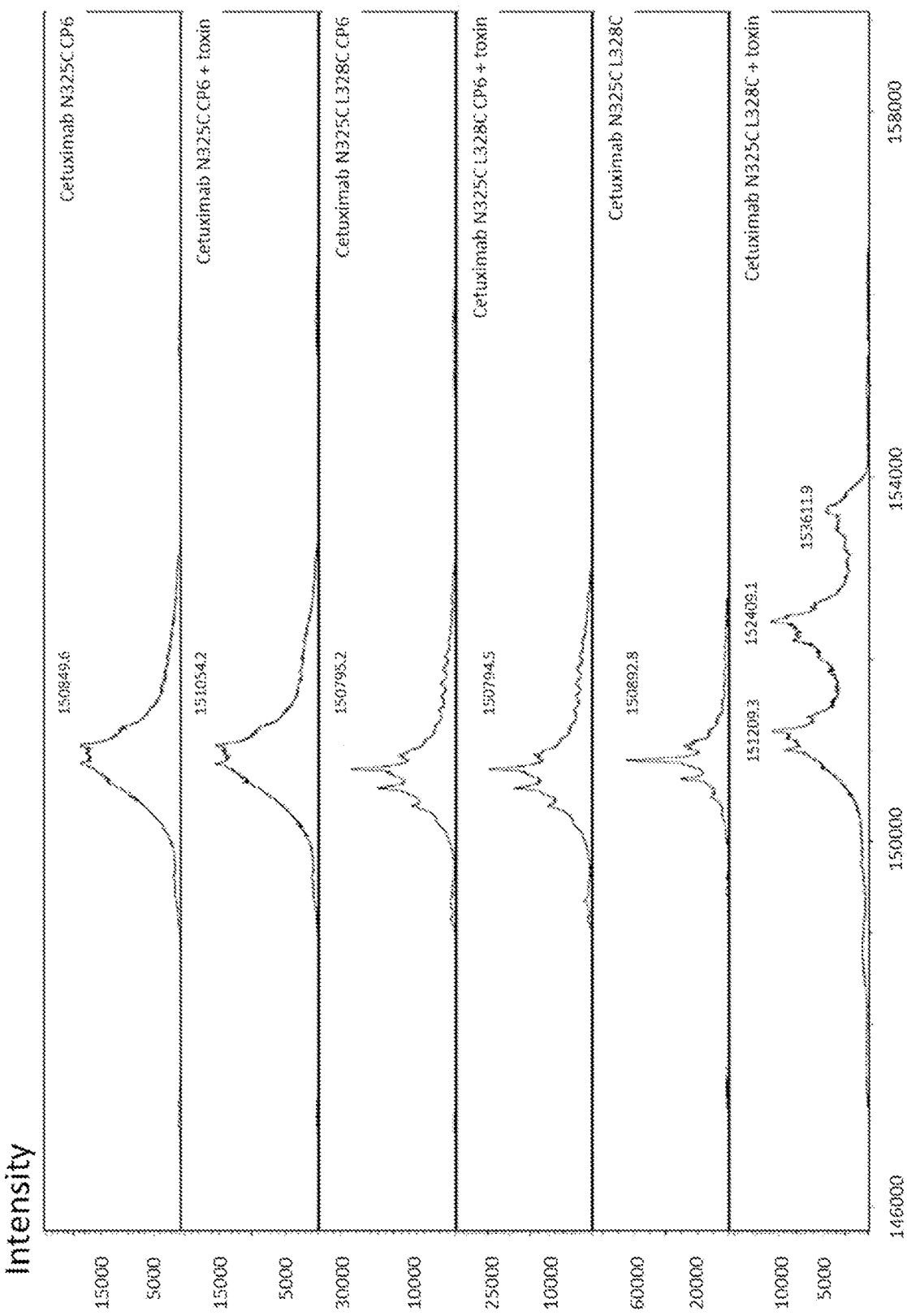

FIG. 3: Mass spectrometry analysis of single and double cysteine substituted mutants.

Figure 4:
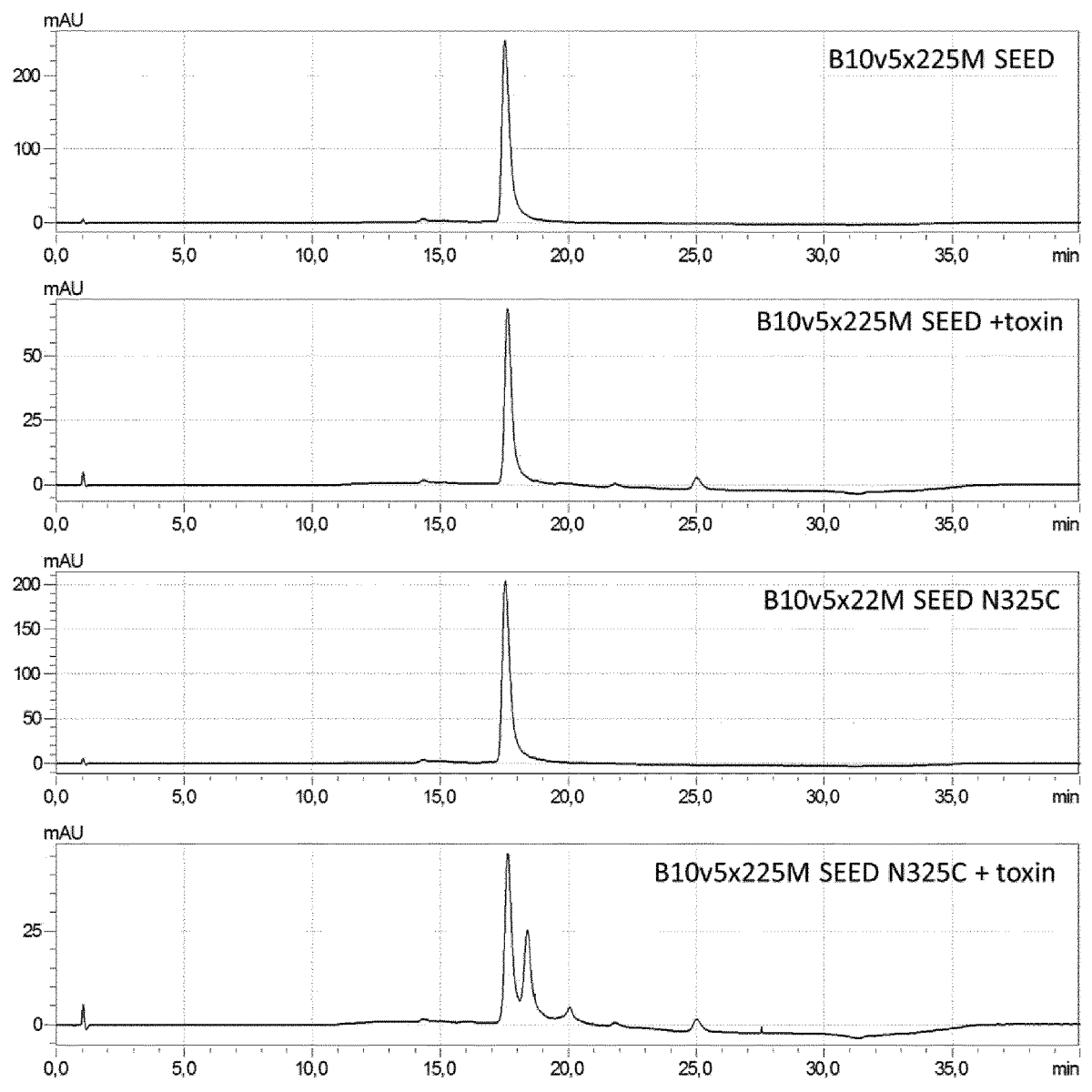

FIG. 4: HIC analysis of B10v5x225M SEED—mal-val-cit-MMAE conjugate.

FIG. 5: Internalization of CX_Alexafluor488 and single cysteine substituted mutants CX_N325C (Asn325Cys) and CX_L328C (Leu328Cys) mutants coupled with maleimide-Alexafluor488 into strongly EGFR-positive A431 and MB-MDA468 cells.

Figure 6:
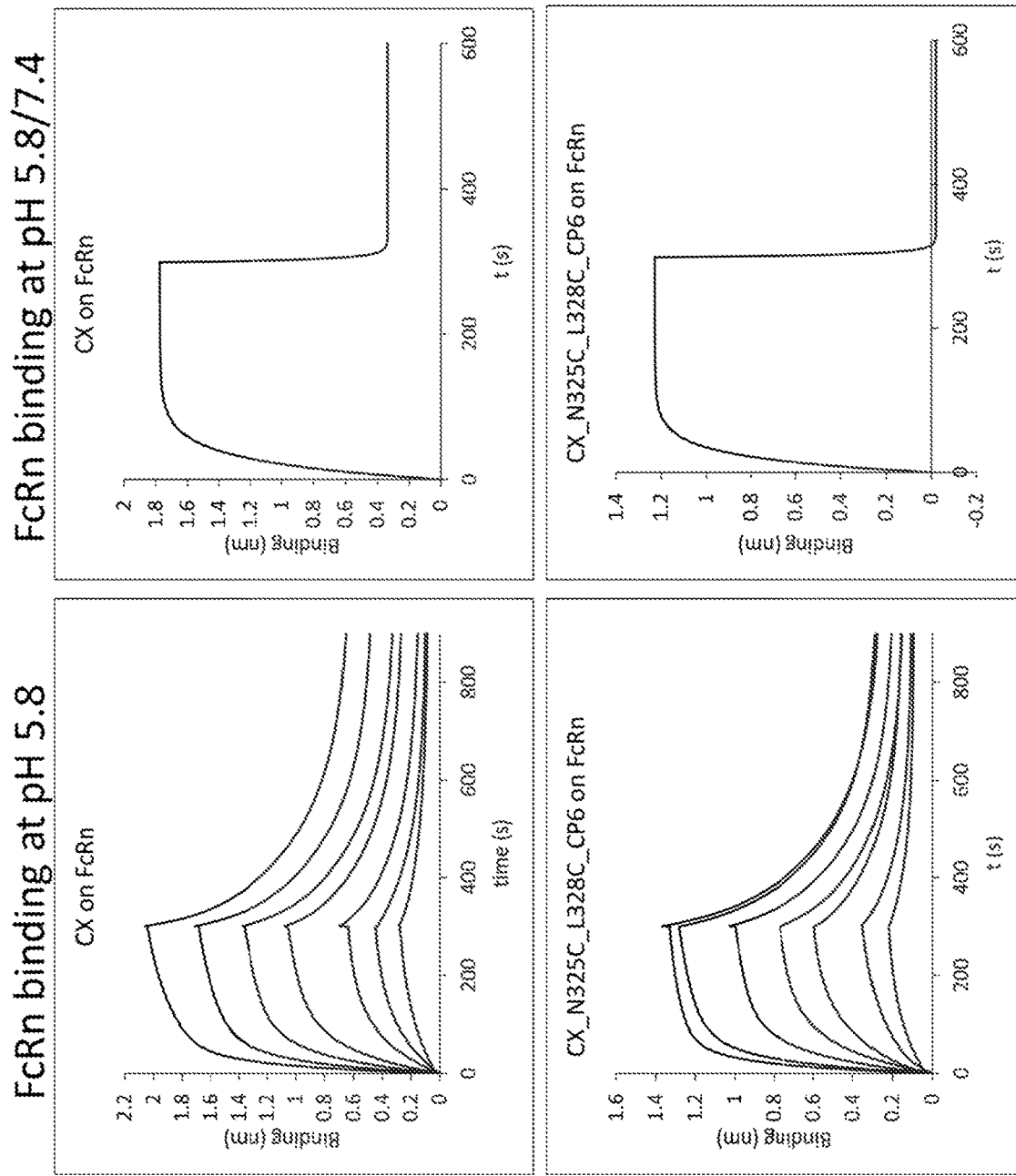

FIG. 6: Binding to FcRn of CX and CX_Asn325CysLeu328Cys_CysP6 at pH 5.8 and with pH shift to 7.4 for dissociation.

FIG. 7: Sequences
SEQ ID NO:1:amino acid sequence of a human CH2 comprising the N325C substitution, wherein numbering is according to the EU index of Kabat;
SEQ ID NO:2:amino acid sequence of a human CH2 comprising the L328C substitution, wherein numbering is according to the EU index of Kabat;
SEQ ID NO:3:amino acid sequence of a human CH2 comprising the N325C and L328C substitution, wherein numbering is according to the EU index of Kabat;
SEQ ID NO:4:amino acid sequence of a human Fc comprising the N325C substitution, wherein numbering is according to the EU index of Kabat;
SEQ ID NO:5:amino acid sequence of a human Fc comprising the L328C substitution, wherein numbering is according to the EU index of Kabat;
SEQ ID NO:6:amino acid sequence of a human CH2 comprising the N325C and L328C substitution, wherein numbering is according to the EU index of Kabat;
SEQ ID NO:7:amino acid sequence of a human IgG1 hinge region
SEQ ID NO:8:amino acid sequence of a human IgG1 CH3
SEQ ID NO:9:amino acid sequence of a human IgG1, which is engineered according to the SEED technology comprising an AG chain;
SEQ ID NO:10:amino acid sequence of a human IgG1, which is engineered according to the SEED technology comprising a GA chain FIG. 8: Evaluation of in vitro cytotoxicity of cetuximab-based ADCs with Mal-Val-Cit-MMAE.

Figure 9:
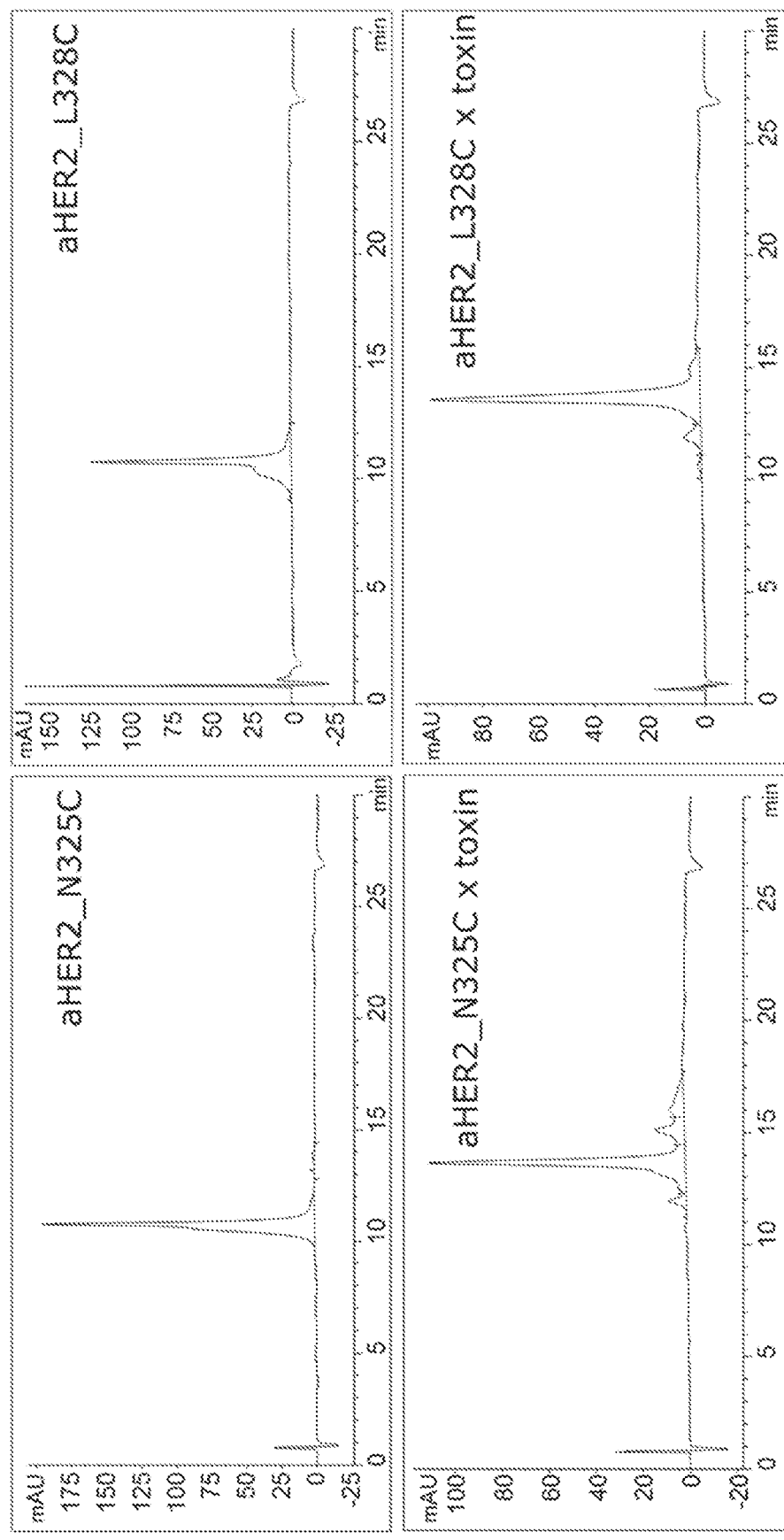

FIG. 9: HIC chromatograms of unconjugated and toxin-conjugated HER2 binding antibodies with cysteine mutations at positions N325 and L328C.

DETAILED DESCRIPTION

Specific terms as used throughout the specification have the following meaning.

The term "antigen-binding molecule" or ABM as used herein shall mean a molecule comprising an antigen-binding moiety capable of specifically recognizing an antigen or epitope thereof with a certain binding affinity and/or avidity, herein also referred to as "binding domain". According to specific examples of an ABM, the binding domain is an immunoglobulin-type binding region or one or more (e.g. 2) antibody domains comprising an antigen-binding site in CDR-loops or in non-CDR (or structural) loops, and in particular an antigen-binding moiety comprised in any of a single-domain antibody, single-chain variable domains (VH/VL), Fd, Fab, F(ab')$_2$, scFv, Fd, Fv, an antigen-binding CH3, Fcab, mAb$^2$, Armadillo repeat polypeptide, fibronectin type III domain, tenascin type III domain, ankyrin repeat motif domain, lipocalin, Kunitz domain, Fyn-derived SH2 domain, miniprotein, C-type lectin-like domain scaffold, engineered antibody mimic, and any genetically manipulated counterparts of any of the foregoing which retain antigen binding functionality.

Specific embodiments of an ABM comprise or consist of an antibody or antigen-binding fragment thereof.

The term "antibody" as used herein is defined as antigen-binding polypeptides that are either immunoglobulins or immunoglobulin-like molecules, or other proteins exhibiting modular antibody formats, e.g. composed of one or more antibody domains and bearing antigen-binding properties similar to immunoglobulins or antibodies, in particular proteins that may exhibit mono- or bi- or multi-specific, or mono-, bi- or multivalent binding properties, e.g. at least two specific binding sites for epitopes of e.g. antigens, effector molecules or structures, specifically of pathogen origin or of human structure, like self-antigens including cell-associated or serum proteins. The terms "antibody" and "immunoglobulin" are herein used interchangeably.

An antibody typically consists of or comprises antibody domains, which are understood as constant and/or variable domains of the heavy and/or light chains of immunoglobulins, with one or more or without a linker sequence. Antibodies are specifically understood to consist of or comprise combinations of variable and/or constant antibody domains with or without a linking sequence or hinge region, including pairs of variable antibody domains, such as one or two VH/VL pairs. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The term "antibody" as used herein specifically includes full-length antibodies, including antibodies of immunoglobulin-like structures. Specifically, an antibody can be a full-length antibody, e.g. of an IgG type (e.g., an IgG1, IgG2, IgG3, or IgG4 subtype), IgA1, IgA2, IgD, IgE, or IgM antibody. Typically, an antibody having an antigen-binding site through a specific CDR structure is able to bind a target antigen through the CDR loops of a pair of VH/VL domains.

The term "antibody" further includes any of derivatives, combinations or fusions of antibodies, antibody domains, or antibody fragments.

The term "full length antibody" is used to refer to any antibody molecule comprising an Fc region or at least most of the Fc part of an antibody, which specifically includes a dimer of heavy chains. A full-length antibody can be monospecific or multispecific e.g., bispecific, such as a bispecific $mAb^2$. This term "full length antibody" is used herein to emphasize that a particular antibody molecule is not an antibody fragment.

In accordance therewith, an antibody is typically understood as a protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as immunoglobulin variable region genes. Light chains (LC) are classified as either kappa (including a VL and a Ckappa domain) or lambda (including a VL and a C lambda domain). Heavy chains (HC) are classified as gamma, mu, alpha, delta, or epsilon, which in turn define the immunoglobulin classes, IgG, IgM, IgA, IgD and IgE, respectively.

The term "antibody" shall specifically include antibodies in the isolated form, which are substantially free of other antibodies directed against different target antigens and/or comprising a different structural arrangement of antibody domains. Still, an isolated antibody may be comprised in a combination preparation, containing a combination of the isolated antibody, e.g. with at least one other antibody, such as monoclonal antibodies or antibody fragments having different specificities.

The term "antibody" shall apply to antibodies of animal origin, including human species, such as mammalian, including human, murine, rabbit, goat, camelid, llama, cow and horse, or avian, such as hen, which term shall particularly include recombinant antibodies which are based on a sequence of animal origin, e.g. human sequences.

The term "antibody" specifically applies to human antibodies.

The term "human" as used with respect to an antibody is understood to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

A human antibody is preferably selected or derived from the group consisting of IgA1, IgA2, IgD, IgE, IgG1, IgG2, IgG3, IgG4 and IgM.

A murine antibody is preferably selected or derived from the group consisting of IgA, IgD, IgE, IgG1, IgG2A, IgG2B, IgG2C, IgG3 and IgM.

The term "antibody" further applies to chimeric antibodies, e.g. chimeric antibodies, with sequences of origin of different species, such as sequences of murine and human origin.

The term "chimeric" as used with respect to an antibody refers to those molecules wherein one portion of each of the amino acid sequences of heavy and light chains is homologous to corresponding sequences in immunoglobulins derived from a particular species or belonging to a particular class, while the remaining segment of the chain is homologous to corresponding sequences in another species or class. Typically the variable region of both light and heavy chains mimics the variable regions of immunoglobulins derived from one species of mammals, while the constant portions are homologous to sequences of immunoglobulins derived from another. For example, the variable region can be derived from presently known sources using readily available B-cells or hybridomas from non-human host organisms in combination with constant regions derived from, for example, human cell preparations.

The term "antibody" may further apply to humanized antibodies.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized immunoglobulins preserve all CDR sequences (for example a humanized mouse antibody which contains all six CDRs from the mouse antibody). Other forms have one or more CDRs which are altered with respect to the original antibody.

According to a specific embodiment, all antibody domains comprised in the ABM as described herein are of human origin or humanized or functionally active variants thereof with at least 60% sequence identity, or at least 70%, 80%, 90%, or 95% sequence identity, preferably wherein the origin of the antibody domains is any of an IgG1, IgG2, IgG3, IgG4, IgA, IgM, or IgE antibody. Specifically, all antibody domains originate from the same basic immunoglobulin fold, although b-sheet formats may differ, and connecting loops certainly be variable, especially in V domains.

The term "antibody" further applies to monoclonal or polyclonal antibodies, specifically a recombinant antibody, which term includes all antibodies and antibody structures that are prepared, expressed, created or isolated by recombinant means, such as antibodies originating from animals, e.g. mammalian species including humans, that comprise genes or sequences from different origin, e.g. chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

The term "antibody" is understood to include functionally active variants of new or existing, e.g. naturally-occurring antibodies.

It is further understood that the term variant of an ABM or antibody, in particular variants of antibody-like molecules, or antibody variants, shall also include derivatives of such molecules as well.

A derivative is any combination of one or more ABM and or a fusion protein in which any domain or minidomain of the ABM may be fused at any position to one or more other proteins, such as to other ABM e.g., antibodies or antibody fragments, but also to ligands, enzymes, toxins and the like.

The ABM or ABMC described herein can specifically be used as isolated polypeptides or as combination molecules, e.g. through recombination, fusion or conjugation techniques, with other peptides or polypeptides. The peptides are preferably homologous to antibody domain sequences, and are preferably at least 5 amino acids long, more preferably at least 10 or even at least 50 or 100 amino acids long, and constitute at least partially the loop region of the antibody domain.

A derivative of an ABM or antibody may also be obtained by association or binding to other substances by various chemical techniques such as covalent coupling, electrostatic interaction, di-sulphide bonding etc. The other substances bound to the antibodies may be lipids, carbohydrates, nucleic acids, organic and inorganic molecules or any combination thereof (e.g. PEG, prodrugs or drugs). A derivative would also comprise an ABM or antibody with the same amino acid sequence but made completely or partly from non-natural or chemically modified amino acids. In a specific embodiment, the ABM is a derivative comprising an additional tag allowing specific interaction with a biologically acceptable compound. There is not a specific limitation with respect to the tag usable, as far as it has no or tolerable negative impact on the binding of the antibody to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the ABM so as to generate a "labelled" ABM. The label may be detectable by itself, e.g. radioisotope labels or fluorescent labels, or, in the case of an enzymatic label, may catalyze chemical alteration of a substrate compound or composition which is detectable.

A derivative of an ABM or antibody is e.g. derived from a parent ABM and antibody sequence, respectively, such as a parent antigen-binding (e.g. CDR) or framework (FR) sequence, e.g. mutants or variants obtained by e.g. in silico or recombinant engineering or else by chemical derivatization or synthesis.

The term "variants" as used herein shall specifically include any "mutant", "homolog", or "derivative" as described herein. The term "variant" shall specifically encompass functionally active variants which are characterized by a certain functionality.

The functionality of the ABM or the antibody described herein is particularly characterized by a certain antigen-binding property (in particular the epitope specificity) and the free thiol group of the cysteines engineered into the CH2 domain, as further described herein.

The term "variant" shall particularly refer to antibodies, such as mutant antibodies or fragments of ABM or antibodies, e.g. obtained by mutagenesis methods, in particular to delete, exchange, introduce inserts into a specific antibody amino acid sequence or region or chemically derivatise an amino acid sequence, e.g. in the constant domains to engineer the antibody stability, effector function or half-life, or in the variable domains to improve antigen-binding properties, e.g. by affinity maturation techniques available in the art. Any of the known mutagenesis methods may be employed, including point mutations at desired positions, e.g. obtained by randomization techniques. In some cases, positions are chosen randomly, e.g. with either any of the possible amino acids or a selection of preferred amino acids to randomize the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "functional variants" herein also referred to as "functionally active variant" may e.g. include a sequence resulting from modification of a parent sequence (e.g. from a parent ABM or antibody) by insertion, deletion or substitution of one or more amino acids, or chemical derivatization of one or more amino acid residues in the amino acid sequence, or nucleotides within the nucleotide sequence, or at either or both of the distal ends of the sequence, e.g. in a CDR or FR sequence, and which modification does not affect, in particular impair, the activity of this sequence. In the case of a binding site having specificity to a selected target antigen, the functionally active variant of an antibody would still have the predetermined binding specificity, though this could be changed, e.g. to change the fine specificity to a specific epitope, the affinity, the avidity, the Kon or Koff rate, etc. For example, an affinity matured antibody is specifically understood as a functionally active variant antibody. Hence, the modified CDR sequence in an affinity matured antibody is understood as a functionally active variant.

The functional activity is preferably determined by the structure and function of the variant as compared to a parent molecule, e.g. in an assay for determining the specificity of binding a target antigen and/or the required in vivo half-life of the molecule and/or the FcRn binding in a pH dependent way, e.g., determined in a standard assay by measuring functionality of the antibody.

The functional activity of an ABM in terms of antigen-binding is typically determined in an ELISA assay, BIAcore assay, Octet BLI assay, or FACS based assay when the antigen is expressed on cell surface.

Functionally active variants may be obtained, e.g. by changing the sequence of a parent ABM, e.g. a monoclonal antibody having a specific native structure of an antibody, such as an IgG1 structure, to obtain a variant having the same specificity in recognizing a target antigen, but having a structure which differs from the parent structure, e.g. to modify any of the antibody domains to introduce specific mutations, to produce bispecific constructs, or to produce a fragment of the parent molecule.

Typically, a parent ABM or sequence may be modified to produce variants which incorporate mutations within a sequence region besides the antigen-binding site, or within the binding site, that does not impair the antigen binding, and preferably would have a biological activity similar to the parent ABM, including the ability to bind an antigen, e.g. with substantially the same biological activity, as determined by a specific binding assay or functional test to target the antigen.

The term "substantially the same biological activity" as used herein refers to the activity as indicated by substantially the same activity being at least 20%, at least 50%, at least 75%, at least 90%, e.g. at least 100%, or at least 125%, or at least 150%, or at least 175%, or e.g. up to 200% of the activity as determined for the comparable or parent ABM.

The preferred variants as described herein are functionally active with regard to the antigen binding, preferably which have a potency to specifically bind the individual antigen, and not significantly binding to other antigens that are not target antigens, e.g. with a Kd value difference of at least 2 logs, preferably at least 3 logs. The antigen binding by a functionally active variant is typically not impaired, corresponding to about substantially the same binding affinity as the parent ABM or sequence, or ABM comprising a sequence variant, e.g. with a Kd value difference of less than 2 logs, preferably less than 3 logs, however, with the possibility of even improved affinity, e.g. with a Kd value difference of at least 1 log, preferably at least 2 logs.

In a preferred embodiment the functionally active variant of a parent ABM a) is a biologically active fragment of the ABM, the fragment comprising at least 50% of the sequence of the molecule, preferably at least 60%, at least 70%, at least 80%, at least 90%, or at least 95% and most preferably at least 97%, 98% or 99%;

b) is derived from the ABM by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the ABM or a functionally active variant thereof and additionally at least one amino acid or nucleotide heterologous to the polypeptide or the nucleotide sequence.

In one embodiment, the functionally active variant of the ABM as described herein is essentially identical to a variant described above, but differs from its polypeptide or the encoding nucleotide sequence, respectively, in that it is derived from a homologous sequence of a different species. These are referred to as naturally occurring variants or analogs.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains or improves a function of the unaltered polypeptide or the nucleotide sequence, when used as described herein. Such sequence alterations can include, but are not limited to, (conservative) substitutions, additions, deletions, mutations and insertions.

Specific functionally active variants are CDR variants. A CDR variant includes an amino acid sequence modified by at least one amino acid in the CDR region, wherein said modification can be a chemical or a partial alteration of the amino acid sequence, which modification permits the variant to retain the biological characteristics of the unmodified sequence. A partial alteration of the CDR amino acid sequence may be by deletion or substitution of one to several amino acids, e.g. 1, 2, 3, 4 or 5 amino acids, or by addition or insertion of one to several amino acids, e.g. 1, 2, 3, 4 or 5 amino acids, or by a chemical derivatization of one to several amino acids, e.g. 1, 2, 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

The cysteines engineered into the positions 108 and/or 113 of the CH2 domain as further described herein, are typically obtained by site-directed point mutation(s) resulting in a substitution of the naturally-occurring amino acid residue for a cysteine residue.

Besides such point mutations, the ABM may further contain point mutations such as for introducing one or more further cysteine or lysine residues at different predetermined positions, which can be used for conjugating further heterologous molecules. According to a specific embodiment, the ABM described herein is engineered for such point mutations which do not change the number and types of glycosylation sites.

Variants of the ABM as described herein may include point mutations which refer to the exchange of amino acids of the same polarity and/or charge. In this regard, amino acids refer to 20 naturally-occurring amino acids encoded by sixty-four triplet codons. These 20 amino acids can be split into those that have neutral charges, positive charges, and negative charges:

The 20 naturally-occurring amino acids are shown in the table below along with their respective three-letter and single-letter code and polarity:

| Amino-acid name | 3-letter code | 1-letter code | Properties |
| --- | --- | --- | --- |
| Alanine | Ala | A | Non-polar; Hydrophobic |
| Arginine | Arg | R | Positively charged (basic amino acids; non-acidic amino acids); Polar; Hydrophilic; pK = 12.5 |
| Asparagine | Asn | N | No charge (non-acidic amino acids); Polar; Hydrophilic |
| Aspartate | Asp | D | Negatively charged (acidic amino acids); Polar; Hydrophilic; pK = 3.9 |
| Cysteine | Cys | C | No charge (non-acidic amino acids); Non-polar; Hydrophilic |
| Glutamate | Glu | E | Negatively charged (acidic amino acids); Polar; Hydrophilic; pK = 4.2 |
| Glutamine | Gln | Q | No charge (non-acidic amino acids); Polar; Hydrophilic |
| Glycine | Gly | G | No charge (non-acidic amino acids); Non-polar; Hydrophilic |
| Histidine | His | H | Positively charged (basic amino acids; non-acidic amino acids); Polar; Hydrophilic; pK = 6.0 |
| Isoleucine | Ile | I | Non-polar; Hydrophobic |
| Leucine | Leu | L | Non-polar; Hydrophobic |
| Lysine | Lys | K | Positively charged (basic amino acids; non-acidic amino acids); Polar; Hydrophilic; pK = 10.5 |
| Methionine | Met | M | Non-polar; Hydrophobic |
| Phenylalanine | Phe | F | Non-polar; Hydrophobic |
| Proline | Pro | P | Non-polar; Hydrophobic |
| Serine | Ser | S | No charge (non-acidic amino acids); Polar; Hydrophilic |
| Threonine | Thr | T | No charge (non-acidic amino acids); Polar; Hydrophilic |
| Tryptophan | Trp | W | No charge; Non-polar; Hydrophobic |
| Tyrosine | Tyr | Y | No charge (non-acidic amino acids); Polar; Hydrophilic |
| Valine | Val | V | Non-polar; Hydrophobic |

"Percent (%) amino acid sequence identity" with respect to polypeptide sequences is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An ABM variant is specifically understood to include homologs, analogs, fragments, modifications or variants with a specific glycosylation pattern, e.g. produced by glycoengineering, which are functional and may serve as functional equivalents, e.g. binding to the specific targets and with functional properties. An ABM may be glycosylated or unglycosylated. For example, a recombinant ABM as described herein may be expressed in an appropriate mammalian cell to allow a specific glycosylation of the molecule as determined by the host cell expressing the ABM.

The term "beta-sheet" or "beta strand" of an antibody domain, in particular of a constant antibody domain such as a CL or CH1 domain is herein understood in the following way. An antibody domain typically consists of at least two beta strands connected laterally by at least two or three backbone hydrogen bonds, forming a generally twisted, pleated sheet. A beta strand is a single continuous stretch of amino acids of typically 3 to 10 amino acids length adopting such an extended conformation and involved in backbone hydrogen bonds to at least one other strand, so that they form a beta sheet. In the beta sheet, the majority of beta strands are arranged adjacent to other strands and form an extensive hydrogen bond network with their neighbors in which the N—H groups in the backbone of one strand establish hydrogen bonds with the C=O groups in the backbone of the adjacent strands.

The structure of antibody constant domains, such as CH2 or CH3 domains, is similar to that of variable domains, consisting of beta-strands connected by loops, some of which contain short alpha-helical stretches. The framework is mostly rigid and the loops are comparatively more flexible, as can be seen from the b-factors of various Fc crystal structures. An antibody CH2 or CH3 domain typically has seven beta strands forming a beta-sheet (A-B-C-D-E-F-G), wherein the beta strands are linked via loops, three loops being located at the N-terminal tip of the domain (A-B, C-D, E-F), and further three loops being located at the N-terminal tip of the domain (B-C, D-E, F-G). A "loop region" of a domain refers to the portion of the protein located between regions of beta strands (for example, each of the CL or CH1 domains comprises seven beta sheets, A to G, oriented from the N- to C-terminus).

The Fv part of an antibody is typically understood as the pair of VL and VH domains that produces a (hetero)dimer by connecting a binding surface involving the C, C' and F strands of each of the domains (the binding interface). By such contact of the beta-sheet region of the VL domain with the beta-sheet region of the VH domain, a dimer (designated as VL/VH) is produced.

A Fab arm is herein understood as the pair of a first and a second antibody chain, wherein the first chain comprises or consists of a VL domain and a CL domain, which is linked to the C-terminus of the VL domain (light chain, LC), and the second chain comprises or consists of a VH domain and a CH1 domain, which is linked to the C-terminus of the VH domain (heavy chain, HC), wherein the VL connects to (pairs with) the VH via the binding interface, and the CL connects to (pairs with) the CH1 via the binding interface, thereby producing a (hetero)dimer of the LC and HC (also designated LC/HC).

The Fc part of an antibody is herein understood as the pair of antibody chains, each comprising a CH2 domain and a CH3 domain, which is linked to the C-terminus of the CH2 domain (Fc chains), wherein the CH2 domains of each of the antibody chains connect to each other via the binding surface involving the A, B and/or E strands of each of the CH2 domains (the binding interface), and wherein the CH3 domains of each of the antibody chains connect to (pair with) each other via the binding surface involving the A, B and/or E strands of each of the CH3 domains (the binding interface), thereby producing a (homo)dimer of Fc chains. The Fc described herein can be from an IgG, IgA, IgD, IgE or IgM.

In one embodiment described herein, the Fc comprises mutated CH3 domains that comprise an antigen-binding site in the structural loops. Such Fc is understood as antigen-binding Fc and can be used as an ABM as such, or can be part of an ABM, e.g., part of a full-length antibody comprising the antigen-binding Fc instead of an Fc that does not comprise an antigen-binding site in the structural loops.

In one embodiment described herein, the Fc comprises mutated CH3 domains, e.g. which have at least a portion of one or more beta strands replaced with heterologous sequences, such as to include one or more point mutations, or knob or hole mutations. In such case the Fc region comprises a heterodimer of the Fc chains, characterized by the assembly of two different CH3 domains.

Specific knob mutations are one or more amino acid substitutions to increase the contact surface between two domains by incorporating one or more amino acids which provide for an additional protuberance of a beta-strand structure, e.g. one or more of CH3 knob mutations selected from the group consisting of T366Y, T366W, T394W, F405A. A specific knob modification denotes the mutation T366W in the CH3 domain of an antibody (numbering according to EU index of Kabat). Knob mutations specifically provide a matching (cognate) surface to bind another antibody domain, e.g. which is modified to incorporate hole mutations.

Specific hole mutations are one or more amino acid substitutions to increase the contact surface between two domains by incorporating one or more amino acids which provide for an additional cave of a beta-strand structure, e.g. one or more of CH3 hole mutations selected from the group consisting T366S, L368A and Y407V (numbering according to EU index of Kabat). A specific hole-modification denotes any of the mutations T366S, L368A, Y407V, Y407T in the CH3 domain of an antibody (numbering according to EU index of Kabat). Hole mutations specifically provide a matching (cognate) surface to bind another antibody domain, e.g. which is modified to incorporate knob mutations.

Matching knob into hole mutations are, e.g. T366Y on one CH3 domain and the matching Y407'T on the second CH3 domain of the CH3 domain pair, herein referred to as T366Y/Y407'T. Further matching mutations are
T366Y/Y407'T,
F405A/T394'W,
T366Y: F405A/T394'W:Y407'T,
T366W/Y407'A, and/or
S354C:T366W/Y349'C:T366'S:L368'A:Y407V.
(numbering according to EU index of Kabat)

Specific CH3 mutations include an intermolecular beta-strand swap, e.g. wherein one or more segments or sequences within a CH3 beta strand are mutated to incorporate segments or sequences of antibody domains which differ from the original CH3 domain, e.g. of antibody domains of a different type or subtype. Specific mutants are obtained by strand exchange, wherein a CH3 domain of an IgG type incorporates one or more segments or sequences of a CH3 domain of an IgA type. If two strand exchanged CH3 domains are mutated to form a cognate pair, the IgA segments or sequences of each of the CH3 domains produce an interdomain contact surface which is cognate, such that the mutated CH3 domains preferentially pair with each other over a wild-type CH3 domain. Specific examples of such modifications of antibody domains to incorporate a segment swap may be strand-exchange engineered domains (SEED). Such modifications may be used to produce asymmetric or bispecific antibodies by preferentially pairing the SEED modified CH3 domains of the heavy chains. This is based on exchanging structurally related sequences within the conserved CH3 domains. Alternating sequences from human IgA and IgG in the SEED CH3 domains generate two asymmetric but complementary domains, designated AG and GA. The SEED design allows efficient generation of AG/GA heterodimers, while disfavoring homodimerization of AG and GA SEED CH3 domains.

The connection of antibody domains or LC/HC, or Fc chains may be further supported by intradomain or interdomain disulfide bridges. Disulfide bonds are usually formed from the oxidation of thiol groups of two cysteines, thereby linking the S-atoms to form a disulfide bridge between the two cysteine residues.

According to a specific embodiment, antibody domains include mutations incorporating cysteine residues which are capable of forming disulfide bridges to stabilize an antibody domain by an additional intradomain disulfide bridge, or a pair of antibody domains by an additional interdomain disulfide bridge. Specifically, cysteine may be inserted (by an additional amino acid or an amino acid substitution) in the C-terminal region or at the C-terminus of a CH3 domain. A pair of CH3 that bears an additional cysteine modification can be stabilized by disulfide bond formation between the CH3 pair, thereby producing a CH3/CH3 dimer. In some embodiments disulfide-linked antibody domains are homodimers or heterodimers, thus, pairs of the same or different domains.

In order to allow proper pairing of antibody chains or domains, any of the CH3 mutations may specifically be employed, e.g. the knobs-into-holes technology, the SEED technology, charge repulsion technology, disulfide linkage or the cross-mAb technology can be used in order to reduce the amount of not correctly associated molecules.

A "pair" of antibody domains is herein understood as a set of two antibody domains, where one has an area on its surface or in a cavity that specifically binds to, and is therefore complementary to, an area on the other one. Antibody domains may associate and assemble to form a pair of antibody domains through contact of a beta-sheet region. Such domain pair is also referred to as a dimer, which is e.g. associated by electrostatic interaction, recombinant fusion or covalent linkage, placing two domains in direct physical association, e.g. including both in solid and in liquid form. Specifically described herein is a CL/CH1 dimer which can be a preferred pair of cognate antibody domains through certain point mutations at positions identified herein.

In a pair of antibody domains the antibody domains are herein referred to as "counterpart" domains. In an antibody described herein the following domains are considered counterparts suitably forming a pair of antibody domains (counterparts separated by a slash (/)):
VL/VH;
CL (Clambda or Ckappa)/CH1;
CH2/CH2;
CH3/CH3.

The term "multivalent" with respect to an ABM as described herein shall refer to a molecule having at least two binding sites to bind the same target antigen, specifically binding the same or different epitopes of such target antigen. The term shall include bivalent antibodies or molecules with 2 or more valencies to bind the target antigen, e.g. through at least 2, 3, 4 or even more binding sites. For example, a bivalent antibody may have two antigen-binding sites through two pairs of VH/VL domains, both binding the same target antigen.

The term "multispecific" with respect to an ABM as described herein shall refer to a molecule having at least two binding sites specifically binding at least two different target antigens. The term shall include bispecific antibodies or molecules with 2 or more specificities to bind more than one target antigen, e.g. through at least 2, 3, 4 or even more binding sites.

For example, a bispecific antibody may bind one target antigen through a first pair of VH/VL domains (first Fv region), and another target antigen by a second pair of VH/VL domains (second Fv region). A bispecific antibody typically is composed of four different antibody chains, i.e. two HCs and two LCs, such that two different CDR binding sites are formed by heterodimerization (pairing) of a first HC with a first LC and a second HC with a second LC.

In another example, a bispecific antibody may bind by one target antigen one or more antigen-binding sites in CDR loops of antibody variable domains, and another target antigen by one or more antigen-binding sites in non-CDR loops (herein referred to as "structural loops") of antibody constant domains.

The term "ABM conjugate" or "ABMC" as used herein shall refer to a conjugate of an ABM with one or more heterologous molecules, wherein conjugation is by any suitable method of covalently coupling the heterologous molecule(s) e.g., by chemical or enzymatic linkage.

The term "heterologous" as used herein with respect to a heterologous molecule, which is conjugated to an ABM, shall refer to any substance molecule or molecule complex, which is not naturally-occurring in conjunction with the ABM. The heterologous molecule is in particular an artificial substance, or a non-human or non-mammalian biological substance. Exemplary heterologous molecules are drugs or toxins with a biological activity on a target cell.

Typically a heterologous molecule is derivatized to include a conjugation linker and/or a reactive group, which is capable of reacting with one or more free thiol groups of an ABM.

The term "antigen" or "target" as used herein shall in particular include all antigens and target molecules capable of being recognised by a binding site of an antibody (also referred to as paratope). Specifically preferred antigens as targeted by the binding molecule as described herein are those antigens, which have already been proven to be or are capable of being immunologically or therapeutically relevant, especially those, for which a clinical efficacy has been tested. The term "target" or "antigen" as used herein shall in particular comprise molecules selected from the group consisting of (human or other animal) tumor associated receptors and soluble tumor associated antigens, which are self-antigens, such as receptors located on the surface of tumor cells or cytokines or growth factors that are abundantly present in the circulation of cancer patients and associated with such tumor. Further antigens may be of pathogen origin, e.g. microbial or viral pathogens.

The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope), which are immunologically relevant, i.e., are also recognisable by natural or monoclonal antibodies. The term "epitope" as used herein shall in particular refer to a molecular structure which may completely make up a specific binding partner or be part of a specific binding partner to a binding site of an ABM as described herein. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably 8 to 50 amino acids, and more preferably between about 10-20 amino acids in the peptide. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

Specific embodiments refer to naturally-occurring antigens or epitopes, or synthetic (artificial) antigens of epitopes. Artificial antigens which are derivatives of naturally-occurring antigens may have the advantage of an increased antigenicity or stability, which is relevant for being recognized as a binding partner for the specific ABM.

As used herein, the term "specificity" or "specific binding" refers to a binding reaction which is determinative of the cognate ligand of interest in a heterogeneous population of molecules. Thus, under designated conditions (e.g. immunoassay conditions), the ABM described herein binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred at least 1000 fold.

The term "antigen-binding moiety" as used herein refers to molecules (e.g. one peptide or polypeptide, such as an antibody domain) or an association of molecules (e.g., a peptide or polypeptide dimer, such as an antibody Fv), with varying structures capable of binding interactions with antigens. Those molecules can be used as such or integrated within a larger protein, thus forming a specific region of such protein with binding function. The varying structures can be derived from natural repertoires of binding proteins such as from immunoglobulins or antibodies. The varying structures can as well be produced by randomization techniques, in particular those described herein. These include mutagenized CDR or non-CDR regions (e.g. structural loop regions of constant antibody domains), loop regions of antibody variable domains or constant domains, in particular CDR loops of antibodies. Typically, an antigen-binding site of the ABM described herein is formed by such an antigen-binding moiety.

The antigen binding site of an antibody is typically formed by amino acid residues of the N-terminal variable ("V") regions of the heavy ("H") and/or light ("L") chains, or the variable domains thereof. Three highly divergent stretches within the V regions of the heavy and light chains, referred to as "hypervariable regions", are interposed between more conserved flanking stretches known as framework regions. The antigen-binding site provides for a surface that is complementary to the three-dimensional surface of a bound epitope or antigen, and the hypervariable regions are referred to as "complementarity-determining regions", or "CDRs." The antigen-binding site incorporated in the CDRs is herein also called "CDR binding site".

The antigen-binding site incorporated in the structural loop region of a constant antibody domain is also called "non-CDR binding site".

The term "expression" is understood in the following way. Nucleic acid molecules containing a desired coding sequence of an expression product such as e.g. an ABM as described herein, and control sequences such as e.g. a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions, e.g. for the expression of a protein coded for by foreign DNA carried by the vector and introduced to the host cell.

Coding DNA is a DNA sequence that encodes a particular amino acid sequence for a particular polypeptide or protein such as e.g. an ABM. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

"Vectors" used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells transformed to produce a particular recombinant protein, such as an ABM as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant ABM. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

The term "isolated" or "isolation" as used herein with respect to a nucleic acid, an ABM, ABMC, or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules encoding the ABM described herein are also meant to include codon-optimized variants of naturally occurring nucleic acid sequences to improve expression in a certain host cell, or those chemically synthesized.

With reference to nucleic acids, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as isolated ABM or ABMC, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

The term "recombinant" as used herein shall mean "being prepared by or the result of genetic engineering". Alternatively, the term "engineered" is used. For example, an ABM, antibody or antibody domain may be engineered to produce a variant by engineering the respective parent sequence to produce a modified ABM, antibody and domain, respectively. A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant" with respect to an ABM or antibody, as used herein, includes ABM and antibodies, respectively, that are prepared, expressed, created or isolated by recombinant means, such as (a) ABM or antibodies isolated from an animal (e.g., a mouse) that is transgenic or transchromosomal for human immunoglobulin genes or a hybridoma prepared therefrom, (b) ABM or antibodies isolated from a host cell transformed to express the ABM and antibody, respectively, e.g., from a transfectoma, (c) ABM or antibodies isolated from a recombinant, combinatorial human ABM library and antibody library, respectively, and (d) ABM or antibodies prepared, expressed, created or isolated by any other means that involve splicing of human immunoglobulin gene sequences to other DNA sequences. Such recombinant ABM or antibodies comprise ABM and antibodies, respectively, which are engineered to include rearrangements and mutations which occur, for example, during antibody maturation.

Once ABM or antibodies with the desired structure are identified, such ABM and antibodies, respectively, can be produced by methods well-known in the art, including, for example, hybridoma techniques or recombinant DNA technology.

In the hybridoma method, a mouse or other appropriate host animal, such as a hamster, is immunised to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing can be assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Recombinant ABM, in particular monoclonal antibodies, can, for example, be produced by isolating the DNA encoding the required protein and polypeptide chains e.g., antibody chains, respectively, and transfecting a recombinant host cell with the coding sequences for expression, using well-known recombinant expression vectors, e.g. the plasmids or expression cassette(s) comprising the nucleotide sequences encoding the ABM described herein. Recombinant host cells can be prokaryotic and eukaryotic cells, such as those described above.

According to a specific aspect, the nucleotide sequence may be used for genetic manipulation to humanize an ABM, in particular an antibody, or to improve its affinity, or other characteristics. For example, an antibody constant region may be engineered to more nearly resemble human constant regions to avoid immune response, if the ABM is used in clinical trials and treatments in humans. It may be desirable to genetically manipulate an ABM sequence to obtain greater affinity to the target antigen. It will be apparent to one of skill in the art that one or more polynucleotide changes can be made to the ABM and still maintain its binding ability to the target antigen.

The production of an ABM, in particular an antibody, by various means, is generally well understood. U.S. Pat. No. 6,331,415 (Cabilly et al.), for example, describes a method for the recombinant production of antibodies where the heavy and light chains are expressed simultaneously from a single vector or from two separate vectors in a single cell. Wibbenmeyer et al., (1999, Biochim Biophys Acta 1430(2): 191-202) and Lee and Kwak (2003, J. Biotechnology 101: 189-198) describe the production of monoclonal antibodies from separately produced heavy and light chains, using plasmids expressed in separate cultures of E. coli. Various other techniques relevant to the production of ABM or antibodies are provided in, e.g., Harlow, et al., ANTIBODIES: A LABORATORY MANUAL, Cold Spring Harbor Laboratory Press, Cold Spring Harbor, N.Y., (1988).

Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63).

The ABM or ABMC described herein may be used for administration to treat a subject in need thereof.

The term "subject" as used herein shall refer to a warm-blooded mammalian, particularly a human being or a non-human animal. Thus, the term "subject" may also particularly refer to animals including dogs, cats, rabbits, horses, cattle, pigs and poultry. In particular the ABM or ABMC described herein is provided for medical use to treat a subject or patient in need of prophylaxis or treatment of a disease condition. The term "patient" includes human and other mammalian subjects that receive either prophylactic or therapeutic treatment. The term "treatment" is thus meant to include both prophylactic and therapeutic treatment.

Specifically, the ABM or ABMC described herein is provided in substantially pure form. The term "substantially pure" or "purified" as used herein shall refer to a preparation comprising at least 50% (w/w), preferably at least 60%, 70%, 80%, 90% or 95% of a compound, such as a nucleic acid molecule, an ABM or ABMC. Purity is measured by methods appropriate for the compound (e.g. chromatographic methods, polyacrylamide gel electrophoresis, HPLC analysis, and the like).

The term "therapeutically effective amount", used herein interchangeably with any of the terms "effective amount" or "sufficient amount" of a compound, e.g. an ABM or ABMC described herein, is a quantity or activity sufficient to, when administered to the subject, to effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the ABM or ABMC as described herein are specifically used to treat, modulate, attenuate, reverse, or affect a disease or condition that benefits from the interaction of the ABM with its target antigen.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

The ABM or ABMC described herein may specifically be used in a pharmaceutical composition. Therefore, a pharmaceutical composition is provided which comprise an ABM or ABMC as described herein and a pharmaceutically acceptable carrier or excipient, e.g. an artificial carrier or excipient which does not naturally occur together with an immunoglobulin in a body fluid, or which naturally occurs together with an immunoglobulin, yet is provided in a preparation containing the carrier or excipient in a different amount or ratio.

Pharmaceutical compositions described herein can be administered as a bolus injection or infusion or by continuous infusion. Pharmaceutical carriers suitable for facilitating such means of administration are well-known in the art.

Pharmaceutically acceptable carriers generally include any and all suitable solid or liquid substances, solvents, dispersion media, coatings, isotonic and absorption delaying agents, and the like that are physiologically compatible with an ABM or ABMC described herein. Further examples of pharmaceutically acceptable carriers include sterile water, saline, phosphate buffered saline, dextrose, glycerol, ethanol, and the like, as well as combinations of any thereof.

In one such aspect, an ABM or ABMC can be combined with one or more carriers appropriate for a desired route of administration. An ABM or ABMC may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Alternatively, an ABM or ABMC may be dissolved in saline, water, polyethylene glycol, propylene glycol, carboxymethyl cellulose colloidal solutions, ethanol, corn oil, peanut oil, cotton-seed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein an ABM or ABMC described herein and one or more therapeutically active agents are formulated. Stable formulations are prepared for storage by mixing said ABM or ABMC having the desired degree of purity with optional pharmaceutically acceptable carriers, excipients or stabilizers, in the form of lyophilized formulations or aqueous solutions. The formulations to be used for in vivo administration are specifically sterile, preferably in the form of a sterile aqueous solution. This is readily accomplished by filtration through sterile filtration membranes or other methods. The ABM or ABMC and other therapeutically active agents disclosed herein may also be formulated as immunoliposomes, and/or entrapped in microcapsules.

Administration of the pharmaceutical composition comprising an ABM or ABMC described herein, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary, vaginally, parenterally, rectally, or intraocularly.

Exemplary formulations as used for parenteral administration include those suitable for subcutaneous, intramuscular or intravenous injection, such as, for example, a sterile solution, emulsion or suspension.

The invention specifically provides for exemplary ABM or ABMC as detailed in the examples provided herein. Further ABM or ABMC variants are feasible, e.g. including functional variants of the exemplified ABM or ABMC, e.g. where the Fc is further engineered to improve the structure and function of the molecule, or where antibodies comprising different CDR binding sites or non-CDR binding sites, e.g. with different specificity are produced.

According to specific examples, visual inspection of Fc crystal structures combined with FoldX was used to predict the possible effects of the mutations on the Fc molecule (Schymkowitz et al., 2005). The cysteines were introduced in the wild-type Fc fragment of an IgG1 antibody. The resulting mutant Fc fragments were characterized for biochemical and biophysical properties by size exclusion chromatography, circular dichroism spectroscopy, and differential scanning calorimetry. Surface plasmon resonance measurements were employed to characterize binding to Protein A, FcRn, CD16a, and CD64. An Ellman's assay was used to titrate free thiols on the molecule. Proteins were specifically biotinylated with a commercial maleimide coupling kit. Biotinylation was subsequently assayed with a streptavidin binding assay using biolayer interferometry. Mutations that yielded Fc fragments with wild type-like SEC, DSC, CD profiles and specific biotinylation, were then introduced into an EGFR-binding Fcab. The same basic characterization of proteins was done and additionally, an internalization assay in which the EGFR-binding Fcab was specifically coupled to a fluorophore was performed to prove that this preADC construct had all expected and necessary properties.

Compared to prior art cysteine substitutions, the cysteines at positions 108 and 113 (numbering according to the IMGT) were both found buried, as analyzed by Getarea (http://curie.utmb.edu/getarea.html; reference Fraczkiewicz, R. and Braun, W. (1998) *J. Comp. Chem.*, 19, 319-333.)

while all other prior art residues were found to be solvent exposed. Those prior art substitutions were made because of such exposure, assuming that drug conjugation at such positions provides a better result. However, it was surprising that the selection of buried positions in the F-G loop of a CH2 domain, as described herein, was even better because of a surprising lesser degree of oxidative post-translational modification of the engineered cysteines during production of the recombinant antibodies.

Such oxidative post-translational modification is well known to occur (Chen X N et al. MAbs. 2009; 1(6):563-71), e.g. in the form of cysteinylation and/or glutathionylation at the engineered and unpaired cysteines through disulfide bonds formed during the cell culture process.

Mutating positions in the antibody to cysteines which are not solvent exposed during the production process was surprisingly found to reduce the amount of oxidative post-translational modification, thus rendering the SH groups of the engineered cysteines available to conjugation to the heterologous molecule.

The foregoing description will be more fully understood with reference to the following examples. Such examples are, however, merely representative of methods of practicing one or more embodiments of the present invention and should not be read as limiting the scope of invention.

EXAMPLES

Example 1: Structural Tolerance of CH2 Domains Determined by N-Terminal Loop Screening In order to determine which of the three N-terminal loops of the CH2 domain of IgG can be employed for further engineering with cysteine mutations for the coupling of toxin molecules the following experiments were performed. A recognition sequence sequence ELDKWA (SEQ ID NO:11) was grafted onto the N-terminal loops of the Fc fragment by exchanging the residues of the BC loop, DE loop and FG loop using site directed mutagenesis with pairs of primers elbc1, elbc2, elde1, elde2, elfg1 and elfg2. The sequence of human IgG1 Fc cloned into the *Pichia pastoris* expression vector pPICZalphaA (Thermo Fisher Scientific, Fc amino acid sequence in SEQ ID NO:9) was mutagenized using Quikchange mutagenesis kit (Agilent) to give the constructs Fc_ELDKWA_BC (SEQ ID NO:13), Fc_ELDKWA_DE (SEQ ID NO:14) and Fc_ELDKWA_FG (SEQ ID NO:15). Vectors encoding the mutants were linearized and transformed into *Pichia pastoris* X33 using standard methods. Selection was performed on zeocin-containing YPD medium. Transformants were cultured in YPG medium and protein expression was induced with the addition of 1% methanol and continued for the course of 3 days. Supernatant was then clarified and the peptide engrafted Fc fragments were purified by Protein A chromatography. Briefly, supernatant was buffered to 0.1M Na-phosphate, pH 7.0, and loaded onto a Protein A column equilibrated with the same buffer. After washing, proteins were eluted with 0.1M glycine, pH 3.5. Fractions containing the eluate were neutralized with the addition of 2M Tris and dialysed against PBS. Engrafted mutants were then tested for their integrity by monitoring the SEC profile in native conditions and their ability of antigen recognition. The Fc mutant with modifications in the BC-loop produced a broad elution profile, while DE- and FG-engrafted variants were wild-type like. In an ELISA assay, ELISA Maxisorp plates were coated with 5 µg/ml 2F5 antibody. After blocking with 4% BSA-PBS, Fc variants in 3-fold dilution series starting from 10 µg/ml were allowed to react with the antigen. Binding was detected with protein A-HRP conjugate and the reaction was developed with TMB and stopped with 30% $H_2SO_4$. Absorbance was read at 405 nm and the background at 620 nm subtracted. DE- and FG-loop engrafted proteins have shown a stronger affinity towards the antigen comparing with the BC-loop engrafted variant. As the DE-loop directed graft obliterates the natively occurring N-linked glycosylation site of human IgG1 (residue Asn297 in EU numbering and 84.4 in IMGT numbering), and since the direct vicinity of the N-linked glycosylation to a cysteine-conjugated toxin molecule is not desirable, the amino acid residues exchanged in the FG loop appeared most suited for substitution and further engineering by mutagenesis to cysteine residues.

Fc wild-type sequence
SEQ ID NO: 12:
TCPPCPAPELLGGPSVFLFPPKPKDTLMISRIPEVTCVVVDVSHEDPEVK

FNWYVDGVEVHNAKKPREEQYNSTYRVVSVLTVLHQDWLNGKEYKCKVSN

KALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSC

SVMHEALHNHYTQKSLSLSPGK

Fc_ELDKWA_BC
SEQ ID NO: 13:
TCPPCPAPELLGGPSVFLFPPKPKDTLMISRTPEVTCVVVELDKWAPEVK

FNWYVDGVEVHNAKTKPREEQYNSTYRVVSVLTVLHQDWLNGKEYKCKVS

NKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFS

CSVMHEALHNHYTQKSLSLSPGK

Fc_ELDKWA_DE
SEQ ID NO: 14:
TCPPCPAPELLGGPSVFLFPPKPKDTLMISRTPEVTCVVVDVSHEDPEVK

FNWYVDGVEVHNAKTKPREELDKWAYRVVSVLTVLHQDWLNGKEYKCKVS

NKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFS

CSVMHEALHNHYTQKSLSLSPGK

Fc_ELDKWA_FG
SEQ ID NO: 15:
TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

ELDKWAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFS

CSVMHEALHNHYTQKSLSLSPGK

TABLE 1

| Elbc1 | GTCACATGCGTGGTGGTGGAACTCGATAAGTGGGCCCC<br>TGAGGTCAAGTTCAACTGG<br>SEQ ID NO: 16 |
|---|---|
| Elbc2 | CCAGTTGAACTTGACCTCAGGGGCCCACTTATCGAGTT<br>CCACCACCACGCATGTGAC<br>SEQ ID NO: 17 |
| Elde1 | CAAGACAAAGCCGCGCGAGGAACTCGATAAGTGGGCCT<br>ACCGTGTGGTCAGCGTCC<br>SEQ ID NO: 18 |

TABLE 1-continued

| | |
|---|---|
| E1de2 | GGACGCTGACCACACGGTAGGCCCACTTATCGAGTTCC<br>TCGCGCGGCTTTGTCTTG<br>SEQ ID NO: 19 |
| E1fg1 | CAAGTGCAAGGTCTCCGAACTCGATAAGTGGGCCCCA<br>TCGAGAAAACCATCTCC<br>SEQ ID NO: 20 |
| E1fg2 | GGAGATGGTTTTCTCGATGGGGGCCCACTTATCGAGTT<br>CGGAGACCTTGCACTTG<br>SEQ ID NO: 21 |

TABLE 2

ELISA showing binding of N-terminal loop engrafted Fc variants to 2F5 antibody

| Fc variant (μg/ml) | Fc wt | Fc ELDKWA (SEQ ID NO: 11) BC | Fc ELDKWA (SEQ ID NO: 11) DE | Fc ELDKWA (SEQ ID NO: 11) FG |
|---|---|---|---|---|
| 10 | 0.06466667 | 0.619 | 1.24566667 | 1.4035 |
| 3.33333333 | 0.02366667 | 0.23166667 | 0.84566667 | 1.3155 |
| 1.11111111 | 0.01333333 | 0.091 | 0.495 | 0.706 |
| 0.37037037 | 0.01633333 | 0.047 | 0.18533333 | 0.297 |
| 0.12345679 | 0.013 | 0.02133333 | 0.06733333 | 0.1085 |
| 0.04115226 | 0.01566667 | 0.01966667 | 0.038 | 0.0365 |
| 0.01371742 | 0.00933333 | 0.01066667 | 0.02833333 | 0.0215 |
| 0.00457247 | 0.01466667 | 0.01333333 | 0.01766667 | 0.012 |

Example 2: Screening of Residues of the FG Loop in the CH2 Domain for Permissiveness to Exchange to a Cysteine Residue Mutants of an Fc fragment, cloned into pPICZalphaA vector, were constructed using Quikchange site-specific mutagenesis kit. Residues Ser324, Asn325, Lys326, Ala327, Leu328, Pro329 and Ala330 were separately exchanged for cysteine residues.

TABLE 3

| | |
|---|---|
| S324C_for | GGAGTACAAGTGCAAGGTCTGTAACAAAGCC<br>CTCCCAGCCCCC<br>SEQ ID NO: 22 |
| S324C_back | GGGGGCTGGGAGGGCTTTGTTACAGACCTTG<br>CACTTGTACTCC<br>SEQ ID NO: 23 |
| N325C_for | GGGGGCTGGGAGGGCTTTACAGGAGACCTTG<br>CACTTGTACTC<br>SEQ ID NO: 24 |
| N325C_back | GGGGGCTGGGAGGGCTTTACAGGAGACCTTG<br>CACTTGTACTC<br>SEQ ID NO: 25 |
| K326C_for | GTGCAAGGTCTCCAACTGTGCCCTCCCAGCC<br>CCC<br>SEQ ID NO: 26 |
| K326C_back | GGGGGCTGGGAGGGCACAGTTGGAGACCTTG<br>CAC<br>SEQ ID NO: 27 |
| A327C_for | GCAAGGTCTCCAACAAATGCCTCCCAGCCCC<br>CATCG<br>SEQ ID NO: 28 |
| A327C_back | CGATGGGGGCTGGGAGGCATTTGTTGGAGAC<br>CTTGC<br>SEQ ID NO: 29 |

TABLE 3-continued

| | |
|---|---|
| L328C_for | GGTCTCCAACAAAGCCTGCCCAGCCCCCATC<br>GAGAAAACC<br>SEQ ID NO: 30 |
| L328C_back | GGTTTTCTCGATGGGGGCTGGGCAGGCTTTG<br>TTGGAGACC<br>SEQ ID NO: 31 |
| P329C_for | GGTCTCCAACAAAGCCCTCTGCGCCCCCATC<br>GAGAAAACC<br>SEQ ID NO: 32 |
| P329C_back | GGTTTTCTCGATGGGGCGCAGAGGGCTTTG<br>TTGGAGACC<br>SEQ ID NO: 33 |
| A330C_for | GGTCTCCAACAAAGCCCTCCCATGCCCCATC<br>GAGAAAACC<br>SEQ ID NO: 34 |
| A330C_back | GGTTTTCTCGATGGGGCATGGGAGGGCTTTG<br>TTGGAGACC<br>SEQ ID NO: 35 |

Vectors encoding the mutants were linearized and transformed into *Pichia pastoris* X33 (Invitrogen). Selection was performed on zeocin-containing YPD medium. Transformants were cultured in YPG medium and protein expression was induced with the addition of 1% methanol and continued for the course of 3 days. Supernatant was then clarified and the mutant Fc fragments were purified by Protein A chromatography. Briefly, supernatant was buffered to 0.1M Na-phosphate, pH 7.0, and loaded onto a Protein A column equilibrated with the same buffer. After washing, proteins were eluted with 0.1M glycine, pH 3.5. Fractions containing the eluate were neutralized with the addition of 2M Tris and dialysed against PBS. Mutants were analyzed for integrity by monitoring the SEC profile in native conditions, and found to elute at a time typical of wild-type Fc. The mutant Lys326Cys contained 5-10% of aggregates, Ala327Cys contained 5% of aggregates and all other preparations were free of aggregate.

Thermostability profiles of the mutants were determined using differential scanning calorimetry. 5 μM protein solution was exposed to heating from 25° C. to 100° C. at 1° C./min heating rate in Automated VP-DSC apparatus, cooled in situ and heated for a second temperature scan, which served as a baseline. For evaluation, the baseline was subtracted from the thermal profile and deconvoluted assuming a non-2-state transition mechanism using Origin 7.0 for Windows. Thermal transition of the CH3 domain was almost identical to unmodified Fc. In contrast, the transition corresponding to the unfolding of the CH2 domain occurred at a lower temperature in most mutants. The most severely destabilized CH2 domains were observed in mutants Lys326Cys and Leu328Cys with a negative shift in Tm of 4.5° C. Ser324Cys was destabilized by about 3.5° C. The entire melting curves of the mutants Asn325Cys and Ala327Cys did not differ significantly from those of wild-type Fc.

Proteins were tested for their reactivity with maleimide-biotin using the reagent EZ-Link Maleimide-PEG2-Biotin (Thermo Scientific). After coupling, proteins were dialysed against PBS and afterwards probed for their binding onto streptavidin tips in ForteBio Octet using biolayer interferometry. Proteins were allowed to bind for 600 s and dissociation phase was 600 s. There was a strong positive signal exhibited by Fc_Asn325Cys, and a weaker positive signal by Fc_Ser324Cys and Fc_Leu328Cys. All other mutants including wild type Fc were negative in this assay.

Free thiol groups were determined using Ellman's assay. The assay was performed with Ellman's reagent (5,5'-dithiobis(2-nitrobenzoic acid)) according to Riener et al. (Riener C K, Kada G, Gruber H J. Quick measurement of protein sulfhydryls with Ellman's reagent and with 4,4'-dithiodipyridine. Anal Bioanal Chem. 2002; 373(4-5): 266-276). Briefly, protein samples were thawed and applied without dilution. Two tubes containing 100 mM Na-phosphate buffer (+0.2 mM EDTA) were prepared and the pH was set to 7.0 and 8.0, respectively. Immediately before the assay, a 10 mM DTNB (77.1 mg DTNB in 25 mL of Na-phosphate buffer, pH 7) was prepared. 200 µM of BSA solution were used as a positive control. 833 µL buffer pH 8+167 µL protein+16.7 µL Ellman's reagent were mixed and incubated for 30 minutes at 20° C. with shaking at 300 rpm. After incubation, absorption at 412 nm was measured on a Hitachi U2910 spectrophotometer and the concentration of thiols was obtained using following equation:

$$[SH]M = (A_{412_{sample}} - A_{412_{no\ reagent}} - A_{412_{no\ protein}}) \div \varepsilon_{412} \div d \times 6$$

with: [SH]M—molar concentration of thiols in the sample; $A_{412_{sample}}$—absorption at 412 nm of the sample; $A_{412_{no\ reagent}}$—absorption at 412 nm without reagent; $A_{412_{no\ protein}}$—absorption at 412 nm of blank without protein; $\varepsilon_{412}$—molar extinction coefficient at 412 nm (14,150 $M^{-1}$ $cm^{-1}$); d—pathlength of the cuvette; 6 is the dilution factor.

With BSA as control displaying the molar concentrations of thiols of 0.6, the mutant Fc_Asn325Cys has shown near to two free thiol groups per mole available for coupling. Mutants Fc_Ser324Cys and Fc_Leu328Cys have shown less than one free thiol group per mole available for coupling. Other proteins have shown no presence of free thiol groups. Proteins that have been allowed to react with EZ-Link Maleimide-PEG2-Biotin (Thermo Scientific) have shown reduced availability of free thiol groups.

TABLE 4

| mutant | Molar concentration of thiol groups determined with Ellman's assay. | |
|---|---|---|
| | molar concentration of thiols in non-treated protein | molar concentration of thiols in biotinylated protein sample |
| Ser324Cys | 0.33 | 0.14 |
| Asn325Cys | 1.74 | 0.29 |
| Lys326Cys | 0.1 | 0 |
| Ala327Cys | 0 | 0 |
| Leu328Cys | 0.29 | 0.13 |
| Pro329Cys | 0.03 | 0 |
| Ala330Cys | 0.0 | 0.0 |

CD16a binding was determined with BIAcore measurement. The Fc mutants Ser324Cys and Lys326Cys showed similar binding to CD16a like wild-type Fc. All other clones showed dramatically reduced affinity to this receptor. In the case of Pro329Cys and biotinylated Asn325Cys, no binding could be observed.

FcRn binding was determined with a BIAcore measurement. Both association and dissociation to FcRn was similar for wild-type Fc and all cysteine mutants. Biotinylation had no effect on FcRn binding.

Example 3: Ser324Cys, Asn325Cys and Leu328Cys Mutants in EGFR-Binding Fcab Clone Out of 7 mutants in the FG loop of the CH2 domain in wt Fc, 3 single cysteine exchanged mutants were transferred to the EGFR binding Fcab clone EAM151-5 (WO2011003811A1):Ser324Cys, Asn325Cys and Leu328Cys. Mutants were constructed using Quikchange Site-Directed mutagenesis kit and primers as listed in the table below.

TABLE 5

| EAM_S324C_for | GAGTACAAGTGCAAGGTGTGTAACAAGGCC CTGCCTGC SEQ ID NO: 36 |
|---|---|
| EAM_S324C_back | GCAGGCAGGGCCTTGTTACACACCTTGCACT TGTACTC SEQ ID NO: 37 |
| EAM_N325C_for | GAGTACAAGTGCAAGGTGAGCTGTAAAGCCC TGCCTGCCCCC SEQ ID NO: 38 |
| EAM_N325C_back | GGGGGCAGGCAGGGCTTTACAGCTCACCTTG CACTTGTACTC SEQ ID NO: 39 |
| EAM_L328C_for | GGTGAGCAACAAGGCCTGTCCTGCACCCATC GAGAAGACC SEQ ID NO: 40 |
| EAM_L328C_back | GGTCTTCTCGATGGGTGCAGGACAGGCCTTG TTGCTCACC SEQ ID NO: 41 |

The mutant EAM151-5 Asn325Cys and wild-type EAM151-5 clone were labelled with iodoacetyl-biotin using the reagent EZ-Link Iodoacetyl-PEG2-Biotin (Thermo Scientific). Immediately before use, a 4 mM solution of Iodoacetyl Biotin Reagent was prepared. A calculated amount of reagent solution was added to the protein solution and incubated in the dark at RT for 90 minutes. Non-reacted Biotin Reagent was removed by dialysis at 4° C. against PBS. The mutant EAM151-5 Asn325Cys exhibited significant binding to streptavidin tips in ForteBio Octet in biolayer interferometry while biotinylated wild-type EAM151-5, biotinylated wild-type Fc and the non-biotinylated proteins EAM151-5 Asn325Cys, EAM151-5 and wild-type Fc showed no binding to streptavidin tips.

Free thiol groups were titrated with Ellman's reagent. BSA was used as a control and has shown 0.64 free thiol groups pro molecule. Single cysteine substituted molecules have shown different number of accessible thiol groups pro molecule:EAM151-5 Asn325Cys has shown 1.62, EAM151-5 Ser324Cys 0.83 and EAM151-5 Leu328Cys showed 1.2 free thiol groups per molecule. Unmodified EAM151-5 gave a negative result (0.16 free thiols per molecule) and so did the wild-type Fc (0.1 free thiols per molecule).

Deconvolution of the thermal unfolding profile of *P. pastoris*-derived Fcab EAM151-5 could be solved using three non-2-state transitions, the first of which occurred at 63.55° C., the second at 66.29° C., and the third at 67.99° C. The most destabilized mutant Fcab was EAM Leu328Cys with transition temperatures of 58.59° C., 62.22° C., and 65.82° C. EAM Ser324Cys also showed a destabilized profile in DSC (58.94° C., 62.89° C., and 65.60° C.). In contrast, EAM Asn325Cys showed a thermostability profile close to that of EAM151-5 with the CH2 domain melting at 61.87° C. and its CH3 domain retained its thermostability (Tms at 65.71° C. and 68.37° C.).

Binding to CD16a and CD64 was determined using surface plasmon resonance. Mutants Asn325Cys and Leu328Cys in the scaffold of the wild-type Fc have shown a markedly reduced affinity to CD16a in comparison with wild-type Fc. EAM151-5 showed binding kinetics to CD16a similar to wild-type Fc. EAM Ser324Cys exhibited binding kinetics similar to that of EAM151-5 independent of biotinylation. In contrast, EAM Leu328Cys bound to CD16a to a greatly reduced extent when non-treated, whereas binding was almost completely lost when biotinylated. EAM151-5 Asn325Cys showed even weaker binding than EAM151-5 L328C and no reactivity when biotinylated. Further, mutants Asn325Cys and Leu328Cys in the scaffold of the wild-type Fc have shown a reduction of affinity to CD64 in comparison with the wild-type Fc. Binding of the EAM151-5 to CD64 was reduced in comparison with the wild-type Fc. Mutants EAM151-5 Asn325Cys and EAM151-5 Leu328Cys have shown less binding to CD64 than the clone EAM151-5.

TABLE 6

Binding of wild-type Fc, single substituted mutants Fc Asn325Cys and Fc Leu328Cys, clone EAM151-5 and single substituted mutants EAM151-5 Asn325Cys and EAM151-5 Leu328Cys to CD16a and CD64.

| Mutant | Binding to CD16a | Binding to CD64 |
|---|---|---|
| Wild-type Fc | +++ | +++ |
| Fc Asn325Cys | + | ++ |
| Fc Leu328Cys | + | ++ |
| EAM151-5 | +++ | ++ |
| EAM151-5 Asn325Cys | +− | + |
| EAM151-5 Leu328Cys | +− | + |

Kinetics of binding to FcRn was similar for all of the EAM151-5 mutants. No difference in binding to FcRn could be observed for biotinylated proteins.

In an ELISA determining binding to EGFR, EAM151-5 and the single cysteine substituted mutants showed almost identical binding to EGFR while wild-type Fc served as negative control. The engineered Fc fragments after biotinylation showed very similar binding behavior.

The internalization of EAM151-5 mutants was observed in vitro in a cell assay using fluorescent microscopy (Table 7). Strongly EGFR-positive MB-MDA468 cells were incubated with 5 µg/mL Fc fragment or EAM151-5 clone with engineered free cysteines that had previously been conjugated with Dylight488 maleimide at 4° C. and 37° C. to analyze the active internalization. As a negative control, DyLight488-labelled Fc fragment with engineered free cysteines (Fc Asn325Cys) was used. In order to confirm specificity of the uptake by MB-MDA468 cells, the cell line EGFR-negative MCF-7 cell line was used. Wild-type EAM151-5 was used for a negative control. All modified EAM151-5 mutants were internalized by the cells. When cells were incubated with the fluorescently labelled Fc derivates at 4° C., the Fc mutants were mainly located on the cell surface and cell fluorescence was interpreted as a positive signal. When the incubation of the cells with fluorescently labelled Fc mutants was performed at 37° C., punctuate appearance indicated internalization of the fluorescently labelled Fc fragment derivates and this was interpreted as a positive signal. MCF-7 cells have not shown any staining with the Dy-Light488 conjugated EAM Asn325Cys. Unmodified EAM151-5 has shown a weak positive signal upon internalization into MB-MDA468 cells, probably due to unspecific labelling with Dy-Light488.

TABLE 7

Surface staining and internalization of EGFR-binding Fc fragments into MB-MDA468 cells.

| Mutant | Incubation at 4° C. | Incubation at 37° C. |
|---|---|---|
| Fc Asn325Cys | − | + − |
| EAM151-5 | Not done | + |
| EAM151-5 Asn325Cys | +++ | +++ |
| EAM151-5 Leu328Cys | +++ | +++ |

Example 4: Asn325Cys and Leu328Cys Mutants in a Her2-Binding Fcab Clone

Her2-specific Fcab clone H561-4 (Leung et al. Mol Ther. 2015; 23(11):1722-1733) cloned into pTT5 vector (CNRC) was used as a backbone to introduce the mutations Asn325Cys and Leu328Cys. The mutations were introduced using HiSpeed Quikchange mutagenesis kit as described in examples 2 and 3. Proteins were expressed in CHO cells and purified using Protein A chromatography H561-4 Asn325Cys clone protein sequence
SEQ ID NO: 42
TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

CKALPAPIEKTISKAKGQPREPQVYTLPPSRDEFFTYWVSLTCLVKGFYP

SDIAVEWESNGQPENNYKTTPPVLDSDGSFFLYSKLTVDRRRWTAGNVFS

CSVMHEALHNHYTQKSLSLSPGK.

```
H561-4 Leu328Cys clone protein sequence
                                       SEQ ID NO: 43
TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKACPAPIEKTISKAKGQPREPQVYTLPPSRDEFFTYWVSLTCLVKGFYP

SDIAVEWESNGQPENNYKTTPPVLDSDGSFFLYSKLTVDRRRWTAGNVFS

CSVMHEALHNHYTQKSLSLSPGK.
```

Tubulysin conjugate with a SPDB linker was coupled to Fcab H-561-4 according to the following protocol: toxin was diluted in DMSO and added to protein preparations in 1:4 molar ratio. Incubation was for 1.5 h at room temperature. Mixtures were loaded onto PD-10 columns equilibrated in PBS and protein was collected in 1-ml-fractions. Protein-containing fractions were identified by measuring $A_{280}$, and dialysed against PBS overnight.

Coupled mutants were subjected to mass spectrometry analysis. 3 μg of the desired protein were directly injected to the LC-MS system (LC:DionexbUltimate 3000 LC, MS:Bruker, Maxis 4G, equipped with the standard ESI source). The protein was eluted by developing a linear gradient from 15% to 70% acetonitrile (Supelco Discovery Bio Wide Pore C5 column, 50*0.32 mm, 3 μm packing). Data was processed using Data Analysis 4.0 (Bruker) and the spectrum was deconvoluted by MaxEnt.

For the variant H561-4 Asn325Cys, the measurement of the intact protein showed a heterogeneous spectrum, three different major variants were detected, exhibiting 948 Da mass increments. Nevertheless the full length protein (missing the terminal lysine) showed the highest intensity. The treatment with the cysteine modifying agent caused a shift of the largest peak of approx. 829.5 Da, caused by one modified cysteine residue. For the variant H561-4 Leu328Cys, the measurement of the intact protein showed a heterogeneous spectrum, three different major variants were detected, exhibiting 948 Da mass increments. Nevertheless the full length protein (missing the terminal lysine) showed the highest intensity. The treatment with the cysteine modifying agent caused a shift of the largest peak of approx. 1659 Da, caused by two modified cysteine residues. See FIG. 1.

Example 5: Asn325Cys and Leu328Cys Mutants in Cetuximab Framework

The sequence of the heavy chain of cetuximab (CX) was cloned into the pTT5 mammalian cell expression vector. Single amino acid substitutions Asn325Cys and Leu328Cys were introduced into the CX sequence (sequence below) using the Lightning Quikchange mutagenesis kit. Mutations Thr250Val and the combined mutations Pro271Cys and Arg292Cys (CysP6 or CP6) that lead to a de novo disulphide bond (CysP6) that stabilizes the $C_H2$ domain for 9° C. in respect to the wild type were introduced into the sequences of CXAsn325Cys and CXLeu328Cys mutants. Heavy chain constructs were mixed with CX light chain construct in 1:1 mass ratio and transfected into CHO—S cells according to the standard protocols. 30 ml CHO—S cells was transfected at a density of 1×10⁶/ml with a mixture of 37.5 μg DNA, 37.5 μl MAX reagent, each diluted in 600 μl Opti-Pro medium. After cultivation at 37° C. for 7 days, under 5% $CO_2$ in humidified atmosphere, supernatants were harvested and proteins isolated using Protein A purification. Briefly, supernatants were buffered with 0.1 M Na-phosphate for binding to Protein A Hi-Trap column, eluted with pH shift to 3.5 with 0.1M glycine and neutralized immediately with 2M Tris. After extensive dialysis in PBS, proteins were stored at −80° C.

```
CX heavy chain amino acid sequence (the first 19
amino acids, leader peptide underlined)
                                       SEQ ID NO: 44
MAVLGLLFCLVTFPSCVLSQVQLKQSGPGLVQPSQSLSITCTVSGFSLTN

YGVHWVRQSPGKGLEWLGVIWSGGNTDYNTPFTSRLSINKDNSKSQVFFK

MNSLQSNDTAIYYCARALTYYDYEFAYWGQGTLVTVSAASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK.

CX heavy chain nucleotide sequence
                                       SEQ ID NO: 45
ATGGCTGTCTTGGGGCTGCTCTTCTGCCTGGTGACATTCCCAAGCTGTGT

CCTATCCCAGGTGCAGCTGAAGCAGTCAGGACCTGGCCTAGTGCAGCCCT

CACAGAGCCTGTCCATCACCTGCACAGTCTCTGGTTTCTCATTAACTAAC

TATGGTGTACACTGGGTTCGCCAGTCTCCAGGAAAGGGTCTGGAGTGGCT

GGGAGTGATATGGAGTGGTGGAAACACAGACTATAATACACCTTTCACAT

CCAGACTGAGCATCAACAAGGACAATTCCAAGAGCCAAGTTTTCTTTAAA

ATGAACAGTCTGCAATCTAATGACACAGCCATATATTACTGTGCCAGAGC

CCTCACCTACTATGATTACGAGTTTGCTTACTGGGGCCAAGGGACTCTGG

TCACTGTCTCTGCAGCTAGCACCAAGGGCCCCAGCGTGTTCCCTCTGGCC

CCCAGCTCCAAGAGCACCTCCGGCGGCACCGCCGCCCTGGGCTGCCTGGT

GAAGGATTACTTCCCAGAGCCCGTGACCGTGAGCTGGAACAGCGGCGCCC

TGACCAGCGGCGTGCACACCTTTCCCGCCGTGCTGCAGTCCAGCGGCCTG

TACTCCCTGAGCAGCGTGGTGACCGTGCCCAGCAGCAGCCTGGGCACCCA

GACCTACATCTGCAATGTGAACCACAAGCCCAGCAATACCAAGGTGGATA

AGAAGGTGGAGCCCAAGAGCTGCGACAAGACACACACGTGTCCCCCATGT

CCCGCCCCTGAGCTGCTGGGCGGCCCTTCCGTGTTCCTGTTCCCTCCCAA

GCCAAAGGACACCCTGATGATCTCCCGGACCCCTGAGGTGACCTGTGTGG

TGGTGGACGTGAGCCACGAGGACCCAGAGGTGAAGTTCAACTGGTACGTG

GACGGCGTGGAGGTGCACAACGCCAAGACCAAGCCTAGAGAGGAGCAGTA

CAACAGCACCTACCGCGTGGTGAGCGTGCTGACCGTGCTGCACCAGGATT

GGCTGAATGGCAAGGAGTACAAGTGCAAGGTGAGCAACAAGGCCCTGCCT

GCCCCCATCGAGAAGACCATCTCCAAGGCCAAGGGCCAGCCTCGAGAACC
```

-continued
ACAGGTGTACACCCTGCCCCCATCCCGGGATGAGCTGACCAAGAACCAGG

TCAGCCTGACCTGCCTGGTCAAAGGCTTCTATCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACACAGAAGAGCCTCTCCCTGTCTCCGGG

TAAA.

CX light chain amino acid sequence (the first 20
amino acids, leader peptide underlined)
SEQ ID NO: 46
MVSTPQFLVFLLFWIPASRGDILLTQSPVILSVSPGERVSFSCRASQSIG

TNIHWYQQRTNGSPRLLIKYASESISGIPSRFSGSGSGTDFTLSINSVES

EDIADYYCQQNNNWPTTFGAGTKLELKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC.

CX light chain nucleotide sequence
SEQ ID NO: 47
ATGGTATCCACACCTCAGTTCCTTGTATTTTTGCTTTTCTGGATTCCAGC

CTCCAGAGGTGACATCTTGCTGACTCAGTCTCCAGTCATCCTGTCTGTGA

GTCCAGGAGAAAGAGTCAGTTTCTCCTGCAGGGCCAGTCAGAGTATTGGC

ACAAACATACACTGGTATCAGCAAAGAACAAATGGTTCTCCAAGGCTTCT

CATAAAGTATGCTTCTGAGTCTATCTCTGGAATCCCTTCCAGGTTTAGTG

GCAGTGGATCAGGGACAGATTTTACTCTTAGCATCAACAGTGTGGAGTCT

GAAGATATTGCAGATTATTACTGTCAACAAAATAATAACTGGCCAACCAC

GTTCGGTGCTGGGACCAAGCTGGAGCTGAAAAGAACTGTTGCGGCGCCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGT

GT

TABLE 8

| CXN325C1 | CAAGTGCAAGGTGAGCTGTAAGGCCCTGCCTGCC<br>SEQ ID NO: 48 |
| CXN325C2 | GGCAGGCAGGGCCTTACAGCTCACCTTGCACTTG<br>SEQ ID NO: 49 |
| CXL328C1 | GTGAGCAACAAGGCCTGCCCTGCCCCCATCGAGAAG<br>SEQ ID NO: 50 |
| CXL328C2 | CTTCTCGATGGGGGCAGGGCAGGCCTTGTTGCTCAC<br>SEQ ID NO: 51 |
| CXP271C1 | GGACGTGAGCCACGAGGACTGCGAGGTGAAGTTCAAC<br>SEQ ID NO: 52 |
| CXP271C2 | GTTGAACTTCACCTCGCAGTCCTCGTGGCTCACGTCC<br>SEQ ID NO: 53 |
| CXR292C1 | CGCCAAGACCAAGCCTTGCGAGGAGCAGTACAAC<br>SEQ ID NO: 54 |
| CXR292C2 | GTTGTACTGCTCCTCGCAAGGCTTGGTCTTGGCG<br>SEQ ID NO: 55 |
| CXT250V1 | CTCCCAAGCCAAAGGACGTGCTGATGATCTCCCGGAC<br>SEQ ID NO: 56 |
| CXT250V2 | GTCCGGGAGATCATCAGCACGTCCTTTGGCTTGGGAG<br>SEQ ID NO: 57 |

Mutants were labelled by incubation with maleimide-Alexafluor488 and dialysed extensively against PBS to remove the unreacted reagent. Their level of binding to the strongly EGFR-positive cells MB-MDA468 and A431 was estimated in comparison with cetuximab coupled with Alexafluor488 over lysine residues using NHS-coupling chemistry using FACS experiment. Cells were harvested and resuspended at a density of $1\times10^6$ cells/ml in 2% BSA-PBS. Staining was performed in 96-well plates with 100 000 cells/well. Cells were blocked for 30 min in ice and then incubated with primary antibodies coupled with Alexafluor488 in 3-fold dilution series in 2% BSA-PBS starting from 10 nM on ice for 30 min. Before analysis, the cells were resuspended in 200 µl PBD with 7-AAD diluted 1:100 and kept on ice. Mean fluorescent intensity of live cell population was determined. High fluorescent signal indicated successful coupling of maleimide-derivatized fluorophore with cysteine residues.

Further, the internalization of the constructs was estimated by exposing the cells to a saturation concentration of the antibody for different periods of time. Cells were then harvested, blocked in 2% BSA-PBS and incubated with 50 µg/ml of Alexa488-quenching antibody. Percentage of the internalized antibody was determined according to the published protocol. The time course of the internalization was monitored and estimated to be similar to internalization of cetuximab coupled with Alexafluor488 over lysine residues.

For the production on a larger scale, the constructs were transfected into ExpiCHO cells. Protein production was performed using MaxTiter protocol. Proteins were isolated using Protein A and SEC purification. Coupling with toxin mal-val-cit-MMAE (vedotin) was performed in the labs of ADCs & Targeted NBE Therapeutics (Merck). The drug to antibody ratio (DAR) was determined to be of 1:1.26 for CX_Asn325Cys, 1:1.64 for CX_Asn325Cys, 1:1.64 for CX_Leu328Cys and 1:52 for CX_Leu328Cys_CysP6 using mass spectrometry.

TABLE 9

Binding to MB-MDA468 cell line of mutants labelled with Alexafluor488 using maleimide coupling.

| c (Ab) | CX_N325C (nM) | | CX_N325C_CP6 (nM) | | CX_N325C_T250V | |
|---|---|---|---|---|---|---|
| | geo mean | SD | geo mean | SD | geo mean | SD |
| 33.3 | 21.61 | 0.2969848 | 18.05 | 0 | 20.885 | 1.1850005 |
| 11.1 | 21.385 | 0.6010407 | 17.855 | 0.077781 | 20.56 | 0.6771431 |
| 3.7 | 19.16 | 0.2121320 | 17.175 | 0.021213 | 18.45 | 0 |
| 1.2333333 | 9.64 | 0.0707106 | 9.585 | 0.799030 | 10.07 | 0.6771431 |
| 0.4111111 | 3.62 | 0.5939697 | 3.78 | 0.480832 | 3.52 | 0.6771431 |
| 0.1370370 | 1.55 | 0.2404163 | 1.45 | 0.169705 | 1.405 | 0.1015714 |
| 0.0456790 | 0.825 | 0.0636396 | 0.775 | 0.049497 | 0.725 | 0.0338571 |
| 0.0152263 | 0.555 | 0.0494974 | 0.525 | 0.007071 | 0.47 | 0.1354286 |

| c (Ab) | CX_L328C (nM) | | CX_L328C_CP6 (nM) | |
|---|---|---|---|---|
| | geo mean | SD | geo mean | SD |
| 33.30 | 4.365 | 0.16263456 | 4.125 | 0.0212132 |
| 11.10 | 4.23 | 0.12727922 | 4.16 | 0.01414214 |
| 3.70 | 3.305 | 0.06363961 | 3.95 | 0.09899495 |
| 1.23 | 1.955 | 0.26162951 | 2.47 | 0.18384776 |
| 0.41 | 0.955 | 0.0212132 | 1.13 | 0.05656854 |
| 0.14 | 0.575 | 0.00707107 | 0.615 | 0.0212132 |
| 0.05 | 0.445 | 0.00707107 | 0.435 | 0.0212132 |
| 0.02 | 0.385 | 0.00707107 | 0.38 | 0 |

TABLE 10

Binding to A431 cell line of mutants labelled with Alexafluor488 using maleimide coupling.

| c (Ab) | CX_N325C (nM) | | CX_N325C_CP6 (nM) | | CX_N325C_T250V | |
|---|---|---|---|---|---|---|
| | geo mean | SD | geo mean | SD | geo mean | SD |
| 33.3 | 8.69 | 0.04242641 | 7.08 | 0.08485281 | 8.24 | 0.11313708 |
| 11.1 | 8.43 | 0.07071068 | 7.005 | 0.09192388 | 8.29 | 0.02828427 |
| 3.7 | 8.125 | 0.16263456 | 6.85 | 0 | 8.01 | 0.05656854 |
| 1.23333333 | 6.815 | 0.64346717 | 6.335 | 0.10606602 | 7.265 | 0.38890873 |
| 0.41111111 | 3.32 | 0.16970563 | 3.41 | 0.33941125 | 3.7 | 0.4384062 |
| 0.13703704 | 1.47 | 0.18384776 | 1.645 | 0.06363961 | 1.595 | 0.23334524 |
| 0.04567901 | 0.72 | 0.05656854 | 0.83 | 0.07071068 | 0.81 | 0.08485281 |
| 0.01522634 | 0.48 | 0.04242641 | 0.535 | 0.0212132 | 0.51 | 0.04242641 |

| c (Ab) | CX_L328C (nM) | | CX_L328C_CP6 (nM) | |
|---|---|---|---|---|
| | geo mean | SD | geo mean | SD |
| 33.30 | 1.925 | 0.0212132 | 1.885 | 0.00707107 |
| 11.10 | 1.89 | 0.01414214 | 1.87 | 0 |
| 3.70 | 1.865 | 0.03535534 | 1.865 | 0.0212132 |
| 1.23 | 1.7 | 0.02828427 | 1.735 | 0.03535534 |
| 0.41 | 1.035 | 0.09192388 | 1.15 | 0.05656854 |
| 0.14 | 0.61 | 0.01414214 | 0.685 | 0.03535534 |
| 0.05 | 0.455 | 0.0212132 | 0.465 | 0.0212132 |
| 0.02 | 0.485 | 0.0212132 | 0.39 | 0 |

TABLE 11

Internalization into MB-MDA468 cell line of CX_N325C mutant.

|     |              | unstained | no int | 1 h    | 3 h    | 12 h   | 24 h   | 48 h   |
|-----|--------------|-----------|--------|--------|--------|--------|--------|--------|
| MFI | quenched     |           | 1.66   | 5.24   | 8.44   | 18.53  | 25.61  | 33.285 |
|     | not quenched | 0.34      | 17.695 | 22.39  | 23.765 | 32.775 | 37.1   | 44.27  |
| SD  | quenched     |           | 0      | 0.03   | 0.08   | 0.14   | 0.51   | 0.395  |
|     | not quenched | 0.01      | 0.165  | 0.07   | 0.025  | 0.135  | 0.3    | 0.01   |
|     | fraction internalized (%) |  |      | 17.3   | 30.7   | 54.2   | 67.6   | 74.2   |

TABLE 12

Internalization into MB-MDA468 cell line of CX_L328C mutant

|     |              | unstained | no int | 1 h    | 3 h    | 12 h   | 24 h   | 48 h   |
|-----|--------------|-----------|--------|--------|--------|--------|--------|--------|
| MFI | quenched     | 0.38      | 1.79   | 5.865  | 8.16   | 16.35  | 25.41  | 31.5   |
|     | not quenched |           | 19.225 | 25.24  | 25.73  | 32.925 | 40.255 | 45.16  |
| SD  | quenched     | 0         | 0.01   | 0.015  | 0.02   | 0.19   | 0.03   | 0.34   |
|     | not quenched |           | 0.025  | 0.13   | 0.09   | 0.005  | 0.015  | 0.25   |
|     | fraction internalized (%) |  |      | 0      | 17.4   | 26.6   | 46.8   | 61.4   |

Stabilization of the cysteine substituted mutants was performed by introducing a stabilization mutation Ala378Val using Quikchange site-directed mutagenesis kit and primers p378vfor and p378vrev. Protein production, coupling with maleimide-Alexafluor488 and cell binding assay was performed as described above.

TABLE 13

| P378vfor | GCTTCTATCCCAGCGATATCGTGGTGGAGTGGGA GAGCAATGGGCAGC SEQ ID NO: 58 |
|----------|------|
| P378vrev | GCTGCCCATTGCTCTCCCACTCCACCACGATATC GCTGGGATAGAAGC SEQ ID NO: 59 |

TABLE 14

Binding of Ala378Val single cysteine substituted mutants to MB-MDA468 cell line

|              | CX_N325C_A378V | | CX_L328C_A378V | |
|--------------|----------|-------|----------|-------|
| c (Ab)       | geo mean | SD    | geo mean | SD    |
| 10           | 7.185    | 0.065 | 4.965    | 0.025 |
| 3.33333333   | 6.97     | 0.03  | 4.805    | 0.005 |
| 1.11111111   | 7.03     | 0.02  | 4.77     | 0.07  |
| 0.37037037   | 5.8      | 0.39  | 4.415    | 0.035 |
| 0.12345679   | 2.27     | 0.15  | 1.805    | 0.005 |
| 0.04115226   | 0.935    | 0.065 | 0.81     | 0.01  |
| 0.01371742   | 0.505    | 0.015 | 0.47     | 0     |
| 0.00457247   | 0.34     | 0.02  | 0.32     | 0     |

Example 6: Double Cysteine Mutant CX Asn325CysLeu328Cys

Cysteine residues were introduced at both targeted positions in one molecule using CX_N325C construct as a template and using primers DDS328 and DDS328A to construct the mutant CX_N325CL328C. A CysP6-stabilized variant was constructed using primers CXP271C1 and CXP271C2 as well as CXR292C1 and CXR292C2.

Binding of cell-bound antigen was comparable to the parental antibody. Because of several modifications in the $C_H2$ domain the mutant CX_Asn325CysLeu328Cys_CysP6 was examined for binding to FcRn using biolayer interferometry. Its binding constant was found to be comparable with wild-type cetuximab when dissociation was performed at pH 5.8 ($5.2 \times 10^{-8}$ vs. $7.2 \times 10^{-8}$ nM) and its pH-dependent FcRn binding was retained.

TABLE 15

| DDS328 | GGTGAGCTGTAAGGCCTGTCCTGCCCCCATCGAG SEQ ID NO: 60 |
| --- | --- |
| DDS328A | CTCGATGGGGGCAGGACAGGCCTTACAGCTCACC SEQ ID NO: 61 |

Heavy chain constructs were mixed with CX light chain construct in 1:1 mass ration and transfected into CHO—S cells according to the standard protocols. 30 ml CHO—S cells was transfected at a density of $1\times10^6$/ml with a mixture of 37.5 µg DNA, 37.5 µl MAX reagent, each diluted in 600 µl Opti-Pro medium. After cultivation at 37° C. for 7 days, under 5% CO2 in humidified atmosphere, supernatants were harvested and proteins isolated using Protein A purification. Briefly, supernatants were buffered with 0.1 M Na-phosphate for binding to Protein A Hi-Trap column, eluted with pH shift to 3.5 with 0.1M glycine and neutralized immediately with 2M Tris. After extensive dialysis in PBS, proteins were stored at −80° C.

Mutants were labelled by incubation with maleimide-Alexafluor488 and dialysed extensively against PBS to remove the unreacted reagent. Their level of binding to the strongly EGFR-positive cells MB-MDA468 and A431 was estimated in comparison with cetuximab coupled with Alexafluor488 via lysine residues using NHS-coupling chemistry using FACS experiment. Cells were harvested and resuspended at a density of $1\times10^6$ cells/ml in 2% BSA-PBS. Staining was performed in 96-well plates with 100 000 cells/well. Cells were blocked for 30 min on ice and then incubated with primary antibodies coupled with Alexafluor488 in 3-fold dilution series in 2% BSA-PBS starting from 10 nM on ice for 30 min. Before analysis, the cells were resuspended in 200 µl PBS with 7-AAD diluted 1:100 and kept on ice. Mean fluorescent intensity of live cell population was determined. High fluorescent signal indicated successful coupling of maleimide-derivatized fluorophore with cysteine residues.

All cysteine-stabilized mutants as well as CX_Asn325CysLeu328Cys and CX_Asn325CysLeu328Cys_CysP6 were tested for the amenability of toxin coupling. MAL-Val-Cit-MMAE was dissolved in DMSO at 1 mg/mL and incubated with the mutants at a molar ratio of 8 toxins per 1 antibody molecule. After extensive dialysis, protein preparations were analyzed for their profile in SEC in native conditions. SEC was performed on a Superdex HiLoad 16/600 Superdex 200 pg with PBS/0.2M NaCl as a mobile phase with Bio-Rad molecular weight standards as protein size indicators. Analysed mutants were found to be free of aggregate.

The migration pattern in hydrophobic interaction chromatography (HIC) column of substituted mutants was examined. The chromatography was performed on a Proteomix Ethyl-NP5 4.6×100 mm Sepax column using a gradient from 1.5 to 0 M $(NH_4)_2SO_4$ in 25 mM Tris, pH 7.5 buffer. The mutant CX_Asn325CysLeu328Cys eluted significantly later than the uncoupled protein, indicating the increased interaction of the coupled protein with column matrix. Mass spectrometry analysis has shown a mix of species of protein coupled either with 0, 1 or 2 toxin molecules. See FIGS. 2 and 3.

Further, the CysP6-stabilized single substituted mutants and the double mutants CX_Asn325CysLeu328Cys and CX_Asn325CysLeu328Cys_CysP6 were tested for cytotoxicity to MB-MDA468 and A431 cell lines and HEK293-6E as a negative cell line in a WST-1 proliferation assay. Cells were seeded into 96-well plates at 10000 cells/well in 100 µl DMEM with 10% FCS and penicillin/streptomycin and allowed to attach overnight in humidified atmosphere under 5% $CO_2$. Toxin conjugates and unconjugated proteins were added in a 5-fold dilution series starting from 10 µg/mL and incubated for 5 days. Although all mutants exhibited a degree of specific cytotoxicity towards target cells, CX_Asn325CysLeu328Cys was most potent and could cause a reduction of proliferation of EGFR-positive cell line MB-MDA468 to 17.5% and A431 to 24.5% in comparison with the untreated control. Protein preparation without the coupled toxin had no effect on cell proliferation and the conjugated compound had no effect on the control cell line HEK293-6E with a low EGFR expression.

TABLE 16

| | CX_N325C_L328C | | CX_N325C_L328C_CP6 | |
| --- | --- | --- | --- | --- |
| c (Ab) (µg/ml) | geo mean | SD | geo mean | SD |
| 10 | 5.1 | 0.07 | 8.31 | 0.07 |
| 3.333333333 | 4.905 | 0.035 | 8.045 | 0.045 |
| 1.111111111 | 4.945 | 0.015 | 8.055 | 0.005 |
| 0.37037037 | 4.12 | 0.07 | 6.64 | 0.02 |
| 0.12345679 | 2.04 | 0.14 | 2.89 | 0.04 |
| 0.041152263 | 0.84 | 0.04 | 1.145 | 0.005 |
| 0.013717421 | 0.455 | 0.005 | 0.58 | 0.01 |
| 0.004572474 | 0.315 | 0.005 | 0.37 | 0.01 |

TABLE 17

The effect of CX__Asn325CysLeu328Cys__mal__val__cit__MMAE on the proliferation of A431 cell line

| | Ab (nM) | 66.6000 | 13.3200 | 2.6640 | 0.5328 | 0.1066 | 0.0213 | 0.0043 | 0.0009 | 0.0002 |
|---|---|---|---|---|---|---|---|---|---|---|
| Cetuximab | % control | 96.45 | 92.54 | 91.86 | 98.42 | 87.05 | 114.85 | 94.31 | 108.13 | 97.83 |
| | SD | 10.56 | 7.67 | 4.72 | 2.19 | 1.98 | 25.40 | 0.90 | 7.68 | 0.78 |
| CX__N325CL328C mal-val-cit-MMAE | % control | 24.46 | 44.94 | 61.09 | 96.79 | 104.05 | 108.41 | 114.98 | 97.49 | 98.32 |
| | SD | 1.17 | 2.58 | 0.62 | 1.40 | 3.42 | 2.32 | 3.20 | 1.05 | 0.39 |

TABLE 18

The effect of CX__Asn325CysLeu328Cys__mal__val__cit__MMAE on the proliferation of MB-MDA468 cell line

| | Ab (nM) | 66.600 | 13.320 | 2.664 | 0.533 | 0.107 | 0.021 | 0.004 | 0.001 | 0.000 |
|---|---|---|---|---|---|---|---|---|---|---|
| Cetuximab | % control | 68.75 | 81.081 | 90.74 | 97.14 | 99.54 | 98.1 | 99.61 | 101 | 100.5 |
| | SD | 0.3323 | 1.9788 | 0.128 | 0.804 | 0.202 | 0.72 | 0.682 | 1.305 | 1.803 |
| CX__N325CL328Cmal-val-cit-MMAE | % control | 17.521 | 29.776 | 32.83 | 74.01 | 96.71 | 99.92 | 98.44 | 97.05 | 103 |
| | SD | 3.1701 | 1.9024 | 0.281 | 0.153 | 0.441 | 3.288 | 1.53 | 0.201 | 2.338 |

TABLE 19

The effect of CX__Asn325CysLeu328Cys__mal__val__cit__MMAE on the proliferation of HEK293-6E cell line

| | Ab (nM) | 66.600 | 13.320 | 2.664 | 0.533 | 0.107 | 0.021 | 0.004 | 0.001 | 0.000 |
|---|---|---|---|---|---|---|---|---|---|---|
| Cetuximab | % control | 98.30 | 99.53 | 100.20 | 103.35 | 102.76 | 98.75 | 104.13 | 105.82 | 98.79 |
| | SD | 0.40 | 0.07 | 0.13 | 0.13 | 0.17 | 0.99 | 1.18 | 1.70 | 0.17 |
| CX__N325CL328Cmal-val-cit-MMAE | % control | 93.94 | 102.09 | 99.58 | 103.03 | 97.87 | 97.15 | 100.36 | 102.39 | 100.70 |
| | SD | 1.65 | 0.86 | 1.35 | 3.89 | 0.71 | 0.54 | 0.07 | 4.54 | 1.26 |

Example 7: IgG1/2 NQ Mutants

Single mutations Asn325Cys and Leu328Cys were probed in combination with chosen stabilization mutations for functionalization of the antibody format optimized for silencing of effector function CX-IgG1/2NQ (SEQ ID NO:58, SEQ ID NO:59). Additionally, the variant hu225M-IgG1/2NQ (sequences below) was used.

```
Amino acid sequence of CX IgG1/2NQ heavy chain
(the first 19 amino acids, leader peptide
underlined)
SEQ ID NO: 62:
MAVLGLLFCLVTFPSCVLSQVQLKQSGPGLVQPSQSLSITCTVSGFSLTN

YGVHWVRQSPGKGLEWLGVIWSGGNTDYNTPFTSRLSINKDNSKSQVFFK

MNSLQSNDTAIYYCARALTYYDYEFAYWGQGTLVTVSAASTKGPSVFPLA

PCSRSTSESTAALGCLVKDYFPEPVTVSWNSGALTSGVHTFPAVLQSSGL

YSLSSVVIVPSSNFGTQTYTCNVDHKPSNIKVDKTVEPKSSDKTHTCPPC

PAPPVAGPSVFLFPPKPKDTLMISRTPEVICVVVDVSHEDPEVQFNWYVD

GVEVHNAKTKPREEQAQSTFRVVSVLTVVHQDWLNGKEYKCAVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPG
```

```
-continued
Nucleotide sequence of CX IgG1/2NQ heavy chain
SEQ ID NO: 63:
ATGGCTGTCTTGGGGCTGCTCTTCTGCCTGGTGACATTCCCAAGCTGTGT

CCTATCCCAGGTGCAGCTGAAGCAGTCAGGACCTGGCCTAGTGCAGCCCT

CACAGAGCCTGTCCATCACCTGCACAGTCTCTGGTTTCTCATTAACTAAC

TATGGTGTACACTGGGTTCGCCAGTCTCCAGGAAAGGGTCTGGAGTGGCT

GGGAGTGATATGGAGTGGTGGAAACACAGACTATAATACACCTTTCACAT

CCAGACTGAGCATCAACAAGGACAATTCCAAGAGCCAAGTTTTCTTTAAA

ATGAACAGTCTGCAATCTAATGACACAGCCATATATTACTGTGCCAGAGC

CCTCACCTACTATGATTACGAGTTTGCTTACTGGGGCCAAGGGACTCTGG

TCACTGTCTCTGCAGCTAGCACCAAGGGCCCATCGGTCTTCCCCCTGGCG

CCCTGCTCCAGGAGCACCTCCGAGAGCACAGCGGCCCTGGGCTGCCTGGT

CAAGGACTACTTCCCCGAACCGGTGACGGTGTCGTGGAACTCAGGCGCTC

TGACCAGCGGCGTGCACACCTTCCCAGCTGTCCTACAGTCCTCAGGACTC

TACTCCCTCAGCAGCGTGGTGACCGTGCCCTCCAGCAACTTCGGCACCCA

GACCTACACCTGCAACGTAGATCACAAGCCCAGCAACACCAAGGTGGACA

AGACAGTTGAGCCCAAATCTTCTGACAAAACTCACACATGCCCACCGTGC

CCAGCACCACCTGTGGCAGGACCGTCAGTCTTCCTCTTCCCCCCAAAACC
```

```
CAAGGACACCCTCATGATCTCCCGGACCCCTGAGGTCACGTGCGTGGTGG

TGGACGTGAGCCACGAAGACCCCGAGGTCCAGTTCAACTGGTACGTGGAC

GGCGTGGAGGTGCATAATGCCAAGACAAAGCCACGGGAGGAGCAGGCCCA

GAGCACGTTCCGTGTGGTCAGCGTCCTCACCGTTGTGCACCAGGACTGGC

TGAACGGCAAGGAGTACAAGTGCGCTGTCTCCAACAAAGGCCTCCCAGCC

CCCATCGAGAAAACCATCTCCAAAACCAAAGGGCAGCCCCGAGAACCACA

GGTGTACACCCTGCCCCCATCACGGGAGGAGATGACCAAGAACCAGGTCA

GCCTGACCTGCCTGGTCAAAGGCTTCTACCCCAGCGACATCGCCGTGGAG

TGGGAGAGCAATGGGCAGCCGGAGAACAACTACAAGACCACACCTCCCAT

GCTGGACTCCGACGGCTCCTTCTTCCTCTACAGCAAGCTCACCGTGGACA

AGAGCAGGTGGCAGCAGGGGAACGTCTTCTCATGCTCCGTGATGCATGAG

GCTCTGCACAACCACTACACGCAGAAGAGCCTCTCCCTGTCCCGGGT
```

Amino acid sequence of hu225M-IgG1/2NQ heavy
chain (the first 19 amino acids, leader peptide
underlined)
SEQ ID NO: 64:
<u>MKLPVRLLVLMFWIPASLS</u>EVQLVQSGAEVKKPGASVKVSCKASGFSLTN

YGVHWMRQAPGQGLEWIGVIWSGGNTDYNTPFTSRVTITSDKSTSTAYME

LSSLRSEDTAVYYCARALTYYDYEFAYWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

Nucleotide sequence of hu225M-IgG1/2NQ heavy
chain
SEQ ID NO: 65:
```
GAGGTCCAATTGGTGCAGTCTGGAGCTGAGGTGAAGAAGCCTGGAGCTTC

AGTGAAGGTGTCCTGCAAAGCTTCTGGATTCTCATTAACTAACTATGGTG

TACACTGGATGCGTCAGGCTCCTGGGCAGGGTCTCGAGTGGATTGGAGTG

ATATGGAGTGGTGGAAACACAGACTATAATACACCTTTCACATCCAGAGT

CACAATCACTTCAGACAAATCCACCAGCACAGCCTACATGGAGCTCAGCA

GCCTGAGGTCTGAGGACACTGCGGTCTATTACTGTGCAAGAGCCCTCACC

TACTATGATTACGAGTTTGCTTACTGGGGTCAAGGCACCCTGGTCACAGT

CTCCTCAGCCTCCACCAAGGGCCCATCGGTCTTCCCCCTGGCACCCTCCT

CCAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAGT

TGAGCCCAAATCTTGTGACAAAACTCACACATGCCCACCGTGCCCAGCAC

CTGAACTCCTGGGGGGACCGTCAGTCTTCCTCTTCCCCCCAAAACCCAAG
```

```
GACACCCTCATGATCTCTAGAACCCCTGAGGTCACATGCGTGGTGGTGGA

CGTGAGCCACGAAGACCCTGAGGTCAAGTTCAACTGGTACGTGGACGGCG

TGGAGGTGCATAATGCCAAGACAAAGCCGCGGGAGGAGCAGTACAACAGC

ACGTACCGTGTGGTCAGCGTCCTCACCGTCCTGCACCAGGACTGGCTGAA

TGGCAAGGAGTACAAGTGCAAGGTCTCCAACAAAGCCCTCCCAGCCCCCA

TCGAGAAAACGATATCCAAAGCCAAAGGGCAGCCCCGAGAACCACAGGTG

TACACCCTGCCCCCATCACGGGAGGAGATGACCAAGAACCAGGTCAGCCT

GACCTGCCTGGTCAAAGGCTTCTATCCCAGCGACATCGCCGTGGAGTGGG

AGAGCAATGGGCAGCCGGAGAACAACTACAAGACCACGCCTCCCGTGCTG

GACTCCGACGGCTCCTTCTTCCTCTATAGCAAGCTCACCGTGGACAAGAG

CAGGTGGCAGCAGGGGAACGTCTTCTCATGCTCCGTGATGCATGAGGCTC

TGCACAACCACTACACGCAGAAGAGCCTCTCCCTGTCCCGGGT
```

Amino acid sequence of hu225M light chain (the
first 19 amino acids, leader peptide underlined)
SEQ ID NO: 66:
<u>MKLPVRLLVLMFWIPASLS</u>DIQMTQSPSSLSASVGDRVTITCRASQSIGT

NIHWYQQKPGKAPKLLIKYASESISGVPSRFSGSGYGTDFTLTISSLQPE

DVATYYCQQNYNWPTTFGQGTKVEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

Nucleotide sequence of hu225M light chain
SEQ ID NO: 67:
```
ATGAAGCTTCCTGTTAGGCTGTTGGTGCTGATGTTCTGGATCCCTGCTAG

CTTAAGCGATATCCAGATGACCCAGTCTCCGAGCTCCCTGTCCGCATCTG

TGGGAGACAGAGTCACCATCACTTGCAGGGCCAGTCAGAGTATTGGCACA

AACATACACTGGTATCAGCAGAAGCCAGGGAAAGCTCCTAAGCTTCTTAT

TAAGTATGCTTCTGAGTCTATCTCTGGAGTCCCATCCCGATTCTCCGGAA

GTGGCTATGGTACAGATTTTACTCTCACAATTAGCAGCCTGCAGCCTGAA

GATGTTGCAACTTACTACTGTCAACAAAATTATAACTGGCCAACCACGTT

TGGCCAAGGTACCAAGGTGGAAATAAAACGTACGGTGGCTGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT
```

The mutations Asn325Cys and Leu328Cys were introduced into the hu225M-IgG1/2NQ using primers listed in the Table below. The double mutant hu225M-IgG1/2NQ was constructed by mutagenizing the construct with Asn325Cys mutation using primers NQN3253CL28C and NQN325CL328CA.

TABLE 20

| | |
|---|---|
| NQN325C | CAAGTGCGCTGTCTCCTGCAAAGGCCTCCCAGC SEQ ID NO: 68 |
| NQN325CA | GCTGGGAGGCCTTTGCAGGAGACAGCGCACTTG SEQ ID NO: 69 |
| NQL328C | GTCTCCAACAAAGGCTGCCCAGCCCCCATCGAG SEQ ID NO: 70 |
| NQL328CA | CTCGATGGGGGCTGGGCAGCCTTTGTTGGAGAC SEQ ID NO: 71 |
| NQN325CL328C | GTCTCCTGCAAAGGCTGCCCAGCCCCCATCGAG SEQ ID NO: 72 |
| NQN325CL328CA | CTCGATGGGGGCTGGGCAGCCTTTGCAGGAGAC SEQ ID NO: 73 |
| NQA378V | TACCCCAGCGACATCGTGGTGGAGTGGGAGAGC SEQ ID NO: 74 |
| NQA378VA | GCTCTCCCACTCCACCACGATGTCGCTGGGGTA SEQ ID NO: 75 |
| NQP1C | GTGAGCCACGAAGACTGCGAGGTCCAGTTCAAC SEQ ID NO: 76 |
| NQP1CA | GTTGAACTGGACCTCGCAGTCTTCGTGGCTCAC SEQ ID NO: 77 |
| NQR2C | GCCAAGACAAAGCCATGCGAGGAGCAGGCCCAG SEQ ID NO: 78 |
| NQR2CA | CTGGGCCTGCTCCTCGCATGGCTTTGTCTTGGC SEQ ID NO: 79 |

Each variant was expressed as a stabilized mutant, once with the combination of Pro271Cys/Arg292Cys (CysP6) mutations, which was introduced using primers NQP1C and NQP1CA as well as NQR2C and NQR2CA, and once with the Ala378Val mutation, which was introduced using primers NQA378V and NQA378VA. This particular stabilization motive, structurally located in the N-terminal loops of the $C_H3$ domain, was inferred from FoldX algorithm and confirmed to improve the Tm of the $C_H2$ domain for 3° C. Mutants were expressed in ExpiCHO cells according to MaxTiter protocol. After ProteinA purification, the yields of hu225M variants were between 18.4 and 57.7 mg/L. Only for the mutants stabilized with Ala378Val motif the amount of homodimer in SEC in native conditions amounted to more than 90%. Alexafluor488-maleimide labelling has resulted in an efficient coupling to single cysteine substituted mutants, for which binding to EGFR-positive cell line MB-MDA468 could be observed.

TABLE 21

| | 255_IgG1/2NQ_N325C | | 225_IgG1/2NQ_L328C | |
|---|---|---|---|---|
| c (Ab) (µg/ml) | geo mean | SD | geo mean | SD |
| 10 | 7.83 | 0.07 | 4.67 | 0.01 |
| 3.33333333 | 7.605 | 0.005 | 4.515 | 0.005 |
| 1.11111111 | 7.52 | 0.12 | 4.455 | 0.045 |
| 0.37037037 | 6.635 | 0.085 | 3.965 | 0.085 |
| 0.12345679 | 3.37 | 0.01 | 2.135 | 0.035 |
| 0.04115226 | 1.35 | 0 | 0.915 | 0.005 |
| 0.01371742 | 0.715 | 0.005 | 0.535 | 0.005 |
| 0.00457247 | 0.44 | 0 | 0.38 | 0 |

Example 8: SEED Mutants

Mutations Asn325Cys and Leu328Cys were introduced into the $C_H2$ domain of a bispecific anti-EGFR/anti-c-MET antibody, where heterodimerization is achieved using SEED technology. In this molecule, the EGFR-specific antibody hu225M is expressed as a single chain fragment on the GA-chain and an unmodified c-MET-specific Fab fragment is fused with the AG-chain of the heterodimeric Fc. Primers used with the Quikchange mutagenesis kit to introduce the mutations Asn325Cys and Leu328Cys are listed in the table below. Proteins were expressed in ExpiCHO cells according to the MaxTiter protocol. The expression yield in ExpiCHO cells amounted to 120 mg/L for the wild-type after protein A purification and the aggregated material could be removed by a single step of preparative SEC filtration. The single substituted variants were coupled with mal-val-cit-MMAE. HIC analysis revealed efficient coupling of toxin to the Asn325Cys SEED mutant. See FIG. 4.

Protein sequence of 225M scFv_GA chain (the first 19 amino acids, leader peptide underlined)
SEQ ID NO: 80
MKLPVRLLVLMFWIPASLSEVQLVQSGAEVKKPGASVKVSCKASGFSLTN

YGVHWMRQAPGQGLEWIGVIWSGGNTDYNTPFTSRVTITSDKSTSTAYME

LSSLRSEDTAVYYCARALTYYDYEFAYWGQGTLVTVSSGGGGSGGGGSGG

GGSDIQMTQSPSSLSASVGDRVTITCRASQSIGTNIHWYQQKPGKAPKLL

IKYASESISGVPSRFSGSGYGTDFTLTISSLQPEDVATYYCQQNYNWPTT

FGQGTKVEIKSSGPGVEPKSSDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPPSEELALNELVTLTCLVKGFYPSDIAVEWLQGSQELPREKYLTWAP

VLDSDGSFFLYSILRVAAEDWKKGDTFSCSVMHEALHNHYTQKSLDRSPG

K.

Nucleotide sequence of 225 scFv_GA heavy chain
SEQ ID NO: 81
ATGAAGCTTCCTGTTAGGCTGTTGGTGCTGATGTTCTGGATCCCTGCTAG

CTTAAGCGAGGTCCAATTGGTGCAGTCTGGAGCTGAGGTGAAGAAGCCTG

GAGCTTCAGTGAAGGTGTCCTGCAAAGCTTCTGGATTCTCATTAACTAAC

TATGGTGTACACTGGATGCGTCAGGCTCCTGGGCAGGGTCTCGAGTGGAT

TGGAGTGATATGGAGTGGTGGAAACACAGACTATAATACACCTTTCACAT

CCAGAGTCACAATCACTTCAGACAAATCCACCAGCACAGCCTACATGGAG

CTCAGCAGCCTGAGGTCTGAGGACACTGCGGTCTATTACTGTGCAAGAGC

CCTCACCTACTATGATTACGAGTTTGCTTACTGGGGTCAAGGCACCCTGG

TCACAGTCTCCTCGGGAGGTGGAGGTTCTGGAGGTGGCGGATCCGGAGGT

GGCGGTTCTGATATCCAGATGACCCAGTCTCCGAGCTCCCTGTCCGCATC

TGTGGGAGACAGAGTCACCATCACTTGCAGGGCCAGTCAGAGTATTGGCA

CAAACATACACTGGTATCAGCAGAAGCCAGGGAAAGCTCCTAAGCTTCTT

ATTAAGTATGCTTCTGAGTCTATCTCTGGAGTCCCATCCCGATTCTCCGG

AAGTGGCTATGGTACAGATTTTACTCTCACAATTAGCAGCCTGCAGCCTG

AAGATGTTGCAACTTACTACTGTCAACAAAATTATAACTGGCCAACCACG

TTTGGCCAAGGTACCAAGGTGGAAATAAAATCTTCCGGTCCTGGAGTGGA

GCCTAAATCTTCTGACAAAACTCACACGTGCCCACCGTGCCCAGCACCTG

```
AACTCCTGGGGGACCGTCAGTCTTCCTCTTCCCCCCAAAACCCAAGGAC

ACCCTCATGATCTCTAGAACCCCTGAGGTCACATGCGTGGTGGTGGACGT

GAGCCACGAAGACCCTGAGGTCAAGTTCAACTGGTACGTGGACGGCGTGG

AGGTGCATAATGCCAAGACAAAGCCGCGGGAGGAGCAGTACAACAGCACG

TACCGTGTGGTCAGCGTCCTCACCGTCCTGCACCAGGACTGGCTGAATGG

CAAGGAGTACAAGTGCAAGGTCTCCAACAAAGCCCTCCCAGCCCCCATCG

AGAAAACGATATCCAAAGCCAAAGGGCAGCCCCGAGAACCACAGGTGTAC

ACCCTGCCCCCACCGTCGGAGGAGCTGGCCCTGAACGAGCTGGTGACGCT

GACCTGCCTGGTCAAAGGCTTCTATCCCAGCGACATCGCCGTGGAGTGGG

TGCAGGGGTCCCAGGAGCTGCCCCGCGAGAAGTACCTGACTTGGGCACCC

GTGCTGGACTCCGACGGCTCCTTCTTCCTCTATAGTATACTGCGCGTGGC

AGCCGAGGACTGGAAGAAGGGGGACACCTTCTCATGCTCCGTGATGCATG

AGGCTCTGCACAACCACTACACGCAGAAGAGCCTCGACCGCTCCCCGGGT

AAA.

Protein sequence of B10v5_AG heavy chain (the
first 20 amino acids, leader peptide underlined)
                                    SEQ ID NO: 82
METDTLLLWVLLLWVPGSTGEVQLVQSGGGLVQPGGSLRLSCAASGFTFS

SYAMSWVRQAPGKGLEWVSAISGSGGSTYYADSVKGRFTISRDNSKNTLY

LQMNSLRAEDTAVYYCAKDRRITHTYWGQGTLVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKRVEPKSCDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPFRPEVHLLPPSREEMTKNQVSLTCLARGFYPKDIAVE

WESNGQPENNYKTTPSRQEPSQGTTTFAVTSKLTVDKSRWQQGNVFSCSV

MHEALHNHYTQKTISLSPGK.

Nucleotide sequence of B10v5_AG heavy chain
                                    SEQ ID NO: 83
ATGGAGACCGACACCCTGCTGCTGTGGGTGCTGCTGCTGTGGGTGCCCGG

GTCGACCGGCGAAGTGCAGCTGGTGCAGTCTGGGGGAGGCTTGGTACAGC

CTGGGGGGTCCCTGAGACTCTCCTGTGCAGCCTCTGGATTCACCTTTAGC

AGCTATGCCATGAGCTGGGTCCGCCAGGCTCCAGGGAAGGGGCTGGAGTG

GGTCTCAGCTATTAGTGGTAGTGGTGGTAGCACATACTACGCAGACTCCG

TGAAGGGCCGGTTCACCATCTCCAGAGACAATTCCAAGAACACGCTGTAT

CTGCAAATGAACAGCCTGAGAGCCGAGGACACGGCCGTATATTACTGTGC

GAAAGATCGGCGTATTACCCACACCTACTGGGGCCAGGGAACCCTGGTCA

CCGTCTCCTCAGCTAGCACCAAGGGCCCATCGGTCTTCCCCCTGGCACCC

TCCTCCAAGAGCACCTCTGGGGGCACAGCGGCCCTGGGCTGCCTGGTCAA

GGACTACTTCCCCGAACCGGTGACGGTGTCGTGGAACTCAGGCGCCCTGA

CCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGAC

CTACATCTGCAACGTGAATCACAAGCCCAGCAACACCAAGGTGGACAAGA

GAGTTGAGCCCAAATCTTGTGACAAAACTCACACATGCCCACCGTGCCCA

GCACCTGAACTCCTGGGGGGACCGTCAGTCTTCCTCTTCCCCCCAAAACC

CAAGGACACCCTCATGATCTCCCGGACCCCTGAGGTCACATGCGTGGTGG

TGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGC

TGAATGGCAAGGAGTACAAGTGCAAGGTCTCCAACAAAGCCCTCCCAGCC

CCCATCGAGAAAACGATATCCAAAGCCAAAGGGCAGCCCTTCCGGCCAGA

GGTCCACCTGCTGCCCCCATCACGGGAGGAGATGACCAAGAACCAGGTCA

GCCTGACCTGCCTGGCACGCGGCTTCTATCCCAAGGACATCGCCGTGGAG

TGGGAGAGCAATGGGCAGCCGGAGAACAACTACAAGACCACGCCTTCCCG

GCAGGAGCCCAGCCAGGGCACCACCACCTTCGCTGTGACCTCGAAGCTCA

CCGTGGACAAGAGCAGATGGCAGCAGGGGAACGTCTTCTCATGCTCCGTG

ATGCATGAGGCTCTGCACAACCACTACACGCAGAAGACCATCTCCCTGTC

CCCGGGTAAA.

Protein sequence of B10v5 light chain (the first
20 amino acids, leader peptide underlined)
                                    SEQ ID NO: 84
METDTLLLWVLLLWVPGSTGEPVLTQPPSVSVAPGETATIPCGGDSLGSK

IVHWYQQRPGQAPLLVVYDDAARPSGIPERFSGSKSGTTATLTISSVEAG

DEADYFCQVYDYHSDVEVFGGGTKLTVLGQPKAAPSVTLFPPSSEELQAN

KATLVCLISDFYPGAVTVAWKADSSPVKAGVETTTPSKQSNNKYAASSYL

SLTPEQWKSHKSYSCQVTHEGSTVEKTVAPTECS.
```

TABLE 22

| | |
|---|---|
| SEEDN325C | CAAGTGCAAGGTCTCCTGTAAAGCCCTCCCAGCC<br>SEQ ID NO: 85 |
| SEEDN325CA | GGCTGGGAGGGCTTTACAGGAGACCTTGCACTTG<br>SEQ ID NO: 86 |
| SEEDL328C | GTCTCCAACAAAGCCTGCCCAGCCCCCATCGAG<br>SEQ ID NO: 87 |
| SEEDL328CA | CTCGATGGGGCTGGGCAGGCTTTGTTGGAGAC<br>SEQ ID NO: 88 |

TABLE 23

| Correspondence for names and numbers of the mutant proteins | | |
|---|---|---|
| EU numbering | EU numbering | IMGT numbering |
| S324C | Ser324Cys | S107C |
| N325C | Asn325Cys | N108C |
| K326C | Lys326Cys | K109C |
| A327C | Ala327Cys | A110C |
| L328C | Leu328Cys | L113C |
| P329C | Pro329Cys | P114C |
| A330C | Ala330Cys | A115C |
| T250V | Thr250Val | T14V |
| P271C | Pro271Cys | P35C |
| R292C | Arg292Cys | R83C |
| A378V | Ala378Val | A38V |

Example 9: Single Cysteine Substituted Mutants in IgG Format (Cetuximab Framework)

Expression and Stabilization Strategies

By screening the amino-acid residues of the FG-loop of the $C_H2$ domain, two positions, Asn325 and Leu328, were discovered which in an Fc fragment allowed mutagenesis to a cysteine residue that could be coupled to maleimide-derivatized toxin or a surrogate reporter molecule. The Fc fragments modified in this way still expressed well and exhibited a monomeric profile in SEC in native conditions. Analogous mutants of cetuximab (CX) antibody were constructed. To account for destabilization of the $C_H2$-domain, the stabilization mutation Thr250Val and a double mutation Pro271Cys/Arg292Cys was introduced, which leads to a formation of a de novo cysteine bond, here termed CysP6. Thr250Val is derived from FoldX algorithm (Schymkowitz J, Borg J, Stricher F, Nys R, Rousseau F, Serrano L. The FoldX web server: an online force field. Nucleic Acids Res. 2005; 33 (Web Server issue):W382-388) and shown to stabilize the $C_H2$ domain of the Fc fragment by shifting its Tm for 9° C., whereas CysP6 was derived from DSDbase algorithm (Vinayagam A, Pugalenthi G, Rajesh R, Sowdhamini R. DSDBASE: a consortium of native and modelled disulphide bonds in proteins. Nucleic Acids Res. 2004; 32 (Database issue):D200-202.) and proven to stabilize the $C_H2$ domain by 9° C. When combined with single cysteine mutants, the mutation Thr250Val proved detrimental to the expression level, in the case of Leu328Cys to an extent that prevented further characterization. All other mutants could be expressed and purified at a high level in HEK293-6E system, however their amenability for cysteine-linked coupling, especially for the mutant Leu328Cys, was low. The mutants expressed by CHO cells were next assessed. For all Leu328Cys substituted variants, model coupling with maleimide-Alexafluor488 conjugate (described in the paragraph below) was more efficient with CHO-expressed protein. For a more profound characterization, mutants were expressed in ExpiCHO system that delivered about 300 mg/L protein after Protein A purification and gel filtration.

Model Coupling with Alexafluor 488, Cell Binding and Internalization Assays

First, the single cysteine substituted mutants of cetuximab were coupled with maleimide-derivatized Alexafluor488. Then their binding to the surface of Her1-positive cell lines MB-MDA468 and A431 was examined by exposing the cells to serial dilutions of fluorescently labelled antibodies. The relative level of coupling was assessed according to the fluorescence intensity of the labelled cell population and target antigen binding was estimated after the normalization of the fluorescence readings to the maximal fluorescence intensity. Internalization experiments were performed by quenching the fluorescence of the cell-surface bound fluorophore with an anti-Alexafluor488 quenching antibody (Thermo-Fisher Scientific) and comparing the non-quenched to the quenched sample (Austin C D, De Maziere A M, Pisacane P I, van Dijk S M, Eigenbrot C, Sliwkowski M X, et al. Endocytosis and sorting of ErbB2 and the site of action of cancer therapeutics trastuzumab and geldanamycin. Mol Biol Cell. 2004; 15(12): 5268-5282). Time-course of the internalization was monitored and estimated to be similar to internalization of cetuximab coupled with Alexafluor488 over lysine residues (FIG. 5). Interestingly, internalization proceeded to a lower degree in A431 than in the MB-MDA468 cells.

Toxin Coupling to Cysteine-Substituted Mutants, Mass Spectrometry Analysis and Cellular Assays After initial trials with Alexafluor 488, the antibodies were conjugated to Mal-Val-Cit-MMAE (vedotin) to assess the conjugation efficiency with a representative ADC payload. Using a non-optimized protocol for conjugation, drug to antibody ratios (DAR) of 1:0.74 for CX_Asn325Cys, 1:1.5 for CX_Asn325Cys_CysP6, 1:1.56 for CX_Leu328Cys and 1:5 for CX_Leu328Cys_CysP6 were determined. These ADCs were assessed for targeted cytotoxicity using in vitro cellular assays. Her1 positive cell lines A431 and MDA-MB-468 cells were seeded in multiple well plates and treated with serial dilutions of ADCs and control molecules. After three days of incubation, relative cell viability was assessed by using CellTiter-Glo® Luminescent Cell Viability Assay (Promega) (FIG. 8). All CX-MMAE conjugates showed significantly increased cytotoxicity indicated by low cell viability at lower proteins concentrations compared to control antibodies (unconjugated CX antibody; MMAE-conjugated, HER1 non-binding isotype control antibody DigxMMAE). Cytotoxic small molecules MMAE (without spacer), taxol and doxorubicin served as additional controls.

Cysteine residues were introduced at both targeted positions in one molecule, and also constructed a CysP6-stabilized variant. Binding of cell-bound antigen was comparable to the parental antibody. Because of several modifications in the $C_H2$domain, the mutant CX_Asn325CysLeu328Cys_CysP6 was examined for binding to FcRn using biolayer interferometry. Its binding constant was found to be comparable with wild-type cetuximab when dissociation was performed at pH 5.8 ($5.2 \times 10^{-8}$ vs. $7.2 \times 10^{-8}$ nM) and its pH-dependent FcRn binding was retained (FIG. 6).

Example 10: Determination of the Surface Exposure of Amino Acid Side Chains in Positions that were Mutated to Cysteine The GETAREA program (Fraczkiewicz et al. 1998, J. Comp. Chem., 19, 319-333; accessible online at http://curie.utmb.edu/getarea.html) allows to quickly calculate solvent accessible surface area or solvation energy of proteins. Atomic coordinates of the human IgG1 Fc fragment 1OQO.pdb were supplied to the program as input. A probe radius of 1.4 Angstrom was applied. The output of the program is shown in Table 24.

The contributions from backbone and sidechain atoms are listed in the $4^{th}$ and $5^{th}$ columns, respectively. The next column lists the ratio of side-chain surface area to "random coil" value per residue. The "random coil" value of a residue X is the average solvent-accessible surface area of X in the tripeptide Gly-X-Gly in an ensemble of 30 random conformations. Residues are considered to be solvent exposed if the ratio value exceeds 50% and to be buried if the ratio is less than 20%, marked as "o" and "i" respectively in the last column. The "random coil" values for the 20 amino acids encoded by the standard genetic code are listed in Table 25.

From the results shown in Table 24 it can be seen that the two residues Asn325 and Leu328 are buried ("In").

It surprisingly turned out that such residues, which are buried within the FG loop of the CH2 domain, were suitable for cysteine engineering. In the prior art, suitable sites for Fc site-directed cysteine engineering for drug conjugation were mainly selected based on surface accessibility, see e.g., WO 2017/112624 A1 referring to "residue accessibility", and WO 2014/124316 A2 evaluating all Fc positions for surface accessibility to determine which sites to select for substitution to a cysteine residue. Of note, according to WO 2014/124316 A2 the positions 325 and 328 (EU numbering) were found to be insufficiently surface accessible, and were therefore excluded from cysteine engineering.

TABLE 24

| Residue | Total | Apolar | Backbone | Sidechain | Ratio(%) | In/Out | In/Out |
|---|---|---|---|---|---|---|---|
| GLU | 318 | 75.22 | 9.41 | 1.03 | 74.2 | 52.5 | Oou |
| TYR | 319 | 1.89 | 1.54 | 0 | 1.89 | 1 | In |
| LYS | 320 | 55.37 | 29.21 | 0 | 55.37 | 33.7 | |
| CYS | 321 | 0 | 0 | 0 | 0 | 0 | In |
| LYS | 322 | 51.47 | 13.08 | 0 | 51.47 | 31.3 | |
| VAL | 323 | 0.05 | 0.05 | 0 | 0.05 | 0 | In |
| SER | 324 | 33.41 | 27.41 | 2.89 | 30.52 | 39.4 | |
| ASN | 325 | 8.24 | 4.36 | 8.2 | 0.04 | 0 | In |
| LYS | 326 | 115.54 | 91.15 | 38.51 | 77.03 | 46.8 | |
| ALA | 327 | 39.01 | 27.37 | 23.23 | 15.78 | 24.3 | |
| LEU | 328 | 24.64 | 10.7 | 15.43 | 9.21 | 62 | In |
| PRO | 329 | 147.53 | 118.04 | 47.77 | 99.76 | 94.8 | Out |
| ALA | 330 | 62.76 | 59.05 | 6.7 | 56.06 | 86.4 | Out |
| PRO | 331 | 64.66 | 50.48 | 14.32 | 50.34 | 47.9 | |
| ILE | 332 | 43.92 | 43.92 | 5.51 | 38.42 | 26.1 | |
| GLU | 333 | 89.05 | 26.2 | 20.29 | 68.76 | 48.7 | |
| LYS | 334 | 84.05 | 40.79 | 4.47 | 79.57 | 48.4 | |
| THR | 335 | 65.58 | 38.97 | 20.76 | 44.82 | 42.2 | |
| ILE | 336 | 36.43 | 36.43 | 9.24 | 27.2 | 18.5 | In |
| SER | 337 | 30.99 | 0 | 18.29 | 12.7 | 16.4 | In |
| LYS | 338 | 17.05 | 11.73 | 2.34 | 14.71 | 8.9 | In |

TABLE 25

Random coil values

| | |
|---|---|
| ALA | 64.9 |
| ARG | 195.5 |
| ASN | 114.3 |
| ASP | 113.0 |
| CYS | 102.3 |
| GLN | 143.7 |
| GLU | 141.2 |
| HIS | 154.6 |
| ILE | 147.3 |
| GLY | 87.2 |
| LEU | 146.2 |
| LYS | 164.5 |
| MET | 158.3 |
| PHE | 180.1 |
| PRO | 105.2 |
| SER | 77.4 |
| THR | 106.2 |
| TRP | 224.6 |
| TYR | 193.1 |
| VAL | 122.3 |

Example 11: Single Cysteine Substituted Mutants in IgG Format (Anti HER2 Framework)

Single amino acid substitutions Asn325Cys and Leu328Cys were introduced into the sequences of an HER2 binding antibody derived from trastuzumab (sequences below). DNA strands were de-novo synthesized and cloned onto the mammalian expression vector pTT5 by GeneArt (ThermoFisher, Regensburg). Heavy chain constructs were mixed with the light chain construct and transfected into Expi293 cells (ThermoFisher) according to standard protocols. After cultivation and expression, antibodies were purified by protein A chromatography and the buffer was exchanged to PBS, 1 mM EDTA, pH 7.4.

In order to remove thiol containing molecules that might have formed disulfide bonds with introduced cysteine residues and thereby hamper efficient conjugation, a reduction and re-oxidation procedure was applied. Therefore, antibodies were fully reduced by incubating with 40 molar equivalents TCEP (Tris-(2-carboxyethyl)-phosphine) per antibody at 37° C. for 2 h. Afterwards, buffer was exchanged to PBS, 1 mM EDTA, pH 7.4 and the reduced antibody re-oxidized by applying 20 molar equivalents DHAA (dehydroascorbic acid) at 25° C. for 1.5 h. Conjugation was performed by incubation with 6 molar equivalents mal-val-cit-MMAE for 2-16 h at 25° C. followed by quenching with 25 molar equivalents of N-acetylcysteine. Reaction mixtures were purified by size exclusion chromatography using a Superdex 200 10/300 GL column (GE Healthcare). DAR values were determined by hydrophobic interaction chromatography (HIC) and ESI-MS. For HIC, buffer was adjusted to 0.5 M ammonium sulfate and 40 µg of treated antibody applied onto a pre-equilibrated MAbPac HIC-Butyl column (ThermoFisher) using a standard HPLC system. Samples were eluted using a linear gradient from 75% buffer A (2 M ammonium sulfate, 25 mM Tris-HCl pH 7.5)/25% buffer B (25 mM Tris-HCl, pH 7.5) to 0% A/80% B/20% isopropanol over 20 min and the mAb/ADC signal was monitored using UV absorption at 280 nm.

HIC chromatograms (FIG. 9) show efficient and specific conjugation indicated by a complete shift of the antibody peak towards a distinct peak at later elution times. According to HIC DAR values were 2.0 or slightly higher which was confirmed by mass spectrometry analysis.

To compare the described cysteine positions with other known positions, seven further HER2-binding antibodies with cysteine mutations in the light or heavy chain, namely heavy chain positions D265C, S239C, S400C, K290C, S442C and light chain positions V205C, K183C (all positions according to EU numbering), were introduced into the same HER2 binding, Trastuzumab-like antibody. Antibodies were conjugated as described for the previous anti HER2 antibodies and analyzed by HIC. Afterwards, relative HIC retention times of the ADCs were determined by dividing the HIC retention time (HIC RRT) of the DAR 2 species by the retention time of the respective unconjugated antibodies (Table 26). HIC RRT is an indicator for the hydrophobicity of an ADC and highly depends on the position used for toxin attachment. Low RRT can be an indicator for favorable in vivo characteristics. ADCs conjugated to positions N325C and L328C show RRTs in the lower range compared to the other assessed variants.

Protein sequence of aHER2 light chain (the first
20 amino acids, leader peptide underlined)
SEQ ID NO: 89
METDTLLLWVLLLWVPGSTGDIQMTQSPSSLSASVGDRVTITCRASQDVN

TAVAWYQQKPGKAPKLLIYSASFLYSGVPSRFSGSRSGTDFTLTISSLQP

EDFATYYCQQHYTTPPTFGQGTKVEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC.

Protein sequence of aHER2 heavy chain_N325C (the
first 19 amino acids, leader peptide underlined)
SEQ ID NO: 90
MKLPVRLLVLMFWIPASLSEVQLVESGGGLVQPGGSLRLSCAASGFNIKD

TYIHWVRQAPGKGLEWVARIYPTNGYTRYADSVKGRFTISADTSKNTAYL

QMNSLRAEDTAVYYCSRWGGDGFYAMDYWGQGTLVTVSSASTKGPSVFPL

APSSKSTSGGTAALGCLVKDYFPEPVTVSWNSGALTSGVHTFPAVLQSSG

LYSLSSVVTVPSSSLGTQTYTCNVNHKPSNTKVDKKVEPPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSCKA

LPAPIEKTISKAKGQPREPQVYTLPPSRDELTKNQVSLTCLVKGFYPSDI

AVEWESNGQPENNYKTTPPVLDSDGSFFLYSKLIVDKSRWQQGNVFSCSV

MHEALHNHYTQKSLSLSPGK.

Protein sequence of aHER2 heavy chain_L328C (the
first 19 amino acids, leader peptide underlined)
SEQ ID NO: 91
MKLPVRLLVLMFWIPASLSEVQLVESGGGLVQPGGSLRLSCAASGFNIKD

TYIHWVRQAPGKGLEWVARIYPTNGYTRYADSVKGRFTISADTSKNTAYL

QMNSLRAEDTAVYYCSRWGGDGFYAMDYWGQGTLVTVSSASTKGPSVFPL

APSSKSTSGGTAALGCLVKDYFPEPVTVSWNSGALTSGVHTFPAVLQSSG

LYSLSSVVTVPSSSLGTQTYICNVNHKPSNTKVDKKVEPPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

CPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK.

TABLE 26

| Cysteine position | HIC RRT |
|---|---|
| HC-D265C | 1.12 |
| HC-S239C | 1.18 |
| HC-N325C | 1.25 |
| HC-L328C | 1.26 |
| LC-V205C | 1.30 |
| LC-K183C | 1.32 |
| HC-S400C | 1.38 |
| HC-K290C | 1.39 |
| HC-S442C | 1.70 |

Some embodiments described herein relate to:

1. A specific antigen-binding member (ABM) comprising a specific antigen-binding moiety and an antibody Fc region comprising a CH2 domain, which is engineered for a cysteine substitution at position 108 and/or 113, wherein numbering is according to the IMGT.

2. The ABM of embodiment 1 wherein
a) the antigen-binding moiety is fused to the N-terminus of said antibody CH2 domain; and/or
b) the antigen-binding moiety is comprised in a CH3 domain and/or in the Fc region.

3. The ABM of embodiment 1 or 2, wherein the CH2 domain comprises one or two cysteine substitutions, which are N108C and/or L113C, wherein numbering is according to the IMGT.

4. The ABM of any one of embodiments 1 to 3, wherein the antigen-binding moiety comprises an antigen-binding portion of an antibody, an Fcab, an enzyme, an adhesion protein, a ligand or a ligand binding portion of a receptor.

5. The ABM of any one of embodiments 1 to 4, wherein the antigen-binding moiety is selected from the group consisting of a Fab, F(ab')₂, scFv, Fd, Fv, an antigen-binding CH3, Fcab, and one or more antibody domains comprising at least one antibody binding site in the CDR or non-CDR (or structural) loops.

6. The ABM of any one of embodiments 1 to 5, wherein the antigen-binding moiety is fused to the N-terminus of the CH2 domain via a linker and/or hinge region.

7. The ABM of any one of embodiments 1 to 6, wherein the C-terminus of the CH2 domain is fused to the N-terminus of a CH3 domain, preferably wherein the Fc region is comprised in an antibody Fc consisting of a dimer of antibody heavy chains.

8. The ABM of any one of embodiments 1 to 7, wherein the Fc region is of the IgG, IgA, IgM, or IgE isotype, preferably of a human antibody.

9. The ABM of any one of embodiments 1 to 8, which is an antibody selected from the group consisting of a monoclonal antibody, a bispecific antibody, a multispecific antibody, an antigen-binding part of an antibody, an Fcab molecule, and an antibody comprising an Fcab molecule.

10. The ABM of any one of embodiments 1 to 9, which specifically recognizes a target antigen expressed on the surface of a target cell.

11. An ABM conjugate (ABMC) comprising the ABM of any one of embodiments 1 to 10, and at least one heterologous molecule covalently conjugated to one or both of the cysteines at position 108 and 113 of the CH2 domain, wherein numbering is according to the IMGT.

12. The ABMC of embodiment 11, wherein the heterologous molecule is a substance suitably used in the diagnosis, cure, mitigation, treatment, or prevention of disease, preferably selected from the group consisting of a pharmaceutical drug substance, toxin, radionuclide, immunomodulator, cytokine, lymphokine, chemokine, growth factor, tumor necrosis factor, hormone, hormone antagonist, enzyme, oligonucleotide, DNA, RNA, siRNA, RNAi, microRNA, peptide nucleic acid, photoactive therapeutic agent, anti-angiogenic agent, pro-apoptotic agent, peptide, lipid, carbohydrate, fluorescent tag, visualization peptide, biotin, serum half-life modulator, capture tag, chelating agent, and solid support.

13. The ABMC of embodiment 11 or 12, wherein the heterologous molecule is conjugated to one or both of the cysteines at position 108 and 113 of the CH2 domain via a conjugation linker, wherein numbering is according to the IMGT.

14. The ABMC of embodiment 13, wherein the conjugation linker comprises a maleimide group.

15. An expression system comprising one or more nucleic acid molecules encoding the ABM of any one of embodiments 1 to 10.

16. A host cell comprising the expression system of embodiment 15.

17. A method of preparing the ABM of any one of embodiments 1 to 10, wherein the host cell of embodiment 16 is cultivated or maintained under conditions to produce said ABM.

18. A pharmaceutical preparation comprising the ABM of any of embodiments 1 to 10, or the ABMC of any one of embodiments 11 to 14, and a pharmaceutically acceptable carrier or excipient in a parenteral formulation.

19. A method of producing an ABMC of any one of embodiments 11 to 14, comprising the steps:

a) providing an ABM of any one of embodiments 1 to 10; and b) reacting at least one thiol group of one or both of the cysteines at position 108 and 113 of the CH2 domain with a heterologous molecule by a site-specific conjugation method.

20. The method of embodiment 19, wherein said at least one thiol group is reacting with said heterologous molecule by a Michael reaction, using a conjugation linker comprising a maleimide group.

---

The invention claimed is:

1. An isolated antigen-binding member conjugate comprising
- a specific antigen-binding moiety and an antibody Fc region comprising a human CH2 domain, having an engineered cysteine substitution at position 108 and/or 113 for site-specific drug conjugation, and
- (b) at least one heterologous molecule covalently conjugated to one or both of the cysteines at position 108 and 113 of the CH2 domain, wherein numbering is according to the IMGT.

2. The isolated antigen-binding member conjugate of claim 1, wherein the heterologous molecule is conjugated to one or both of the cysteines at position 108 and 113 of the CH2 domain via a conjugation linker, wherein numbering is according to the IMGT.

3. The isolated antigen-binding member conjugate of claim 2, wherein the conjugation linker comprises a maleimide group.

4. A preparation comprising the isolated antigen-binding member conjugate of claim 1.

5. A method of producing the isolated antigen-binding member conjugate an of claim 1, comprising the steps:
- a) providing an antigen-binding member comprising a specific antigen-binding moiety and an antibody Fc region comprising a CH2 domain, having an engineered cysteine substitution at position 108 and/or 113, wherein numbering is according to the IMGT; and
- b) reacting at least one thiol group of one or both of the cysteines at position 108 and 113 of the CH2 domain with a heterologous molecule by a site-specific conjugation method.

6. The method of claim 5, wherein said at least one thiol group is reacting with said heterologous molecule by a Michael reaction, using a conjugation linker comprising a maleimide group.

7. The isolated antigen-binding member conjugate of claim 1, wherein the heterologous molecule is selected from the group consisting of a drug, a toxin, an enzyme, and a label.

8. The isolated antigen-binding member conjugate of claim 1, wherein the antigen-binding moiety is fused to the CH2 domain's N-terminus.

9. The isolated antigen-binding member conjugate of claim 1, wherein the CH2 domain comprises cysteine substitutions, N108C and L113C, wherein numbering is according to the IMGT.

10. The isolated antigen-binding member conjugate of claim 1, wherein the antigen-binding moiety comprises an antigen-binding portion of an antibody.

11. The isolated antigen-binding member conjugate of claim 1, wherein the antigen-binding moiety is selected from the group consisting of a Fab, F(ab')2, scFv, Fd, and Fv.

12. The isolated antigen-binding member conjugate of claim 1, wherein the antigen-binding moiety is fused to the CH2 domain's N-terminus via a linker and/or hinge region.

13. The isolated antigen-binding member conjugate of claim 1, wherein of the CH2 domain's C-terminus is fused to a CH3 domain's N-terminus.

14. The isolated antigen-binding member conjugate of claim 1, wherein the antibody Fc region is of an IgG, IgA, IgM, or IgE isotype.

15. The isolated antigen-binding member conjugate of claim 1, wherein the antigen-binding member is selected from the group consisting of a monoclonal antibody, a bispecific antibody, and a multispecific antibody.

16. The isolated antigen-binding member conjugate of claim 1, wherein the antigen-binding moiety specifically recognizes EGFR or HER2.

17. The isolated antigen-binding member conjugate of claim 1, wherein the antibody Fc region comprises SEQ ID NO: 4, 5, or 6.

* * * * *

UNITED STATES PATENT AND TRADEMARK OFFICE
CERTIFICATE OF CORRECTION

PATENT NO. : 11,623,963 B2
APPLICATION NO. : 16/650124
DATED : April 11, 2023
INVENTOR(S) : Gordana Wozniak-Knopp et al.

It is certified that error appears in the above-identified patent and that said Letters Patent is hereby corrected as shown below:

In the Claims

Claim 1, Column 133, Line 43, delete "a specific antigen-binding" and insert --(a) a specific antigen-binding-- therefor.

Claim 11, Column 134, Line 64, delete "F(ab')2" and insert --$F(ab')_2$-- therefor.

Signed and Sealed this
Thirtieth Day of May, 2023

Katherine Kelly Vidal
*Director of the United States Patent and Trademark Office*

SEQUENCE LISTING

```
<160> NUMBER OF SEQ ID NOS: 91

<210> SEQ ID NO 1
<211> LENGTH: 111
<212> TYPE: PRT
<213> ORGANISM: Artificial sequence
<220> FEATURE:
<223> OTHER INFORMATION: Antibody domain

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Cys Lys
                85                  90                  95

Ala Leu Pro Ala Pro Ile Glu Lys Thr Ile Ser Lys Ala Lys Gly
            100                 105                 110

<210> SEQ ID NO 2
<211> LENGTH: 111
<212> TYPE: PRT
<213> ORGANISM: Artificial sequence
<220> FEATURE:
<223> OTHER INFORMATION: Antibody domain

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Cys Pro Ala Pro Ile Glu Lys Thr Ile Ser Lys Ala Lys Gly
```

<210> SEQ ID NO 3
<211> LENGTH: 111
<212> TYPE: PRT
<213> ORGANISM: Artificial sequence
<220> FEATURE:
<223> OTHER INFORMATION: Antibody domain

<400> SEQUENCE: 3

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Cys Lys
                85                  90                  95
Ala Cys Pro Ala Pro Ile Glu Lys Thr Ile Ser Lys Ala Lys Gly
            100                 105                 110
```

<210> SEQ ID NO 4
<211> LENGTH: 217
<212> TYPE: PRT
<213> ORGANISM: Artificial sequence
<220> FEATURE:
<223> OTHER INFORMATION: Fc mutant

<400> SEQUENCE: 4

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Cys Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Asp Glu Leu
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
```

Phe Ser Cys Ser Val Met His Glu Ala Leu His Asn His Tyr Thr Gln
                195                 200                 205
Lys Ser Leu Ser Leu Ser Pro Gly Lys
    210                 215

<210> SEQ ID NO 5
<211> LENGTH: 217
<212> TYPE: PRT
<213> ORGANISM: Artificial sequence
<220> FEATURE:
<223> OTHER INFORMATION: Fc mutant

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Cys Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 6
<211> LENGTH: 217
<212> TYPE: PRT
<213> ORGANISM: Artificial sequence
<220> FEATURE:
<223> OTHER INFORMATION: Fc mutant

<400> SEQUENCE: 6

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Cys Lys
                 85                  90                  95

Ala Cys Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 7
<211> LENGTH: 15
<212> TYPE: PRT
<213> ORGANISM: Homo sapiens

<400> SEQUENCE: 7

Glu Pro Lys Ser Cys Asp Lys Thr His Thr Cys Pro Pro Cys Pro
1               5                   10                  15

<210> SEQ ID NO 8
<211> LENGTH: 106
<212> TYPE: PRT
<213> ORGANISM: Homo sapiens

<400> SEQUENCE: 8

Gln Pro Arg Glu Pro Gln Val Tyr Thr Leu Pro Pro Ser Arg Asp Glu
1               5                   10                  15

Leu Thr Lys Asn Gln Val Ser Leu Thr Cys Leu Val Lys Gly Phe Tyr
            20                  25                  30

Pro Ser Asp Ile Ala Val Glu Trp Glu Ser Asn Gly Gln Pro Glu Asn
        35                  40                  45

Asn Tyr Lys Thr Thr Pro Pro Val Leu Asp Ser Asp Gly Ser Phe Phe
    50                  55                  60

Leu Tyr Ser Lys Leu Thr Val Asp Lys Ser Arg Trp Gln Gln Gly Asn
65                  70                  75                  80

Val Phe Ser Cys Ser Val Met His Glu Ala Leu His Asn His Tyr Thr
                85                  90                  95

Gln Lys Ser Leu Ser Leu Ser Pro Gly Lys
            100                 105

<210> SEQ ID NO 9
<211> LENGTH: 109
<212> TYPE: PRT
<213> ORGANISM: Artificial sequence
<220> FEATURE:
<223> OTHER INFORMATION: Antibody mutant
```

```
<400> SEQUENCE: 9

Gln Pro Phe Arg Pro Glu Val His Leu Leu Pro Pro Ser Arg Glu Glu
1               5                   10                  15

Met Thr Lys Asn Gln Val Ser Leu Thr Cys Leu Ala Arg Gly Phe Tyr
            20                  25                  30

Pro Lys Asp Ile Ala Val Glu Trp Glu Ser Asn Gly Gln Pro Glu Asn
        35                  40                  45

Asn Tyr Lys Thr Thr Pro Ser Arg Gln Glu Pro Ser Gln Gly Thr Thr
    50                  55                  60

Thr Phe Ala Val Thr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Thr Ile Ser Leu Ser Pro Gly Lys
            100                 105

<210> SEQ ID NO 10
<211> LENGTH: 109
<212> TYPE: PRT
<213> ORGANISM: Artificial sequence
<220> FEATURE:
<223> OTHER INFORMATION: Antibody mutant

<400> SEQUENCE: 10

Gln Pro Arg Glu Pro Gln Val Tyr Thr Leu Pro Pro Ser Glu Glu
1               5                   10                  15

Leu Ala Leu Asn Glu Leu Val Thr Leu Thr Cys Leu Val Lys Gly Phe
            20                  25                  30

Tyr Pro Ser Asp Ile Ala Val Glu Trp Leu Gln Gly Ser Gln Glu Leu
        35                  40                  45

Pro Arg Glu Lys Tyr Leu Thr Trp Ala Pro Val Leu Asp Ser Asp Gly
    50                  55                  60

Ser Phe Phe Leu Tyr Ser Ile Leu Arg Val Ala Ala Glu Asp Trp Lys
65                  70                  75                  80

Lys Gly Asp Thr Phe Ser Cys Ser Val Met His Glu Ala Leu His Asn
                85                  90                  95

His Tyr Thr Gln Lys Ser Leu Asp Arg Ser Pro Gly Lys
            100                 105

<210> SEQ ID NO 11
<211> LENGTH: 6
<212> TYPE: PRT
<213> ORGANISM: Artificial sequence
<220> FEATURE:
<223> OTHER INFORMATION: Recognition sequence

<400> SEQUENCE: 11

Glu Leu Asp Lys Trp Ala
1               5

<210> SEQ ID NO 12
<211> LENGTH: 223
<212> TYPE: PRT
<213> ORGANISM: Homo sapiens

<400> SEQUENCE: 12

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
```

```
            20                  25                  30
Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
                130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
                180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
                210                 215                 220

<210> SEQ ID NO 13
<211> LENGTH: 223
<212> TYPE: PRT
<213> ORGANISM: Artificial sequence
<220> FEATURE:
<223> OTHER INFORMATION: Fc mutant

<400> SEQUENCE: 13

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Glu Leu Asp Lys Trp Ala Pro Glu
        35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys Gly Gln Pro Arg Glu Pro Gln Val Tyr Thr Leu Pro
                115                 120                 125

Pro Ser Arg Asp Glu Leu Thr Lys Asn Gln Val Ser Leu Thr Cys Leu
                130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
```

```
                    165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 14
<211> LENGTH: 223
<212> TYPE: PRT
<213> ORGANISM: Artificial sequence
<220> FEATURE:
<223> OTHER INFORMATION: Fc mutant

<400> SEQUENCE: 14

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Leu Asp Lys Trp Ala Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 15
<211> LENGTH: 223
<212> TYPE: PRT
<213> ORGANISM: Artificial sequence
<220> FEATURE:
<223> OTHER INFORMATION: Fc mutant

<400> SEQUENCE: 15

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30
```

-continued

```
Pro Glu Val Thr Cys Val Val Asp Val Ser His Glu Asp Pro Glu
         35                  40                  45
Val Lys Phe Asn Trp Tyr Val Asp Gly Val Glu Val His Asn Ala Lys
 50                  55                  60
Thr Lys Pro Arg Glu Glu Gln Tyr Asn Ser Thr Tyr Arg Val Val Ser
 65                  70                  75                  80
Val Leu Thr Val Leu His Gln Asp Trp Leu Asn Gly Lys Glu Tyr Lys
                 85                  90                  95
Cys Lys Val Ser Glu Leu Asp Lys Trp Ala Pro Ile Glu Lys Thr Ile
                100                 105                 110
Ser Lys Ala Lys Gly Gln Pro Arg Glu Pro Gln Val Tyr Thr Leu Pro
            115                 120                 125
Pro Ser Arg Asp Glu Leu Thr Lys Asn Gln Val Ser Leu Thr Cys Leu
130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Val Leu Asp Ser
                165                 170                 175
Asp Gly Ser Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
His Asn His Tyr Thr Gln Lys Ser Leu Ser Leu Ser Pro Gly Lys
    210                 215                 220
```

<210> SEQ ID NO 16
<211> LENGTH: 57
<212> TYPE: DNA
<213> ORGANISM: Artificial sequence
<220> FEATURE:
<223> OTHER INFORMATION: Primer

<400> SEQUENCE: 16
gtcacatgcg tggtggtgga actcgataag tgggcccctg aggtcaagtt caactgg     57

<210> SEQ ID NO 17
<211> LENGTH: 57
<212> TYPE: DNA
<213> ORGANISM: Artificial sequence
<220> FEATURE:
<223> OTHER INFORMATION: Primer

<400> SEQUENCE: 17
ccagttgaac ttgacctcag gggcccactt atcgagttcc accaccacgc atgtgac     57

<210> SEQ ID NO 18
<211> LENGTH: 56
<212> TYPE: DNA
<213> ORGANISM: Artificial sequence
<220> FEATURE:
<223> OTHER INFORMATION: Primer

<400> SEQUENCE: 18
caagacaaag ccgcgcgagg aactcgataa gtgggcctac cgtgtggtca gcgtcc      56

<210> SEQ ID NO 19
<211> LENGTH: 56
<212> TYPE: DNA
<213> ORGANISM: Artificial sequence
<220> FEATURE:
<223> OTHER INFORMATION: Primer

<400> SEQUENCE: 19
ggacgctgac cacacggtag gcccacttat cgagttcctc gcgcggcttt gtcttg    56

<210> SEQ ID NO 20
<211> LENGTH: 55
<212> TYPE: DNA
<213> ORGANISM: Artificial sequence
<220> FEATURE:
<223> OTHER INFORMATION: Primer

<400> SEQUENCE: 20
caagtgcaag gtctccgaac tcgataagtg ggcccccatc gagaaaacca tctcc    55

<210> SEQ ID NO 21
<211> LENGTH: 55
<212> TYPE: DNA
<213> ORGANISM: Artificial sequence
<220> FEATURE:
<223> OTHER INFORMATION: Primer

<400> SEQUENCE: 21
ggagatggtt ttctcgatgg gggcccactt atcgagttcg agaccttgc acttg    55

<210> SEQ ID NO 22
<211> LENGTH: 43
<212> TYPE: DNA
<213> ORGANISM: Artificial sequence
<220> FEATURE:
<223> OTHER INFORMATION: Primer

<400> SEQUENCE: 22
ggagtacaag tgcaaggtct gtaacaaagc cctcccagcc ccc    43

<210> SEQ ID NO 23
<211> LENGTH: 43
<212> TYPE: DNA
<213> ORGANISM: Artificial sequence
<220> FEATURE:
<223> OTHER INFORMATION: Primer

<400> SEQUENCE: 23
gggggctggg agggctttgt tacagacctt gcacttgtac tcc    43

<210> SEQ ID NO 24
<211> LENGTH: 42
<212> TYPE: DNA
<213> ORGANISM: Artificial sequence
<220> FEATURE:
<223> OTHER INFORMATION: Primer

<400> SEQUENCE: 24
gggggctggg agggctttac aggagaccttt gcacttgtac tc    42

<210> SEQ ID NO 25
<211> LENGTH: 42
<212> TYPE: DNA
<213> ORGANISM: Artificial sequence
<220> FEATURE:
<223> OTHER INFORMATION: Primer

<400> SEQUENCE: 25 ggggggctggg agggctttac aggagacctt gcacttgtac tc    42

<210> SEQ ID NO 26

<211> LENGTH: 34
<212> TYPE: DNA
<213> ORGANISM: Artificial sequence
<220> FEATURE:
<223> OTHER INFORMATION: Primer

<400> SEQUENCE: 26
gtgcaaggtc tccaactgtg ccctcccagc cccc          34

<210> SEQ ID NO 27
<211> LENGTH: 34
<212> TYPE: DNA
<213> ORGANISM: Artificial sequence
<220> FEATURE:
<223> OTHER INFORMATION: Primer

<400> SEQUENCE: 27
gggggctggg agggcacagt tggagacctt gcac          34

<210> SEQ ID NO 28
<211> LENGTH: 36
<212> TYPE: DNA
<213> ORGANISM: Artificial sequence
<220> FEATURE:
<223> OTHER INFORMATION: Primer

<400> SEQUENCE: 28
gcaaggtctc caacaaatgc ctcccagccc ccatcg          36

<210> SEQ ID NO 29
<211> LENGTH: 36
<212> TYPE: DNA
<213> ORGANISM: Artificial sequence
<220> FEATURE:
<223> OTHER INFORMATION: Primer

<400> SEQUENCE: 29 cgatggggc tgggaggcat ttgttggaga ccttgc          36

<210> SEQ ID NO 30
<211> LENGTH: 40
<212> TYPE: DNA
<213> ORGANISM: Artificial sequence
<220> FEATURE:
<223> OTHER INFORMATION: Primer

<400> SEQUENCE: 30
ggtctccaac aaagcctgcc cagcccccat cgagaaaacc          40

<210> SEQ ID NO 31
<211> LENGTH: 40
<212> TYPE: DNA
<213> ORGANISM: Artificial sequence
<220> FEATURE:
<223> OTHER INFORMATION: Primer

<400> SEQUENCE: 31
ggttttctcg atgggggctg ggcaggcttt gttggagacc          40

<210> SEQ ID NO 32
<211> LENGTH: 40
<212> TYPE: DNA
<213> ORGANISM: Artificial sequence
<220> FEATURE:
<223> OTHER INFORMATION: Primer

<400> SEQUENCE: 32
ggtctccaac aaagccctct gcgcccccat cgagaaaacc                     40

<210> SEQ ID NO 33
<211> LENGTH: 40
<212> TYPE: DNA
<213> ORGANISM: Artificial sequence
<220> FEATURE:
<223> OTHER INFORMATION: Primer

<400> SEQUENCE: 33
ggttttctcg atggggcgc agagggcttt gttggagacc                      40

<210> SEQ ID NO 34
<211> LENGTH: 40
<212> TYPE: DNA
<213> ORGANISM: Artificial sequence
<220> FEATURE:
<223> OTHER INFORMATION: Primer

<400> SEQUENCE: 34
ggtctccaac aaagccctcc catgccccat cgagaaaacc                     40

<210> SEQ ID NO 35
<211> LENGTH: 40
<212> TYPE: DNA
<213> ORGANISM: Artificial sequence
<220> FEATURE:
<223> OTHER INFORMATION: Primer

<400> SEQUENCE: 35
ggttttctcg atggggcatg ggagggcttt gttggagacc                     40

<210> SEQ ID NO 36
<211> LENGTH: 38
<212> TYPE: DNA
<213> ORGANISM: Artificial sequence
<220> FEATURE:
<223> OTHER INFORMATION: Primer

<400> SEQUENCE: 36
gagtacaagt gcaaggtgtg taacaaggcc ctgcctgc                       38

<210> SEQ ID NO 37
<211> LENGTH: 38
<212> TYPE: DNA
<213> ORGANISM: Artificial sequence
<220> FEATURE:
<223> OTHER INFORMATION: Primer

<400> SEQUENCE: 37
gcaggcaggg ccttgttaca caccttgcac ttgtactc                       38

<210> SEQ ID NO 38
<211> LENGTH: 42
<212> TYPE: DNA
<213> ORGANISM: Artificial sequence
<220> FEATURE:
<223> OTHER INFORMATION: Primer

<400> SEQUENCE: 38
gagtacaagt gcaaggtgag ctgtaaagcc ctgcctgccc cc                  42

<210> SEQ ID NO 39
<211> LENGTH: 42
<212> TYPE: DNA

```
<213> ORGANISM: Artificial sequence
<220> FEATURE:
<223> OTHER INFORMATION: Primer

<400> SEQUENCE: 39
gggggcaggc agggctttac agctcacctt gcacttgtac tc                    42

<210> SEQ ID NO 40
<211> LENGTH: 40
<212> TYPE: DNA
<213> ORGANISM: Artificial sequence
<220> FEATURE:
<223> OTHER INFORMATION: Primer

<400> SEQUENCE: 40
ggtgagcaac aaggcctgtc ctgcacccat cgagaagacc                       40

<210> SEQ ID NO 41
<211> LENGTH: 40
<212> TYPE: DNA
<213> ORGANISM: Artificial sequence
<220> FEATURE:
<223> OTHER INFORMATION: Primer

<400> SEQUENCE: 41
ggtcttctcg atgggtgcag gacaggcctt gttgctcacc                       40

<210> SEQ ID NO 42
<211> LENGTH: 223
<212> TYPE: PRT
<213> ORGANISM: Artificial sequence
<220> FEATURE:
<223> OTHER INFORMATION: Fc mutant

<400> SEQUENCE: 42
```

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Cys Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Phe Phe Thr Tyr Trp Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Arg Arg Arg
            180                 185                 190

Trp Thr Ala Gly Asn Val Phe Ser Cys Ser Val Met His Glu Ala Leu

```
            195                 200                 205
His Asn His Tyr Thr Gln Lys Ser Leu Ser Leu Ser Pro Gly Lys
    210                 215                 220

<210> SEQ ID NO 43
<211> LENGTH: 223
<212> TYPE: PRT
<213> ORGANISM: Artificial sequence
<220> FEATURE:
<223> OTHER INFORMATION: Fc mutant

<400> SEQUENCE: 43

Thr Cys Pro Pro Cys Pro Ala Pro Glu Leu Leu Gly Gly Pro Ser Val
1               5                  10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Cys Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Phe Phe Thr Tyr Trp Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Arg Arg Arg
            180                 185                 190

Trp Thr Ala Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 44
<211> LENGTH: 468
<212> TYPE: PRT
<213> ORGANISM: Artificial sequence
<220> FEATURE:
<223> OTHER INFORMATION: Antibody sequence

<400> SEQUENCE: 44

Met Ala Val Leu Gly Leu Leu Phe Cys Leu Val Thr Phe Pro Ser Cys
1               5                  10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60
```

```
Glu Trp Leu Gly Val Ile Trp Ser Gly Gly Asn Thr Asp Tyr Asn Thr
 65                  70                  75                  80

Pro Phe Thr Ser Arg Leu Ser Ile Asn Lys Asp Asn Ser Lys Ser Gln
                 85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465
```

<210> SEQ ID NO 45
<211> LENGTH: 1404
<212> TYPE: DNA
<213> ORGANISM: Artificial sequence
<220> FEATURE:
<223> OTHER INFORMATION: Antibody sequence

<400> SEQUENCE: 45

```
atggctgtct tggggctgct cttctgcctg gtgacattcc caagctgtgt cctatcccag      60
gtgcagctga agcagtcagg acctggccta gtgcagccct cacagagcct gtccatcacc     120
tgcacagtct ctggtttctc attaactaac tatggtgtac actgggttcg ccagtctcca     180
ggaaagggtc tggagtggct gggagtgata tggagtggtg aaacacaga ctataataca      240
cctttcacat ccagactgag catcaacaag acaattcca agagccaagt tttctttaaa      300
atgaacagtc tgcaatctaa tgacacagcc atatattact gtgccagagc cctcacctac     360
tatgattacg agtttgctta ctggggccaa gggactctgg tcactgtctc tgcagctagc     420
accaagggcc cagcgtgtt ccctctggcc cccagctcca gagcacctc cggcggcacc       480
gccgccctgg gctgcctggt gaaggattac ttcccagagc cgtgaccgt gagctggaac      540
agcgcgccc tgaccagcgg cgtgcacacc tttcccgccg tgctgcagtc cagcggcctg      600
tactccctga gcagcgtggt gaccgtgccc agcagcagcc tgggcaccca gacctacatc     660
tgcaatgtga accacaagcc cagcaatacc aaggtggata gaaggtgga gcccaagagc      720
tgcgacaaga cacacacgtg tccccatgt cccgccctg agctgctggg cggccttcc        780
gtgttcctgt tccctcccaa gccaaaggac accctgatga tctcccggac ccctgaggtg     840
acctgtgtgg tggtggacgt gagccacgag gacccagagg tgaagttcaa ctggtacgtg     900
gacggcgtgg aggtgcacaa cgccaagacc aagcctagag aggagcagta caacagcacc     960
taccgcgtgg tgagcgtgct gaccgtgctg caccaggatt ggctgaatgg caaggagtac    1020
aagtgcaagg tgagcaacaa ggccctgcct gcccccatcg agaagaccat ctccaaggcc    1080
aagggccagc ctcgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacacagaag    1380
agcctctccc tgtctccggg taaa                                           1404
```

<210> SEQ ID NO 46
<211> LENGTH: 234
<212> TYPE: PRT
<213> ORGANISM: Artificial sequence
<220> FEATURE:
<223> OTHER INFORMATION: Antibody sequence

<400> SEQUENCE: 46

```
Met Val Ser Thr Pro Gln Phe Leu Val Phe Leu Leu Phe Trp Ile Pro
1               5                   10                  15

Ala Ser Arg Gly Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60
```

```
Arg Leu Leu Ile Lys Tyr Ala Ser Glu Ser Ile Gly Ile Pro Ser
 65                  70                  75                  80

Arg Phe Ser Gly Ser Gly Ser Gly Thr Asp Phe Thr Leu Ser Ile Asn
                 85                  90                  95

Ser Val Glu Ser Glu Asp Ile Ala Asp Tyr Tyr Cys Gln Gln Asn Asn
            100                 105                 110

Asn Trp Pro Thr Thr Phe Gly Ala Gly Thr Lys Leu Glu Leu Lys Arg
        115                 120                 125

Thr Val Ala Ala Pro Ser Val Phe Ile Phe Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 47
<211> LENGTH: 702
<212> TYPE: DNA
<213> ORGANISM: Artificial sequence
<220> FEATURE:
<223> OTHER INFORMATION: Antibody sequence

<400> SEQUENCE: 47

```
atggtatcca cacctcagtt ccttgtattt ttgcttttct ggattccagc ctccagaggt    60
gacatcttgc tgactcagtc tccagtcatc ctgtctgtga gtccaggaga aagagtcagt   120
ttctcctgca gggccagtca gagtattggc acaaacatac actggtatca gcaaagaaca   180
aatggttctc caaggcttct cataaagtat gcttctgagt ctatctctgg aatcccttcc   240
aggtttagtg gcagtggatc agggacagat tttactctta gcatcaacag tgtggagtct   300
gaagatattg cagattatta ctgtcaacaa aataataact ggccaaccac gttcggtgct   360
gggaccaagc tggagctgaa aagaactgtt gcggcgccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag cacccctgacg   600
ctgagcaaag cagactacga gaaacacaaa gtctacgcct gcgaagtcac ccatcagggc   660
ctgagctcgc ccgtcacaaa gagcttcaac aggggagagt gt                      702
```

<210> SEQ ID NO 48
<211> LENGTH: 34
<212> TYPE: DNA
<213> ORGANISM: Artificial sequence
<220> FEATURE:
<223> OTHER INFORMATION: Primer

<400> SEQUENCE: 48

```
caagtgcaag gtgagctgta aggccctgcc tgcc                                34
```

```
<210> SEQ ID NO 49
<211> LENGTH: 34
<212> TYPE: DNA
<213> ORGANISM: Artificial sequence
<220> FEATURE:
<223> OTHER INFORMATION: Primer

<400> SEQUENCE: 49
ggcaggcagg gccttacagc tcaccttgca cttg                                34

<210> SEQ ID NO 50
<211> LENGTH: 36
<212> TYPE: DNA
<213> ORGANISM: Artificial sequence
<220> FEATURE:
<223> OTHER INFORMATION: Primer

<400> SEQUENCE: 50
gtgagcaaca aggcctgccc tgcccccatc gagaag                              36

<210> SEQ ID NO 51
<211> LENGTH: 36
<212> TYPE: DNA
<213> ORGANISM: Artificial sequence
<220> FEATURE:
<223> OTHER INFORMATION: Primer

<400> SEQUENCE: 51
cttctcgatg ggggcagggc aggccttgtt gctcac                              36

<210> SEQ ID NO 52
<211> LENGTH: 37
<212> TYPE: DNA
<213> ORGANISM: Artificial sequence
<220> FEATURE:
<223> OTHER INFORMATION: Primer

<400> SEQUENCE: 52
ggacgtgagc cacgaggact gcgaggtgaa gttcaac                             37

<210> SEQ ID NO 53
<211> LENGTH: 37
<212> TYPE: DNA
<213> ORGANISM: Artificial sequence
<220> FEATURE:
<223> OTHER INFORMATION: Primer

<400> SEQUENCE: 53
gttgaacttc acctcgcagt cctcgtggct cacgtcc                             37

<210> SEQ ID NO 54
<211> LENGTH: 34
<212> TYPE: DNA
<213> ORGANISM: Artificial sequence
<220> FEATURE:
<223> OTHER INFORMATION: Primer

<400> SEQUENCE: 54
cgccaagacc aagccttgcg aggagcagta caac                                34

<210> SEQ ID NO 55
<211> LENGTH: 34
<212> TYPE: DNA
<213> ORGANISM: Artificial sequence
<220> FEATURE:
<223> OTHER INFORMATION: Primer
```

-continued

```
<400> SEQUENCE: 55
gttgtactgc tcctcgcaag gcttggtctt ggcg                                    34

<210> SEQ ID NO 56
<211> LENGTH: 37
<212> TYPE: DNA
<213> ORGANISM: Artificial sequence
<220> FEATURE:
<223> OTHER INFORMATION: Primer

<400> SEQUENCE: 56
ctcccaagcc aaaggacgtg ctgatgatct cccggac                                 37

<210> SEQ ID NO 57
<211> LENGTH: 37
<212> TYPE: DNA
<213> ORGANISM: Artificial sequence
<220> FEATURE:
<223> OTHER INFORMATION: Primer

<400> SEQUENCE: 57
gtccgggaga tcatcagcac gtcctttggc ttgggag                                 37

<210> SEQ ID NO 58
<211> LENGTH: 48
<212> TYPE: DNA
<213> ORGANISM: Artificial sequence
<220> FEATURE:
<223> OTHER INFORMATION: Primer

<400> SEQUENCE: 58
gcttctatcc cagcgatatc gtggtggagt gggagagcaa tgggcagc                     48

<210> SEQ ID NO 59
<211> LENGTH: 48
<212> TYPE: DNA
<213> ORGANISM: Artificial sequence
<220> FEATURE:
<223> OTHER INFORMATION: Primer

<400> SEQUENCE: 59
gctgcccatt gctctcccac tccaccacga tatcgctggg atagaagc                     48

<210> SEQ ID NO 60
<211> LENGTH: 34
<212> TYPE: DNA
<213> ORGANISM: Artificial sequence
<220> FEATURE:
<223> OTHER INFORMATION: Primer

<400> SEQUENCE: 60
ggtgagctgt aaggcctgtc ctgcccccat cgag                                    34

<210> SEQ ID NO 61
<211> LENGTH: 34
<212> TYPE: DNA
<213> ORGANISM: Artificial sequence
<220> FEATURE:
<223> OTHER INFORMATION: Primer

<400> SEQUENCE: 61
ctcgatgggg gcaggacagg ccttacagct cacc                                    34

<210> SEQ ID NO 62
```

```
<211> LENGTH: 466
<212> TYPE: PRT
<213> ORGANISM: Artificial sequence
<220> FEATURE:
<223> OTHER INFORMATION: Antibody sequence

<400> SEQUENCE: 62

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Pro Lys Ser
225                 230                 235                 240

Ser Asp Lys Thr His Thr Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Ala Gln Ser Thr Phe
305                 310                 315                 320

Arg Val Val Ser Val Leu Thr Val Val His Gln Asp Trp Leu Asn Gly
                325                 330                 335

Lys Glu Tyr Lys Cys Ala Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Met Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly
465

<210> SEQ ID NO 63
<211> LENGTH: 1398
<212> TYPE: DNA
<213> ORGANISM: Artificial sequence
<220> FEATURE:
<223> OTHER INFORMATION: Antibody sequence

<400> SEQUENCE: 63
atggctgtct tggggctgct cttctgcctg gtgacattcc caagctgtgt cctatcccag      60
gtgcagctga agcagtcagg acctggccta gtgcagccct cacagagcct gtccatcacc     120
tgcacagtct ctggtttctc attaactaac tatggtgtac actgggttcg ccagtctcca     180
ggaaagggtc tggagtggct gggagtgata tggagtggtg aaacacaga ctataataca      240 cctttcacat ccagactgag catcaacaag acaattcca agagccaagt tttcttaaa       300 atgaacagtc tgcaatctaa tgacacagcc atatattact gtgccagagc cctcacctac     360
tatgattacg agtttgctta ctgggggcaa gggactctgg tcactgtctc tgcagctagc     420
accaagggcc catcggtctt ccccctggcg ccctgctcca ggagcacctc cgagagcaca     480
gcggccctgg gctgcctggt caaggactac ttccccgaac cggtgacggt gtcgtggaac     540
tcaggcgctc tgaccagcgg cgtgcacacc ttcccagctg tcctacagtc ctcaggactc     600
tactccctca gcagcgtggt gaccgtgccc tccagcaact tcggcaccca gacctacacc     660
tgcaacgtag atcacaagcc cagcaacacc aaggtggaca agacagttga gcccaaatct     720
tctgacaaaa ctcacacatg cccaccgtgc ccagcaccac tgtggcagg accgtcagtc      780 ttcctcttcc ccccaaaacc caaggacacc ctcatgatct cccggaccccc tgaggtcacg    840 tgcgtggtgg tggacgtgag ccacgaagac cccgaggtcc agttcaactg gtacgtggac     900
ggcgtggagg tgcataatgc caagacaaag ccacgggagg agcaggccca gagcacgttc     960
cgtgtggtca gcgtcctcac cgttgtgcac caggactggc tgaacggcaa ggagtacaag    1020
tgcgctgtct ccaacaaagg cctcccagcc cccatcgaga aaccatctc caaaaccaaa     1080 gggcagcccc gagaaccaca ggtgtacacc ctgcccccat cccggagga gatgaccaag    1140 aaccaggtca gcctgacctg cctggtcaaa ggcttctacc ccagcgacat cgccgtggag    1200
tgggagagca atgggcagcc ggagaacaac tacaagacca cacctcccat gctggactcc    1260
gacggctcct tcttcctcta cagcaagctc accgtggaca gagcaggtg gcagcagggg    1320 aacgtcttct catgctccgt gatgcatgag gctctgcaca accactacac gcagaagagc    1380 ctctcccctgt ccccgggt                                                 1398

<210> SEQ ID NO 64
```

<211> LENGTH: 468
<212> TYPE: PRT
<213> ORGANISM: Artificial sequence
<220> FEATURE:
<223> OTHER INFORMATION: Antibody sequence

<400> SEQUENCE: 64

```
Met Lys Leu Pro Val Arg Leu Leu Val Leu Met Phe Trp Ile Pro Ala
1               5                   10                  15

Ser Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Ser Leu
        35                  40                  45

Thr Asn Tyr Gly Val His Trp Met Arg Gln Ala Pro Gly Gln Gly Leu
    50                  55                  60

Glu Trp Ile Gly Val Ile Trp Ser Gly Gly Asn Thr Asp Tyr Asn Thr
65                  70                  75                  80

Pro Phe Thr Ser Arg Val Thr Ile Thr Ser Asp Lys Ser Thr Ser Thr
                85                  90                  95

Ala Tyr Met Glu Leu Ser Ser Leu Arg Ser Glu Asp Thr Ala Val Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380
```

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
450                 455                 460

Ser Pro Gly Lys
465

<210> SEQ ID NO 65
<211> LENGTH: 1344
<212> TYPE: DNA
<213> ORGANISM: Artificial sequence
<220> FEATURE:
<223> OTHER INFORMATION: Antibody sequence

<400> SEQUENCE: 65
gaggtccaat tggtgcagtc tggagctgag gtgaagaagc ctggagcttc agtgaaggtg     60
tcctgcaaag cttctggatt ctcattaact aactatggtg tacactggat gcgtcaggct    120
cctgggcagg gtctcgagtg gattggagtg atatggagtg gtggaaacac agactataat    180
acacctttca catccagagt cacaatcact tcagacaaat ccaccagcac agcctacatg    240
gagctcagca gcctgaggtc tgaggacact gcggtctatt actgtgcaag agccctcacc    300
tactatgatt acgagtttgc ttactggggt caaggcaccc tggtcacagt ctcctcagcc    360
tccaccaagg gcccatcggt cttccccctg gcaccctcct ccaagagcac ctctggggc    420 acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctctag aaccctgag    780 gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac gatatccaaa   1020
gccaaagggc agccccgaga accacaggtg tacaccctgc cccatcacg ggaggagatg    1080 accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtcccc gggt                                          1344

<210> SEQ ID NO 66
<211> LENGTH: 233
<212> TYPE: PRT

<213> ORGANISM: Artificial sequence
<220> FEATURE:
<223> OTHER INFORMATION: Antibody sequence

<400> SEQUENCE: 66

```
Met Lys Leu Pro Val Arg Leu Leu Val Leu Met Phe Trp Ile Pro Ala
1               5                   10                  15
Ser Leu Ser Asp Ile Gln Met Thr Gln Ser Pro Ser Ser Leu Ser Ala
            20                  25                  30
Ser Val Gly Asp Arg Val Thr Ile Thr Cys Arg Ala Ser Gln Ser Ile
        35                  40                  45
Gly Thr Asn Ile His Trp Tyr Gln Gln Lys Pro Gly Lys Ala Pro Lys
    50                  55                  60
Leu Leu Ile Lys Tyr Ala Ser Glu Ser Ile Ser Gly Val Pro Ser Arg
65                  70                  75                  80
Phe Ser Gly Ser Gly Tyr Gly Thr Asp Phe Thr Leu Thr Ile Ser Ser
                85                  90                  95
Leu Gln Pro Glu Asp Val Ala Thr Tyr Tyr Cys Gln Gln Asn Tyr Asn
            100                 105                 110
Trp Pro Thr Thr Phe Gly Gln Gly Thr Lys Val Glu Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230
```

<210> SEQ ID NO 67
<211> LENGTH: 699
<212> TYPE: DNA
<213> ORGANISM: Artificial sequence
<220> FEATURE:
<223> OTHER INFORMATION: Antibody sequence

<400> SEQUENCE: 67

```
atgaagcttc ctgttaggct gttggtgctg atgttctgga tccctgctag cttaagcgat      60
atccagatga cccagtctcc gagctccctg tccgcatctg tgggagacag agtcaccatc     120
acttgcaggg ccagtcagag tattggcaca acatacact ggtatcagca gaagccaggg      180
aaagctccta agcttcttat taagtatgct tctgagtcta tctctggagt cccatcccga     240
ttctccggaa gtggctatgg tacagatttt actctcacaa ttagcagcct gcagcctgaa     300
gatgttgcaa cttactactg tcaacaaaat tataactggc caaccacgtt tggccaaggt     360
accaaggtgg aaataaaacg tacggtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgcccct c aatcgggtaa ctcccaggag     540
```
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgt                           699

<210> SEQ ID NO 68
<211> LENGTH: 33
<212> TYPE: DNA
<213> ORGANISM: Artificial sequence
<220> FEATURE:
<223> OTHER INFORMATION: Primer

<400> SEQUENCE: 68
caagtgcgct gtctcctgca aaggcctccc agc                                 33

<210> SEQ ID NO 69
<211> LENGTH: 33
<212> TYPE: DNA
<213> ORGANISM: Artificial sequence
<220> FEATURE:
<223> OTHER INFORMATION: Primer

<400> SEQUENCE: 69
gctgggaggc ctttgcagga gacagcgcac ttg                                 33

<210> SEQ ID NO 70
<211> LENGTH: 33
<212> TYPE: DNA
<213> ORGANISM: Artificial sequence
<220> FEATURE:
<223> OTHER INFORMATION: Primer

<400> SEQUENCE: 70
gtctccaaca aaggctgccc agcccccatc gag                                 33

<210> SEQ ID NO 71
<211> LENGTH: 33
<212> TYPE: DNA
<213> ORGANISM: Artificial sequence
<220> FEATURE:
<223> OTHER INFORMATION: Primer

<400> SEQUENCE: 71
ctcgatgggg gctgggcagc ctttgttgga gac                                 33

<210> SEQ ID NO 72
<211> LENGTH: 33
<212> TYPE: DNA
<213> ORGANISM: Artificial sequence
<220> FEATURE:
<223> OTHER INFORMATION: Primer

<400> SEQUENCE: 72
gtctcctgca aaggctgccc agcccccatc gag                                 33

<210> SEQ ID NO 73
<211> LENGTH: 33
<212> TYPE: DNA
<213> ORGANISM: Artificial sequence
<220> FEATURE:
<223> OTHER INFORMATION: Primer

<400> SEQUENCE: 73
ctcgatgggg gctgggcagc ctttgcagga gac                                 33

```
<210> SEQ ID NO 74
<211> LENGTH: 33
<212> TYPE: DNA
<213> ORGANISM: Artificial sequence
<220> FEATURE:
<223> OTHER INFORMATION: Primer

<400> SEQUENCE: 74
taccccagcg acatcgtggt ggagtgggag agc                                33

<210> SEQ ID NO 75
<211> LENGTH: 33
<212> TYPE: DNA
<213> ORGANISM: Artificial sequence
<220> FEATURE:
<223> OTHER INFORMATION: Primer

<400> SEQUENCE: 75
gctctcccac tccaccacga tgtcgctggg gta                                33

<210> SEQ ID NO 76
<211> LENGTH: 33
<212> TYPE: DNA
<213> ORGANISM: Artificial sequence
<220> FEATURE:
<223> OTHER INFORMATION: Primer

<400> SEQUENCE: 76
gtgagccacg aagactgcga ggtccagttc aac                                33

<210> SEQ ID NO 77
<211> LENGTH: 33
<212> TYPE: DNA
<213> ORGANISM: Artificial sequence
<220> FEATURE:
<223> OTHER INFORMATION: Primer

<400> SEQUENCE: 77
gttgaactgg acctcgcagt cttcgtggct cac                                33

<210> SEQ ID NO 78
<211> LENGTH: 33
<212> TYPE: DNA
<213> ORGANISM: Artificial sequence
<220> FEATURE:
<223> OTHER INFORMATION: Primer

<400> SEQUENCE: 78
gccaagacaa agccatgcga ggagcaggcc cag                                33

<210> SEQ ID NO 79
<211> LENGTH: 33
<212> TYPE: DNA
<213> ORGANISM: Artificial sequence
<220> FEATURE:
<223> OTHER INFORMATION: Primer

<400> SEQUENCE: 79
ctgggcctgc tcctcgcatg gctttgtctt ggc                                33

<210> SEQ ID NO 80
<211> LENGTH: 501
<212> TYPE: PRT
<213> ORGANISM: Artificial sequence
<220> FEATURE:
<223> OTHER INFORMATION: Antibody sequence
```

<400> SEQUENCE: 80

```
Met Lys Leu Pro Val Arg Leu Leu Val Leu Met Phe Trp Ile Pro Ala
1               5                   10                  15
Ser Leu Ser Glu Val Gln Leu Val Gln Ser Gly Ala Glu Val Lys Lys
            20                  25                  30
Pro Gly Ala Ser Val Lys Val Ser Cys Lys Ala Ser Gly Phe Ser Leu
        35                  40                  45
Thr Asn Tyr Gly Val His Trp Met Arg Gln Ala Pro Gly Gln Gly Leu
50                  55                  60
Glu Trp Ile Gly Val Ile Trp Ser Gly Gly Asn Thr Asp Tyr Asn Thr
65                  70                  75                  80
Pro Phe Thr Ser Arg Val Thr Ile Thr Ser Asp Lys Ser Thr Ser Thr
                85                  90                  95
Ala Tyr Met Glu Leu Ser Ser Leu Arg Ser Asp Thr Ala Val Tyr
            100                 105                 110
Tyr Cys Ala Arg Ala Leu Thr Tyr Tyr Asp Tyr Glu Phe Ala Tyr Trp
        115                 120                 125
Gly Gln Gly Thr Leu Val Thr Val Ser Ser Gly Gly Gly Gly Ser Gly
130                 135                 140
Gly Gly Gly Ser Gly Gly Gly Ser Asp Ile Gln Met Thr Gln Ser
145                 150                 155                 160
Pro Ser Ser Leu Ser Ala Ser Val Gly Asp Arg Val Thr Ile Thr Cys
                165                 170                 175
Arg Ala Ser Gln Ser Ile Gly Thr Asn Ile His Trp Tyr Gln Gln Lys
            180                 185                 190
Pro Gly Lys Ala Pro Lys Leu Leu Ile Lys Tyr Ala Ser Glu Ser Ile
        195                 200                 205
Ser Gly Val Pro Ser Arg Phe Ser Gly Ser Gly Tyr Gly Thr Asp Phe
210                 215                 220
Thr Leu Thr Ile Ser Ser Leu Gln Pro Glu Asp Val Ala Thr Tyr Tyr
225                 230                 235                 240
Cys Gln Gln Asn Tyr Asn Trp Pro Thr Thr Phe Gly Gln Gly Thr Lys
                245                 250                 255
Val Glu Ile Lys Ser Ser Gly Pro Gly Val Glu Pro Lys Ser Ser Asp
            260                 265                 270
Lys Thr His Thr Cys Pro Pro Cys Pro Ala Pro Glu Leu Leu Gly Gly
        275                 280                 285
Pro Ser Val Phe Leu Phe Pro Pro Lys Pro Lys Asp Thr Leu Met Ile
290                 295                 300
Ser Arg Thr Pro Glu Val Thr Cys Val Val Val Asp Val Ser His Glu
305                 310                 315                 320
Asp Pro Glu Val Lys Phe Asn Trp Tyr Val Asp Gly Val Glu Val His
                325                 330                 335
Asn Ala Lys Thr Lys Pro Arg Glu Glu Gln Tyr Asn Ser Thr Tyr Arg
            340                 345                 350
Val Val Ser Val Leu Thr Val Leu His Gln Asp Trp Leu Asn Gly Lys
        355                 360                 365
Glu Tyr Lys Cys Lys Val Ser Asn Lys Ala Leu Pro Ala Pro Ile Glu
370                 375                 380
Lys Thr Ile Ser Lys Ala Lys Gly Gln Pro Arg Glu Pro Gln Val Tyr
385                 390                 395                 400
Thr Leu Pro Pro Pro Ser Glu Glu Leu Ala Leu Asn Glu Leu Val Thr
                405                 410                 415
```

```
Leu Thr Cys Leu Val Lys Gly Phe Tyr Pro Ser Asp Ile Ala Val Glu
            420                 425                 430

Trp Leu Gln Gly Ser Gln Glu Leu Pro Arg Glu Lys Tyr Leu Thr Trp
        435                 440                 445

Ala Pro Val Leu Asp Ser Asp Gly Ser Phe Phe Leu Tyr Ser Ile Leu
    450                 455                 460

Arg Val Ala Ala Glu Asp Trp Lys Lys Gly Asp Thr Phe Ser Cys Ser
465                 470                 475                 480

Val Met His Glu Ala Leu His Asn His Tyr Thr Gln Lys Ser Leu Asp
                485                 490                 495

Arg Ser Pro Gly Lys
            500

<210> SEQ ID NO 81
<211> LENGTH: 1503
<212> TYPE: DNA
<213> ORGANISM: Artificial sequence
<220> FEATURE:
<223> OTHER INFORMATION: Antibody sequence

<400> SEQUENCE: 81
atgaagcttc ctgttaggct gttggtgctg atgttctgga tccctgctag cttaagcgag       60
gtccaattgg tgcagtctgg agctgaggtg aagaagcctg gagcttcagt gaaggtgtcc      120
tgcaaagctt ctggattctc attaactaac tatggtgtac actggatgcg tcaggctcct      180
gggcagggtc tcgagtggat tggagtgata tggagtggtg gaaacacaga ctataataca      240
cctttcacat ccagagtcac aatcacttca gacaaatcca ccagcacagc ctacatggag      300
ctcagcagcc tgaggtctga ggacactgcg gtctattact gtgcaagagc cctcacctac      360
tatgattacg agtttgctta ctggggtcaa ggcaccctgg tcacagtctc ctcgggaggt      420
ggaggttctg gaggtggcgg atccggaggt ggcggttctg atatccagat gacccagtct      480
ccgagctccc tgtccgcatc tgtgggagac agagtcacca tcacttgcag ggccagtcag      540
agtattggca aaacataca ctggtatcag cagaagccag ggaaagctcc taagcttctt       600
attaagtatg cttctgagtc tatctctgga gtcccatccc gattctccgg aagtggctat      660
ggtacagatt ttactctcac aattagcagc ctgcagcctg aagatgttgc aacttactac      720
tgtcaacaaa attataactg gccaaccacg tttggccaag gtaccaaggt ggaaataaaa      780
tcttccggtc ctggagtgga gcctaaatct tctgacaaaa ctcacacgtg cccaccgtgc      840
ccagcacctg aactcctggg gggaccgtca gtcttcctct tccccccaaa acccaaggac      900
accctcatga tctctagaac ccctgaggtc acatgcgtgg tggtggacgt gagccacgaa      960
gaccctgagg tcaagttcaa ctggtacgtg acggcgtgg aggtgcataa tgccaagaca     1020
aagccgcggg aggagcagta caacagcacg taccgtgtgg tcagcgtcct caccgtcctg     1080
caccaggact ggctgaatgg caaggagtac aagtgcaagg tctccaacaa agccctccca     1140
gcccccatcg agaaaacgat atccaaagcc aaagggcagc ccgagaacc acaggtgtac      1200 accctgcccc caccgtcgga ggagctggcc ctgaacgagc tggtgacgct gacctgcctg     1260
gtcaaaggct tctatcccag cgacatcgcc gtggagtggg tgcaggggtc cggagagctg     1320
ccccgcgaga gtacctgac ttgggcaccc gtgctggact ccgacggctc cttcttcctc      1380
tatagtatac tgcgcgtggc agccgaggac tggaagaagg ggacaccttc tcatgctcc     1440 gtgatgcatg aggctctgca caaccactac acgcagaaga gcctcgaccg ctccccgggt     1500
``` aaa                                                              1503

<210> SEQ ID NO 82
<211> LENGTH: 470
<212> TYPE: PRT
<213> ORGANISM: Artificial sequence
<220> FEATURE:
<223> OTHER INFORMATION: Antibody sequence

<400> SEQUENCE: 82

Met Glu Thr Asp Thr Leu Leu Leu Trp Val Leu Leu Leu Trp Val Pro
1               5                   10                  15

Gly Ser Thr Gly Glu Val Gln Leu Val Gln Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Ala Met Ser Trp Val Arg Gln Ala Pro Gly Lys Gly
    50                  55                  60

Leu Glu Trp Val Ser Ala Ile Ser Gly Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Asp Arg Arg Ile Thr His Thr Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Phe Arg Pro Glu Val

```
                355             360             365
His Leu Leu Pro Pro Ser Arg Glu Glu Met Thr Lys Asn Gln Val Ser
    370                 375                 380

Leu Thr Cys Leu Ala Arg Gly Phe Tyr Pro Lys Asp Ile Ala Val Glu
385                 390                 395                 400

Trp Glu Ser Asn Gly Gln Pro Glu Asn Asn Tyr Lys Thr Thr Pro Ser
                405                 410                 415

Arg Gln Glu Pro Ser Gln Gly Thr Thr Thr Phe Ala Val Thr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Thr Ile
                450                 455                 460

Ser Leu Ser Pro Gly Lys
465                 470

<210> SEQ ID NO 83
<211> LENGTH: 1410
<212> TYPE: DNA
<213> ORGANISM: Artificial sequence
<220> FEATURE:
<223> OTHER INFORMATION: Antibody sequence

<400> SEQUENCE: 83
```

| | | | | | |
|---|---|---|---|---|---|
| atggagaccg | acaccctgct | gctgtgggtg | ctgctgctgt | gggtgcccgg | gtcgaccggc | 60 |
| gaagtgcagc | tggtgcagtc | tgggggaggc | ttggtacagc | ctggggggtc | cctgagactc | 120 |
| tcctgtgcag | cctctggatt | cacctttagc | agctatgcca | tgagctgggt | ccgccaggct | 180 |
| ccagggaagg | gctggagtg  | gtctcagct  | attagtggta | gtggtggtag | cacatactac | 240 |
| gcagactccg | tgaagggccg | gttcaccatc | tccagagaca | attccaagaa | cacgctgtat | 300 |
| ctgcaaatga | acagcctgag | agccgaggac | acggccgtat | attactgtgc | gaaagatcgg | 360 |
| cgtattaccc | acacctactg | gggccaggga | accctggtca | ccgtctcctc | agctagcacc | 420 |
| aagggcccat | cggtcttccc | cctggcaccc | tcctccaaga | gcacctctgg | ggcacagcg  | 480 |
| gccctgggct | gcctggtcaa | ggactacttc | cccgaaccgg | tgacggtgtc | gtggaactca | 540 |
| ggcgccctga | ccagcggcgt | gcacaccttc | ccggctgtcc | tacagtcctc | aggactctac | 600 |
| tccctcagca | gcgtggtgac | cgtgccctcc | agcagcttgg | gcacccagac | ctacatctgc | 660 |
| aacgtgaatc | acaagcccag | caacaccaag | gtggacaaga | gagttgagcc | caaatcttgt | 720 |
| gacaaaactc | acacatgccc | accgtgccca | gcacctgaac | tcctgggggg | accgtcagtc | 780 |
| ttcctcttcc | ccccaaaacc | caaggacacc | ctcatgatct | cccggacccc | tgaggtcaca | 840 |
| tgcgtggtgg | tggacgtgag | ccacgaagac | cctgaggtca | agttcaactg | gtacgtggac | 900 |
| ggcgtggagg | tgcataatgc | caagacaaag | ccgcgggagg | agcagtacaa | cagcacgtac | 960 |
| cgtgtggtca | gcgtcctcac | cgtcctgcac | caggactggc | tgaatggcaa | ggagtacaag | 1020 |
| tgcaaggtct | ccaacaaagc | cctcccagcc | cccatcgaga | aaacgatatc | caaagccaaa | 1080 |
| gggcagccct | tccggccaga | ggtccacctg | ctgcccccat | cacgggagga | gatgaccaag | 1140 |
| aaccaggtca | gcctgacctg | cctggcacgc | ggcttctatc | ccaaggacat | cgccgtggag | 1200 |
| tgggagagca | atgggcagcc | ggagaacaac | tacaagacca | cgccttcccg | gcaggagccc | 1260 |
| agccagggca | ccaccacctt | cgctgtgacc | tcgaagctca | ccgtggacaa | gagcagatgg | 1320 |
| cagcagggga | acgtcttctc | atgctccgtg | atgcatgagg | ctctgcacaa | ccactacacg | 1380 |

-continued

```
cagaagacca tctccctgtc cccgggtaaa                              1410
```

<210> SEQ ID NO 84
<211> LENGTH: 234
<212> TYPE: PRT
<213> ORGANISM: Artificial sequence
<220> FEATURE:
<223> OTHER INFORMATION: Antibody sequence

<400> SEQUENCE: 84

```
Met Glu Thr Asp Thr Leu Leu Leu Trp Val Leu Leu Leu Trp Val Pro
1               5                   10                  15

Gly Ser Thr Gly Glu Pro Val Leu Thr Gln Pro Pro Ser Val Ser Val
            20                  25                  30

Ala Pro Gly Glu Thr Ala Thr Ile Pro Cys Gly Gly Asp Ser Leu Gly
        35                  40                  45

Ser Lys Ile Val His Trp Tyr Gln Gln Arg Pro Gly Gln Ala Pro Leu
    50                  55                  60

Leu Val Val Tyr Asp Asp Ala Ala Arg Pro Ser Gly Ile Pro Glu Arg
65                  70                  75                  80

Phe Ser Gly Ser Lys Ser Gly Thr Thr Ala Thr Leu Thr Ile Ser Ser
                85                  90                  95

Val Glu Ala Gly Asp Glu Ala Asp Tyr Phe Cys Gln Val Tyr Asp Tyr
            100                 105                 110

His Ser Asp Val Glu Val Phe Gly Gly Gly Thr Lys Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Lys Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 85
<211> LENGTH: 34
<212> TYPE: DNA
<213> ORGANISM: Artificial sequence
<220> FEATURE:
<223> OTHER INFORMATION: Primer

<400> SEQUENCE: 85

```
caagtgcaag gtctcctgta aagccctccc agcc                         34
```

<210> SEQ ID NO 86
<211> LENGTH: 34
<212> TYPE: DNA
<213> ORGANISM: Artificial sequence
<220> FEATURE:
<223> OTHER INFORMATION: Primer

<400> SEQUENCE: 86

```
<210> SEQ ID NO 87
<211> LENGTH: 33
<212> TYPE: DNA
<213> ORGANISM: Artificial sequence
<220> FEATURE:
<223> OTHER INFORMATION: Primer

<400> SEQUENCE: 87
gtctccaaca aagcctgccc agcccccatc gag                           33

<210> SEQ ID NO 88
<211> LENGTH: 33
<212> TYPE: DNA
<213> ORGANISM: Artificial sequence
<220> FEATURE:
<223> OTHER INFORMATION: Primer

<400> SEQUENCE: 88
ctcgatgggg gctgggcagg ctttgttgga gac                           33

<210> SEQ ID NO 89
<211> LENGTH: 234
<212> TYPE: PRT
<213> ORGANISM: Artificial sequence
<220> FEATURE:
<223> OTHER INFORMATION: Antibody sequence

<400> SEQUENCE: 89
```
ggctgggagg gctttacagg agaccttgca cttg                          34

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

```
<210> SEQ ID NO 90
<211> LENGTH: 470
<212> TYPE: PRT
<213> ORGANISM: Artificial sequence
<220> FEATURE:
<223> OTHER INFORMATION: Antibody sequence

<400> SEQUENCE: 90

Met Lys Leu Pro Val Arg Leu Leu Val Leu Met Phe Trp Ile Pro Ala
1               5                   10                  15

Ser Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Cys Lys Ala Leu Pro
            340                 345                 350

Ala Pro Ile Glu Lys Thr Ile Ser Lys Ala Lys Gly Gln Pro Arg Glu
```

```
                355                 360                 365
Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 91
<211> LENGTH: 470
<212> TYPE: PRT
<213> ORGANISM: Artificial sequence
<220> FEATURE:
<223> OTHER INFORMATION: Antibody sequence

<400> SEQUENCE: 91

Met Lys Leu Pro Val Arg Leu Leu Val Leu Met Phe Trp Ile Pro Ala
1               5                   10                  15

Ser Leu Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
        50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
                100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Pro
225                 230                 235                 240

Lys Ser Cys Asp Lys Thr His Thr Cys Pro Pro Cys Pro Ala Pro Glu
```

-continued

|  |  |  |  |  | 245 |  |  |  | 250 |  |  |  | 255 |  |
|---|---|---|---|---|---|---|---|---|---|---|---|---|---|---|
| Leu | Leu | Gly | Gly<br>260 | Pro | Ser | Val | Phe | Leu<br>265 | Phe | Pro | Pro | Lys<br>270 | Pro | Lys | Asp |

Thr Leu Met Ile Ser Arg Thr Pro Glu Val Thr Cys Val Val Val Asp
        275                  280              285

Val Ser His Glu Asp Pro Glu Val Lys Phe Asn Trp Tyr Val Asp Gly
    290                  295                  300

Val Glu Val His Asn Ala Lys Thr Lys Pro Arg Glu Glu Gln Tyr Asn
305                  310                315                320

Ser Thr Tyr Arg Val Val Ser Val Leu Thr Val Leu His Gln Asp Trp
            325                330                335

Leu Asn Gly Lys Glu Tyr Lys Cys Lys Val Ser Asn Lys Ala Cys Pro
            340              345              350

Ala Pro Ile Glu Lys Thr Ile Ser Lys Ala Lys Gly Gln Pro Arg Glu
        355              360              365

Pro Gln Val Tyr Thr Leu Pro Pro Ser Arg Asp Glu Leu Thr Lys Asn
370                  375              380

Gln Val Ser Leu Thr Cys Leu Val Lys Gly Phe Tyr Pro Ser Asp Ile
385                  390              395              400

Ala Val Glu Trp Glu Ser Asn Gly Gln Pro Glu Asn Asn Tyr Lys Thr
            405              410              415

Thr Pro Pro Val Leu Asp Ser Asp Gly Ser Phe Phe Leu Tyr Ser Lys
        420              425              430

Leu Thr Val Asp Lys Ser Arg Trp Gln Gln Gly Asn Val Phe Ser Cys
        435              440              445

Ser Val Met His Glu Ala Leu His Asn His Tyr Thr Gln Lys Ser Leu
    450                455              460

Ser Leu Ser Pro Gly Lys
465                470